US008822651B2

(12) United States Patent
Chan-Hui

(10) Patent No.: US 8,822,651 B2
(45) Date of Patent: Sep. 2, 2014

(54) HUMAN RHINOVIRUS (HRV) ANTIBODIES

(75) Inventor: Po-Ying Chan-Hui, Bellevue, WA (US)

(73) Assignee: Theraclone Sciences, Inc., Seattle, WA (US)

( * ) Notice: Subject to any disclaimer, the term of this patent is extended or adjusted under 35 U.S.C. 154(b) by 0 days.

(21) Appl. No.: 13/596,463

(22) Filed: Aug. 28, 2012

(65) Prior Publication Data
US 2013/0052163 A1    Feb. 28, 2013

Related U.S. Application Data

(60) Provisional application No. 61/529,008, filed on Aug. 30, 2011.

(51) Int. Cl.
C07K 16/00    (2006.01)
(52) U.S. Cl.
USPC .................................. 530/388.15; 530/388.3
(58) Field of Classification Search
CPC . A61K 2039/505; A61K 39/00; A61K 39/12; A61K 2039/6075; A61K 2039/525; A61K 2039/6056; C07K 16/00; C07K 2317/77; C07K 14/005; C07K 16/08
See application file for complete search history.

(56) References Cited

U.S. PATENT DOCUMENTS

| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,485,045 A | 11/1984 | Regen |
| 4,544,545 A | 10/1985 | Ryan et al. |
| 4,554,101 A | 11/1985 | Hopp |
| 4,676,980 A | 6/1987 | Segal et al. |
| 4,816,567 A | 3/1989 | Cabilly et al. |
| 4,975,278 A | 12/1990 | Senter et al. |
| 5,013,556 A | 5/1991 | Woodle et al. |
| 5,053,394 A | 10/1991 | Ellestad et al. |
| 5,208,020 A | 5/1993 | Chari et al. |
| 5,229,275 A | 7/1993 | Goroff |
| 5,416,064 A | 5/1995 | Chari et al. |
| 5,500,362 A | 3/1996 | Robinson et al. |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,587,458 A | 12/1996 | King et al. |
| 5,591,669 A | 1/1997 | Krimpenfort et al. |
| 5,627,052 A | 5/1997 | Schrader |
| 5,641,870 A | 6/1997 | Rinderknecht et al. |
| 5,648,237 A | 7/1997 | Carter |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,789,199 A | 8/1998 | Joly et al. |
| 5,821,337 A | 10/1998 | Carter et al. |
| 5,837,234 A | 11/1998 | Gentile et al. |
| 5,840,523 A | 11/1998 | Simmons et al. |
| 5,869,046 A | 2/1999 | Presta et al. |
| 5,877,296 A | 3/1999 | Hamann et al. |
| 6,331,415 B1 | 12/2001 | Cabilly et al. |
| 6,824,780 B1 | 11/2004 | Devaux et al. |
| 7,112,439 B2 | 9/2006 | Johnson et al. |
| 2003/0130496 A1 | 7/2003 | Winter et al. |

FOREIGN PATENT DOCUMENTS

| DE | 266710 A | 8/1985 |
| EP | 183070 A2 | 6/1986 |
| EP | 244234 A2 | 11/1987 |
| EP | 404097 A2 | 12/1990 |

(Continued)

OTHER PUBLICATIONS

Sherry et al. 1986. J. Virology. 57:246-257.*
Lanzavecchia et al. 2007. Current Opin in Biotech. 18:523-528.*
"Human Rhinovirus Monoclonal Antibody." QED Bioscience Inc. Retrieved Nov. 7, 2012. http://www.qedbio.com/v/pdf/18758.pdf.
Altschul et al. "Basic Local Alignment Search Tool." *J. Mol. Biol.* 215.3(1990):403-410.
Altschul et al. "Gapped Blast and PSI-Blast: A New Generation of Protein Database Search Programs." *Nucl. Acids Res.* 25.17(1997):3389-3402.
Arnon et al. "Monoclonal Antibodies for Immunotargeting of Drugs in Cancer Therapy." *Monoclonal Antibodies and Cancer Therapy.* New York: Alan R. Liss, Inc. Reisfeld et al., eds. (1985):243-256.
ATCC Accession No. 12424, Retrieved Dec. 18, 2012.
ATCC Accession No. 16045, Retrieved Dec. 18, 2012.
ATCC Accession No. 24178, Retrieved Dec. 18, 2012.

(Continued)

Primary Examiner — Shulamith H Shafer

(57) ABSTRACT

The invention provides isolated fully human monoclonal anti-HRV antibodies, as well as method of making and using these antibodies. Anti-HRV antibodies of the invention prevent or treat subjects having HRV-infections, and related diseases, including, but not limited to, the common cold, nasopharyngitis, croup, pneumonia, bronchiolitis, asthma, chronic obstructive pulmonary disease (COPD), sinusitis, bacterial superinfection, and cystic fibrosis.

48 Claims, 4 Drawing Sheets

(56) References Cited

FOREIGN PATENT DOCUMENTS

| | | | |
|---|---|---|---|
| EP | 404226 A1 | 12/1990 |
| EP | 0425235 B1 | 5/1991 |
| WO | WO-8101145 A1 | 4/1981 |
| WO | WO-8807378 A1 | 10/1988 |
| WO | WO-9013646 A1 | 11/1990 |
| WO | WO-9100360 A1 | 1/1991 |
| WO | WO-9202551 A1 | 2/1992 |
| WO | WO-9220373 A1 | 11/1992 |
| WO | WO-9308829 A1 | 5/1993 |
| WO | WO-9311161 A1 | 6/1993 |
| WO | WO-9316185 A2 | 8/1993 |
| WO | WO-9321232 A1 | 10/1993 |
| WO | WO-9404690 A1 | 3/1994 |
| WO | WO-9425591 A1 | 11/1994 |
| WO | WO-9616673 A1 | 6/1996 |
| WO | WO-9717852 A1 | 5/1997 |
| WO | WO-9738731 A1 | 10/1997 |
| WO | WO-9802463 A1 | 1/1998 |
| WO | WO-2004076677 A2 | 9/2004 |

OTHER PUBLICATIONS

ATCC Accession No. 27325, Retrieved Dec. 18, 2012.
ATCC Accession No. 31446, Retrieved Dec. 18, 2012.
ATCC Accession No. 31537 retrieved Aug. 15, 2011.
ATCC Accession No. 36906, Retrieved Dec. 18, 2012.
ATCC Accession No. 56500, Retrieved Dec. 18, 2012.
ATCC Accession No. CCL-10, Retrieved Dec. 18, 2012.
ATCC Accession No. CCL-2, Retrieved Dec. 18, 2012.
ATCC Accession No. CCL-34, Retrieved Dec. 18, 2012.
ATCC Accession No. CCL-51, Retrieved Dec. 18, 2012.
ATCC Accession No. CCL-70, Retrieved Dec. 18, 2012.
ATCC Accession No. CCL-75, Retrieved Dec. 18, 2012.
ATCC Accession No. CRL-1442, Retrieved Dec. 18, 2012.
ATCC Accession No. CRL-1587, Retrieved Dec. 18, 2012.
ATCC Accession No. CRL-1651, Retrieved Dec. 18, 2012.
ATCC Accession No. HB-8065, Retrieved Dec. 18, 2012.
Babcook et al. "A Novel Strategy for Generating Monoclonal Antibodies From Single, Isolated Lymphocytes Producing Antibodies of Defined Specificities." *PNAS.* 93.15(1996):7843-7848.
Bird et al. "Single-Chain Antigen-Binding Proteins." *Science.* 242(1988):423-426.
Bitter et al. "Expression and Secretion Vectors for Yeast." *Meth. Enzymol.* 153(1987):516-544.
Bolton et al. "The Labelling of Proteins to High Specific Radioactives by Conjugation to a 125I-Containing Acylating Agent." *Biochem. J.* 133.3(1973):529-538.
Brennan et al. "Preparation of Bispecific Antibodies by Chemical Recombination of Monoclonal Immunoglobulin G1 Fragments." *Science.* 229(1985):81-83.
Broglie et al. "Light-Regulated Expression of a Pea Ribulose-1,5-Bisphosphate Carboxylase Small Subunit Gene in Transformed Plant Cells." *Science.* 224(1984):838-843.
Brüggemann et al. "Designer Mice: The Production of Human Antibody Repertoires in Transgenic Animals." *The Year in Immunology: Generation of Antibodies by Cell and Gene Immortalization.* Terhorst et al., eds. New York: Karger. 7(1993):33-40.
Buchacher et al. "Generation of Human Monoclonal Antibodies Against HIV-1 Proteins; Electrofusion and Epstein-Barr Virus Transformation for Peripheral Blood Lymphocyte Immortalization." *AIDS Res. Hum. Retroviruses.* 10.4(1994):359-369.
Capel et al. "Heterogeneity of Human IgC Receptors." *Immunometh.* 4.1(1994):25-34.
Carlsson et al. "Protein Thiolating and Reversible Protein-Protein Conjugation." *Biochem. J.* 173(1978):723-737.
Caron et al. "Engineered Humanized Dimeric Forms of IgC are More Effective Antibodies." *J. Exp. Med.* 176(1992):1191-1195.
Carter et al. "High Level *Escherichia coil* Expression and Production of a Bivalent Humanized Antibody Fragment." *Bio/Technology.* 10(1992):163-167.

Casadevall. "Antibodies for Defencse Against Biological Attack." *Nat. Biotech.* 20(2002):114.
Chari et al. "Immunoconjugates Containing Novel Maytansinoids: Promising Anticancer Drugs." Cancer Res. 52(1992):127-131.
Chothia et al. "Canonical Structures for the Hypervariable Regions of Immunoglobulins." *J. Mol. Biol.* 196.4(1987):901-917.
Clackson et al. "Making Antibody Fragments Using Phage Display Libraries." *Nature.* 352(1991):624-628.
Clynes et al. "Fc Receptors are Required in Passive and Active Immunity to Melanoma." *PNAS.* 95.2(1998):652-656.
Colbére-Garapin et al. "A New Dominant Hybrid Selective Marker for Higher Eukoaryotic Cells." *J. Mol. Biol.* 150.1(1981):1-14.
Coruzzi et al. "Tissue-Specific and Light-Regulated Expression of a Pea Nuclear Gene Encoding the Small Subunit of Ribulose-1,5-bisphosphate Carboxylase." *EMBO J.* 3.8(1984):1671-1679.
Cunningham et al. "High-Resolution Epitope Mapping of hGH-Receptor Interactions by Alanine-Scanning Mutagenesis." *Science.* 244(1989):1081-1085.
Dayhoff et al. "A Model of Evolutionary Change in Proteins." *Atlas of Protein Sequence and Structure.* Washington, D.C.: National Biomedical Research Foundation. Dayhoff, ed. 5.S3(1978):345-358.
Daëron. "Fc Receptor Biology." *Annu. Rev. Immunol.* 15(1997):203-234.
de Haas et al. "Fc Gamma Receptors of Phagocytes." *J. Lab. Clin. Med.* 126.4(1995):330-341.
Edlmayr et al. "Antibodies Induced with Recombinant VP1 From Human Rhinovirus Exhibit Cross-Neutralisation." *Eur. Respir. J.* 37(2011):44-52.
Engelhard et al. "The Insect Tracheal System: A Conduit for the Systemic Spread of *Autographa californica* M Nuclear Polyhedrosis Virus." *PNAS.* 91.8(1994):3224-3227.
Eppstein et al. "Biological Activity of Liposome-Encapsulated Murine Interferon Gamma is Mediated by a Cell Membrane Receptor." *PNAS.* 82.11(1985):3688-3692.
Gabizon et al. "Pharmacokinetics and Tissue Distribution of Doxorubicin Encapsulated in Stable Liposome with Long Circulation Times." *J. Natl. Cancer Inst.* 81.19(1989):1484-1488.
Gazzano-Santoro et al. "A Non-Radioactive Complement-Dependent Cytotoxicity Assay for Anti-CD20 Monoclonal Antibody." *J. ImmunoL Meth.* 202.2(1997):163-171.
Graham et al. "Characteristics of a Human Cell Line Transformed by DNA from Human Adenovirus Type 5." *J. Virol.* 36(1977):59-72.
Gruber et al. "Efficient Tumor Cell Lysis Mediated by a Bispecific Single Chain Antibody Expressed in *Escherichia coli*." *J. Immuno.* 152(1994):5368-5374.
Guss et al. "Structure of the IgG-Binding Regions of *Streptococcal* Protein G." *EMBO J.* 5.7(1986):1567-1575.
Guyer et al. "Immunoglobulin Binding by Mouse Intestinal Epithelial Cell Receptors." *J. Immunol.* 117.2(1976):587-593.
Harding et al. "The Immunogenicity of Humanized and Fully Human Antibodies." *MABS.* 2.3(2010):256-265.
Hartman et al. "Two Dominant-Acting Selectable Markers for Gene Transfer Studies in Mammalian Cells." *PNAS.* 85.21(1988):8047-8051.
Hein. "Unified Approach to Alignment and Phylogenes." *Meth. Enzymol.* 183(1990):626-645.
Hellström et al. "Antibodies for Drug Delivery." *Controlled Drug Delivery.* New York: Marcel Dekker, Inc. Robinson et al., eds. 2nd ed. (1987):623-653.
Henikoff et al. "Amino Acid Substitution Matrices from Protein Blocks." *PNAS.* 89(1992):10915-10919.
Higgins et al. "Fast and Sensitive Multiple Sequence Alignments on a Microcomputer." *CABIOS.* 5.2(1989):151-153.
Hobbs et al. "Genetic Engineering." *McGraw Hill Yearbook of Science and Technology.* New York: McGraw Hill. (1992):189-196.
Holliger et al. "'Diabodies': Small Bivalent and Bispecific Antibody Fragments." *PNAS.* 90.14(1993):6444-6448.
Honegger et al. "Yet Another Numbering Scheme for Immunoglobulin Variable Domains: An Automatic Modeling and Analysis Tool." *J. Mol. Biol.* 309.3(2001):657-670.
Hwang et al. "Hepatic Uptake and Degradation of Unilamellar Spingomyelin/Cholesterol Liposomes: A Kinetic Study." *PNAS.* 77.7(1980):4030-4034.

(56) References Cited

OTHER PUBLICATIONS

Igarashi et al. "Human Immunodeficiency Virus Type 1 Neutralizing Antibodies Accelerate Clearance of Cell-Free Virions From Blood Plasma." *Nat. Med.* 5.2(1999):211-216.
Jakobovits et al. "Analysis of Homozygous Mutant Chimeric Mice: Deletion of the Immunoglobulin Heavy-Chain Joining Region Blocks B-Cell Development and Antibody Production." *PNAS.* 90.6(1993):2551-2555.
Jakobovits et al. "Germ-Line Transmission and Expression of a Human-Derived Yeast Artificial Chromosome." *Nature.* 362(1993):255-258.
Jones et al. "Replacing the Complementarity-Determing Regions in a Human Antibody With Those From a Mouse." *Nature.* 321(1986):522-525.
Jurgeit et al. "An RNA Replication-Center Assay for High Content Image-Based Quantifications of Human Rhinovirus and Coxsackievirus Infections." *Virol. J.* 7.1(2010):264.
Kabat et al. Sequences of Proteins of Immunological Interest, 5th edit. NIH Publication No. 91-3242 U.S. Dept of Health & Human Services (1991): iii-xcvi, 2130-2180.
Karpas et al. "A Human Myeloma Cell Line Suitable for the Generation of Human Monoclonal Antibodies." *PNAS.* 98.4(2001):1799-1804.
Keller et al. "Passive Immunity in Prevention and Treatment of Infectious Diseases." *Clin. Microbiol. Rev.* 13.4(2000):602-614.
Kim et al. "Localization of the Site of the Murine IgG1 Molecule That is Involved in Binding to the Murine Intestinal Fc Receptor." *Eur. J. Immunol.* 24(1994):2429-2434.
Kostelny et al. "Formation of a Bispecific Antibody by the Use of Leucine Zippers." *J. Immunol* 148.5(1992):1547-1553.
Kroll et al. "A Multifunctional Prokaryotic Protein Expression System: Overproduction, Affinity Purification and Selective Detection." *DNA Cell Biol.* 12(1993):441-453.
Kyte et al. "A Simple Method for Displaying the Hydropathic Character of a Protein." *J. Mol. Biol.* 157.1(1982):105-132.
Köhler et al. "Continuous Cultures of Fused Cells Secreting Antibody of Predefined Specificity." *Nature.* 256(1975):495-497.
Lefranc et al. "IMGT Unique Numbering for Immunoglobulin and T Cell Receptor Variable Regions and Ig Superfamily V-Like Domains." *Dev. Comp. Immunol.* 27.1(2003):55-77.
Lefranc et al. "IMGT, The International ImMunoGeneTics Database." *Nucl. Acids Res.* 27.1(1999):209-212.
Lefranc. "The IMGT Unique Numbering for Immunoglobulins, T Cell Receptors and Ig-Like Domains." *Immunologist.* 7(1999):132-136.
Lefranc. "Unique Database Numbering System for Immunogenetic Analysis." *ImmunoL Today.* 18.1 1(1997):509.
Lindmark et al. "Binding of Immunoglobulins to Protein A and Immunoglobulin Levels in *Mammalian* sera." *J. ImmunoL Meth.* 62.10(1983):1-13.
Liu et al. "Eradication of Large Colon Tumor Xenografts by Targeted Delivery of Maytansinoids." *PNAS.* 93.16(1996):8618-8623.
Logan et al. "Adenovirus Tripartite Leader Sequence Enhances Translation of mRNAs Late After Infection." *PNAS.* 81.12(1984):3655-3659.
Lowy et al. "Isolation of Transforming DNA: Cloning the Hamster aprt Gene." *Cell.* 22.3(1980):817-823.
Maddox et al. "Elevated Serum Levels in Human Pregnancy of a Molecule Immunochemically Similar to Eosinophil Granule Major Basic Protein." *J. Exp. Med.* 158(1983):1211-1226.
Marks et al. "By-Passing Immunization: Human Antibodies from V-Gene Libraries Displayed on Phage." *J. Mol. Biol.* 222.3(1991):581-597.
Martin et al. "Irreversible Coupling of Immunoglobulin Fragments to Preformed Vesicles." *J. Biol. Chem.* 257.1(1982):286-288.
Massey. "Catalytic Antibodies Catching On." *Nature.* 328(1987):457-458.
Mather et al. "Culture of Testicular Cells in Hormone-Supplemented Serum-Free Medium." *Ann. N. Y. Acad. Sci.* 383(1982):44-68.
Mather. "Establishment and Characterization of Two Distince Mouse Testicular Epithelial Cell Lines." *Biol. Reprod.* 23.1(1980):243-252.
Milstein et al. "Hybrid Hybridomas and Their Use in Immunohistochemistry." *Nature.* 305(1983):537-540.
Morimoto et al. "Single-Step Purification of F(ab')2 Fragments of Mouse Monoclonal Antibodies (Immunoglobulins G1) by Hydrophobic Interaction High Performance Liquid Chromatography using TSKgel Phenyl-5PW." *J. Biochem. Biophys. Methods.* 24.1-2(1992):107-117.
Morrison et al. "Chimeric Human Antibody Molecules: Mouse Antigen-Binding Domains with Human Constant Region Domains." *PNAS.* 81.21(1984):6851-6855.
Morrison. "The Determination of the Exposed Proteins on Membranes by the Use of Lactoperoxidase." *Meth. Enzymol.* 3(1974):103-109.
Murakami et al. "Cell Cycle Regulation, Oncogenes, and Antineoplastic Drugs." *The Molecular Basis of Cancer*. Mendelsohn et al., eds. Philadelphia: WB Saunders. (1995)1-17.
Myers et al. "Optimal Alignments in Linear Space." *CABIOS.* 4.1(1988):11-17.
Needleman et al. "A General Method Applicable to the Search for Similarities in the Amino Acid Sequence of Two Proteins." *J. Moi. Biol.* 48.3(1970):443-453.
Neuberger et al. "Recombinant Antibodies Possessing Novel Effctor Functions." *Nature.* 312(1984):604-608.
Order. "Analysis, Results and Future Prospective of the Therapeutic Use of Radiolabeled Antibody in Cancer Therapy." *Monoclonal Antibodies for Cancer Detection and Therapy*.Waltham, MA: Academic Press. Baldwin et al, eds. (1985):303-316.
Pearson et al. "Improved Tools for Biological Sequence Comparison." *PNAS.* 85(1988):2444-2448.
Plückthun et al. "Expression of Functional Antibody Fv and Fab Fragments in *Escherichia coli*." *Meth. Enzymol.* 178(1989):497-515.
Plückthun. "Antibodies from *Escherichia coli*." *The Pharmacology of Monoclonal Activities*. Rosenburg et al., eds. New York: Springer-Verlag. 113(1994):269-315.
Porath. "Immobilized Metal Ion Affinity Chromatography." *Prot. Exp. Purif.* 3.4(1992):263-281.
Presta. "Antibody Engineering." *Curr. Op. Struct. Biol.* 2.4(1992):593-596.
Ravetch et al. "Fc Receptors." *Annu. Rev. Immunol.* 9(1991):457-492.
Rhodes et al. "Transformation of Maize by Electroporation of Embryos." *Methods Mol. Biol.* 55(1995):121-131.
Riechmann et al. "Reshaping Human Antibodies for Therapy." *Nature.* 332(1988):323-327.
Robinson. "Comparison of Label Tree with Valency Three." *J. Combin. Ther. Ser. B.* 11(1971):105-119.
Ruiz et al. "IMGT, The International ImMunoGeneTics Database." *Nucl. Acids Res.* 28.1(2000):219-221.
Saitou et al. "The Neighbor-joining Method: A New Method for Reconstructing Phylogenetic Trees." *Mol. Biol. Evol.* 4.4(1987):406-425.
Sanger et al. "DNA Sequencing With Chain-Terminating Inhibitors." *PNAS.* 74.12(1977):5463-5467.
Scatchard. "The Attractions of Proteins for Small Molecules and Ions." *Ann. N. Y. Acad. Sci.* 51(1949):660-672.
Shalaby et al. "Development of Humanized Bispecific Antibodies Reactive with Cytotoxic Lumphocytes and Tumor Cells Overexpressing the *HER2* Protooncogene." *J. Exp. Med.* 175(1992):217-225.
Shibata et al. "Neutralizing Antibody Directed Against the HIV-1 Envelope Glycoprotein Can Completely Block HIV-1/SIV Chimeric Virus Infections of Macaque Monkeys." *Nat. Med.* 5(1999):204-210.
Shopes. "A Genetically Engineered Human IgC Mutant with Enhanced Cytolytic Activity." *J. Immunol.* 148.9(1992):2918-2922.
Smith et al. "Comparison of Biosequences." *Adv. Appl. Math.* 2.4(1981):482-489.
Stevenson et al. "A Chimeric Antibody with Dual Fc Receptor Regions (bisFabFc) Prepared b Manipulations at the IgG Hinge." *Anti-Cancer Drug Des.* 2(10989):219-230.
Stites et al., ed. *Basic and Clinical Immunology*. Norwalk, CT: Appleton & Lange. 8(1994):71.

(56) References Cited

OTHER PUBLICATIONS

Suresh et al. "Bispecific Monoclonal Antibodies from Hybrid Hybridomas." *Meth. Enzymol.* 121(1986):210-228.
Syvanen et al. "Preparation of 125l-Catalytic Subunit of Aspartate Transcarbamylase and Its Use in Studies of the Regulatory Subunit." *J. Biol. Chem.* 248(1973):3762-3768.
Takamatsu et al. "Expression of Bacterial Chloramphenicol Acetyltransferase Gene in Tobacco Plants Mediated by TMV-RNA." *EMBO J.* 6.2(1987):307-311.
Thorpe et al. "The Preparation and Cytotoxic Properties of Antibody-Toxin Conjugates." *Immunol. Rev.* 62(1982):119-158.
Thorpe. "Antibody Carriers of Cytotoxic Agents in Cancer Therapy: A Review." *Monoclonal Antibodies '84: Biological and Clinical Applications*. Milan, Italy: Editrice Kurtis. Pinchera et al, eds. (1985):475-506.
Traggai et al. "An Efficient Method to Make Human Monoclonal Antibodies From Memory B Cells: Potent Neutralization of SARS Coronavirus." *Nat. Med.* 10.8(2004):871-875.
Traunecker et al. "Bispecific Single Chain Molecules (Janusins) Target Cytotoxic Lumphocytes on HIV Infected Cells." *EMBO J.* 10.12(1991):3655-3659.
Tutt et al. "Trispecific F(ab')3 Derivatives that Use Cooperative Signaling via the TCR/CD3 Complex and CD2 to Activate and Redirect Resting Cytotoxic T Cells." *J. Immunol.* 147(1991):60-69.
Urlaub et al. "Isolation of Chinese Hamster Cell Mutants Deficient in Dihydrofolate Reductase Activity." *PNAS.* 77.7(1980):4216-4220.
Van Heeke et al. "Expression of Human Asparagine Synthetase in *Escherichia coli*." *J. Biol. Chem.* 264.10(1989):5503-5509.
Verhoeyen et al. "Reshaping Human Antibodies: Grafting an Antilysozyme Activity." *Science.* 239(1988):1534-1536.
Vitetta et al. "Redesigning Nature's Poisons to Create Anti-Tumor Reagents." *Science.* 238(1987):1098-1104.
Wang et al. "Capside Structure and Dynamics of a Human Rhinovirus Probed by Hydrogen Exchange Mass Spectrometry." *Prot. Sci.* 14.6(2005):1661-1672.
Weitkamp et al. "Infant and Adult Human B Cell Responses to Rotavirus Share Common Immunodominant Variable Gene Repertoires." *J. Immunol.* 171.9(2003):4680-4688.
Wigler et al. "Transfer of Purified Herpes Virus Thymidine Kinase Gene to Cultured Mouse Cells." *Cell.* 11.1(1977):223-232.
Wigler et al. "Transformation of Mammalian Cells with an Amplifiable Dominant-Acting Gene." *PNAS.* 77.6(1980):3567-3570.
Wilbur et al. "Rapid Similarity Searches of Nucleic Acid and Protein Data Banks." *PNAS.* 80.3(1983):726-730.
Winter et al. "The Expression of Heat Shock Protein and Cognate Genes During Plant Development." *Results Probl. Cell Differ.* 17(1991):85-105.
Wolff et al. "Monoclonal Antibody Homodimers: Enhanced Antitumor Activity in Nude Mice." *Cancer Res.* 53(1993):2560-2565.
Yaniv. "Enhancing Elements for Activation of Eukaryotic Promoters." *Nature.* 297(1982):17-18.
Zapata et al. "Engineering Linear F(ab')2 Fragments for Efficient Production in *Escherichia coli* and Enhanced Antiproliferative Activity." *Protein Eng.* 8.10(1995):1057-1062.

\* cited by examiner

IC50 of Neutralization

FIG. 1

% Virus Serotypes Neutralized by 1 or 2 mAbs

Total 38 serotypes

| % | H17 | L22 | F16 |
|---|---|---|---|
| H17 | 45 | 47 | 53 |
| L22 | | 40 | 47 |
| F16 | | | 40 |

22 Clade A Major group

| % | H17 | L22 | F16 |
|---|---|---|---|
| H17 | 73 | 77 | 82 |
| L22 | | 68 | 77 |
| F16 | | | 64 |

FIG. 2A                FIG. 2B

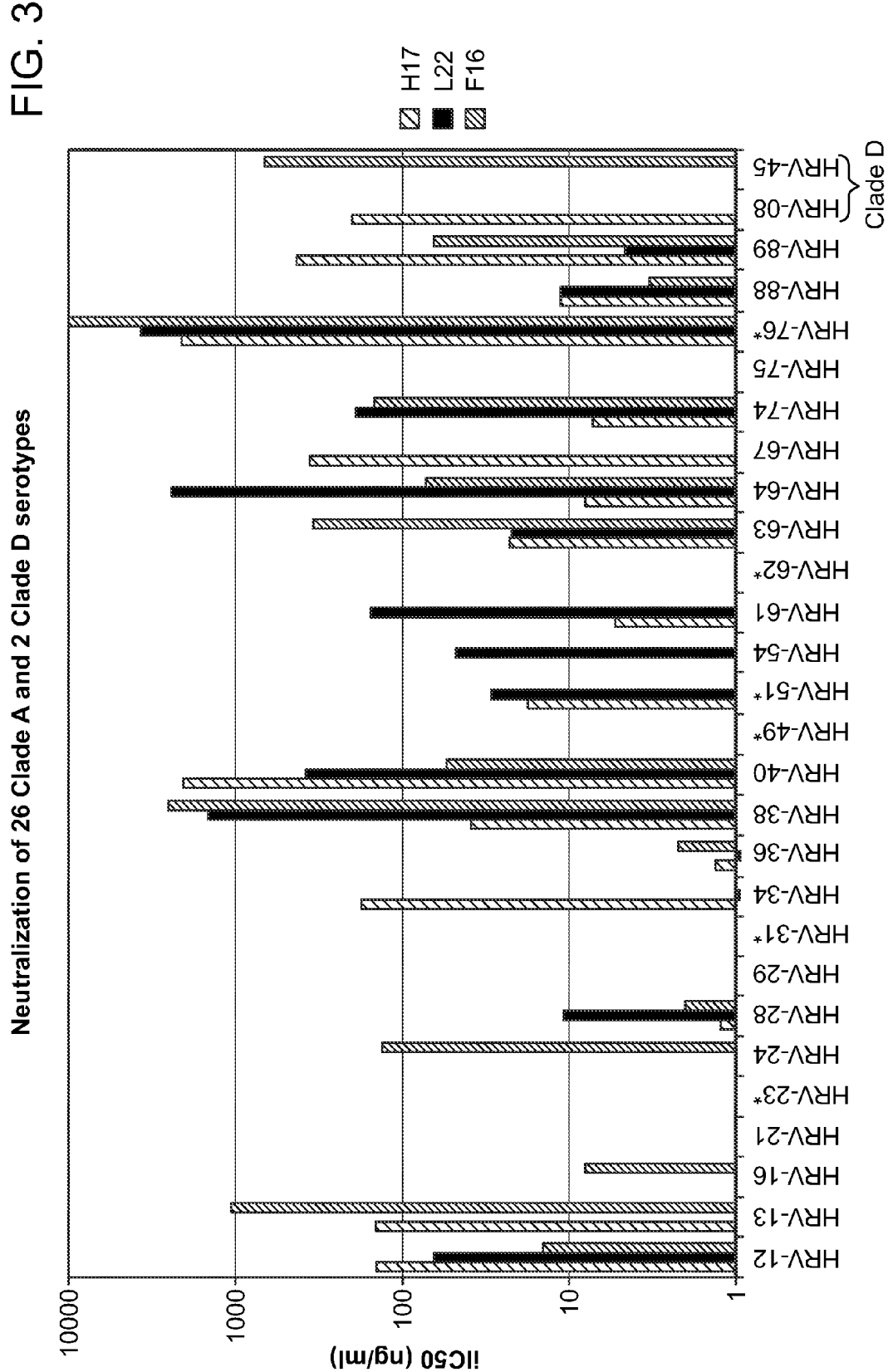

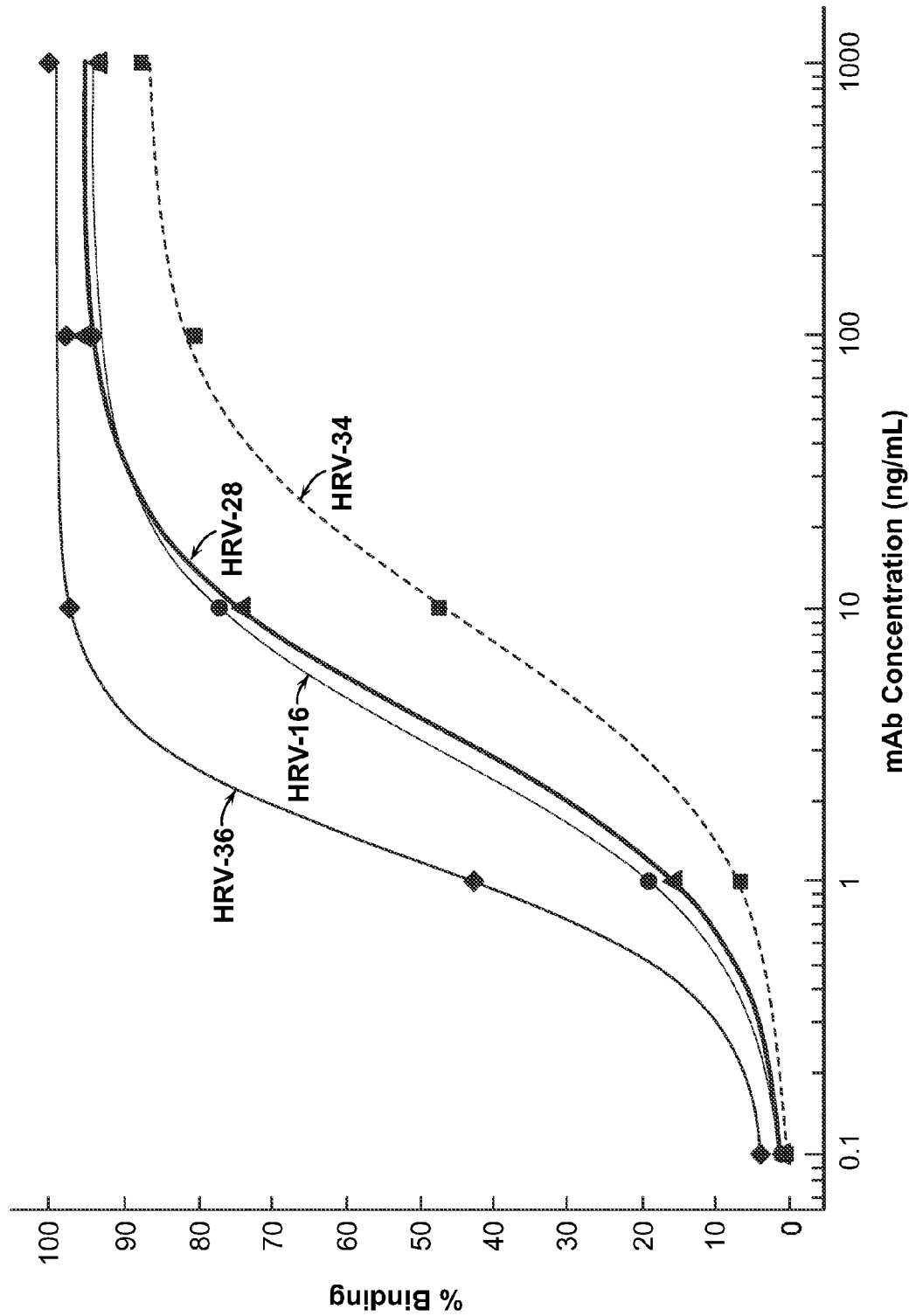

HUMAN RHINOVIRUS (HRV) ANTIBODIES

RELATED APPLICATIONS

This application claims the benefit of provisional application U.S. Ser. No. 61/529,008, filed on Aug. 30, 2011, the contents which are herein incorporated by reference in their entirety.

INCORPORATION OF SEQUENCE LISTING

The contents of the text file named "37418-519001US_ST25.txt," which was created on Aug. 23, 2012 and is 54 KB in size, are hereby incorporated by reference in their entirety.

FIELD OF THE INVENTION

The present invention relates generally to prophylaxis, therapy, diagnosis and monitoring of human rhinovirus (HRV) infection. The invention is more specifically related to human neutralizing monoclonal antibodies specific for HRV, such as broad and potent neutralizing monoclonal antibodies specific for HRV and their manufacture and use. Broad neutralization suggests that the antibodies can neutralize HRV isolates from multiple isotypes.

BACKGROUND OF THE INVENTION

Human rhinoviruses are the most common infectious agents in humans, worldwide. These viruses are also most commonly known as the primary cause of the common cold. Commensurate with their role as instigating colds, the primary route of entry for human rhinovirus is the upper respiratory tract. These viruses travel rapidly throughout the local population because they are transmitted through air, e.g. via contaminated respiratory droplets of sneezes and coughs, via contact with contaminated surfaces, and via person-to-person contact. Infection also occurs rapidly. The virus adheres to cell surface receptors within minutes of entering the respiratory tract. Symptoms appear in most individuals within days. However, the incubation time can vary from approximately 12 hours to a week.

Infection by human rhinovirus can be fatal; however, more common symptoms include, but are not limited to sore throat, runny nose, nasal congestion, sneezing, cough, muscle aches, fatigue, malaise, headache, muscle weakness, and loss of appetite. Infections frequently occur during the time of year when people spend most time indoors and, therefore, spend most time in close proximity to one another, e.g. from September to April. The consequences of the human rhinovirus infection are not only medical, but economical. Students and employees must isolate themselves from school and colleagues to prevent spread of the virus, which results in lost educational opportunity and productivity.

Despite a long-felt need in the art and ongoing attempts to cure infections caused by the human rhinovirus, including the common cold, a need still exists for an effective treatment that addresses the underlying cause of these illnesses by neutralizing the virus itself.

SUMMARY OF THE INVENTION

The invention solves this long-felt need by providing compositions and methods for preventing and treating human rhinovirus infection.

The present invention provides a novel method for isolating potent, broadly neutralizing monoclonal antibodies against HRV. Peripheral Blood Mononuclear Cells (PBMCs) are obtained from a donor selected for HRV neutralizing activity in the plasma, and memory B cells are isolated for culture in vitro. The B cell culture supernatants are then screened by a primary neutralization assay in a high throughput format, and B cell cultures exhibiting neutralizing activity are selected for rescue of monoclonal antibodies. It is surprisingly observed that neutralizing antibodies obtained by this method do not always exhibit epitope- or viral-binding at levels that correlate with neutralization activity. The method of the invention therefore allows identification of novel antibodies with cross-isotype neutralization properties.

Specifically, the invention provides an isolated fully human monoclonal antibody, wherein the monoclonal antibody has the following characteristics a) binds to an epitope on the rhinovirus capsid protein selected from the group consisting of VP1, VP2, VP3, and VP4; b) binds to rhinovirus inside infected cells; and c) binds to rhinovirus. Alternatively, or in addition, the antibody binds to an epitope comprising a portion of two or more rhinovirus capsid proteins selected from the group consisting of VP1, VP2, VP3, and VP4. In a preferred embodiment, the epitope is non-linear. The antibody is isolated from a B-cell from a human donor.

In one aspect, the antibody binds to or cross-neutralizes rhinovirus serotypes from one or more clades selected from the group consisting of clade A (major group), clade A (minor group), clade B, and clade D. Alternatively, the antibody binds to or cross-neutralizes rhinovirus serotypes from two or more or three or more clades selected from the group consisting of clade A (major group), clade A (minor group), clade B, and clade D. In another aspect, the antibody binds to at least 40%, 45%, 50%, 55%, 60%, 65%, 70%, 75%, 80%, 85%, 90%, 95%, or 100% of HRV serotypes selected from the group consisting of HRV-12, HRV-13, HRV-16, HRV-21, HRV-23, HRV-24, HRV-28, HRV-34, HRV-36, HRV-38, HRV-40, HRV-51, HRV-54, HRV-61, HRV-63, HRV-64, HRV-67, HRV-74, HRV-75, HRV-76, HRV-88, HRV-89, HRV-29, HRV-31, HRV-49, HRV-62, HRV-14, HRV-26, HRV-37, HRV-48, HRV-52, HRV-70, HRV-83, HRV-84, HRV-86, HRV-93, HRV-08, and HRV-45. Preferably, the antibody binds to at least 90% of these HRV serotypes. Alternatively, or in addition, the antibody neutralizes at least 40%, 45%, 50%, 55%, 60%, 65%, 70%, 75%, 80%, 85%, 90%, 95%, or 100% of HRV serotypes HRV serotypes selected from the group consisting of HRV-12, HRV-13, HRV-16, HRV-21, HRV-23, HRV-24, HRV-28, HRV-34, HRV-36, HRV-38, HRV-40, HRV-51, HRV-54, HRV-61, HRV-63, HRV-64, HRV-67, HRV-74, HRV-75, HRV-76, HRV-88, HRV-89, HRV-29, HRV-31, HRV-49, HRV-62, HRV-14, HRV-26, HRV-37, HRV-48, HRV-52, HRV-70, HRV-83, HRV-84, HRV-86, HRV-93, HRV-08, and HRV-45. Preferably, the antibody neutralizes at least 40% of these HRV serotypes. Furthermore, the antibody neutralizes the HRV serotypes with a median $IC_{50}$ value of equal to or less than 100 ng/mL.

Optionally, the antibody is TCN-711 (6893_E11), TCN-716 (6362_F16), TCN-717 (6358_H17), or TCN-722 (6385_L22). The isolated fully human monoclonal antibody that binds to or neutralizes HRV, comprises, (a) a $V_H$ CDR1 region comprising the amino acid sequence of DFYWT (SEQ ID NO: 5); a $V_H$ CDR2 region comprising the amino acid sequence of EIDRDGATYYNPSLKS (SEQ ID NO: 6); a $V_H$ CDR3 region comprising the amino acid sequence of RPM-LRGVWGNFRSNWFDP (SEQ ID NO: 7); a $V_L$ CDR1 region comprising the amino acid sequence of SGSSSNI- GYSYVS (SEQ ID NO: 14); a $V_L$ CDR2 region comprising the amino acid sequence of ENNKRPS (SEQ ID NO: 15); and a $V_L$ CDR3 region comprising the amino acid sequence of GTWDTRLFGGV (SEQ ID NO: 16); (b) a $V_H$ CDR1 region comprising the amino acid sequence of DFAMH (SEQ ID NO: 21); a $V_H$ CDR2 region comprising the amino acid sequence of SISRDGSTKYSGDSVKG (SEQ ID NO: 22); a $V_H$ CDR3 region comprising the amino acid sequence of DSPYYLDIVGYRYFHHYGMDV (SEQ ID NO: 23); a $V_L$ CDR1 region comprising the amino acid sequence of RASQILHSYNLA (SEQ ID NO: 30); a $V_L$ CDR2 region comprising the amino acid sequence of GAYNRAS (SEQ ID NO: 31); and a $V_L$ CDR3 region comprising the amino acid sequence of QQYGDSPSPGLT (SEQ ID NO: 32); (c) a $V_H$ CDR1 region comprising the amino acid sequence of QNDYHWA (SEQ ID NO: 37); a $V_H$ CDR2 region comprising the amino acid sequence of SVHYRQKSYYSPSLKS (SEQ ID NO: 38); a $V_H$ CDR3 region comprising the amino acid sequence of HNREDYYDSNAYFDE (SEQ ID NO: 39); a $V_L$ CDR1 region comprising the amino acid sequence of SGDDLENTLVC (SEQ ID NO: 46); a $V_L$ CDR2 region comprising the amino acid sequence of QDSKRPS (SEQ ID NO: 47); and a $V_L$ CDR3 region comprising the amino acid sequence of QTWHRSTAQYV (SEQ ID NO: 48); or (d) a $V_H$ CDR1 region comprising the amino acid sequence of SNDQYWA (SEQ ID NO: 53); a $V_H$ CDR2 region comprising the amino acid sequence of SVHYRRRNYYSPSLES (SEQ ID NO: 54); a $V_H$ CDR3 region comprising the amino acid sequence of HNWEDYYESNAYFDY (SEQ ID NO: 55); a $V_L$ CDR1 region comprising the amino acid sequence of SGDQLENTFVC (SEQ ID NO: 62); a $V_L$ CDR2 region comprising the amino acid sequence of QGSKRPS (SEQ ID NO: 63); and a $V_L$ CDR3 region comprising the amino acid sequence of QAWDRSTAHYV (SEQ ID NO: 64).

Alternatively, the antibody binds to the same epitope as TCN-711 (6893_E11), TCN-716 (6362_F16), TCN-717 (6358_H17), or TCN-722 (6385_L22). Alternatively stated, the invention provides an antibody that binds the same epitope as an antibody comprising, (a) a $V_H$ CDR1 region comprising the amino acid sequence of DFYWT (SEQ ID NO: 5); a $V_H$ CDR2 region comprising the amino acid sequence of EIDRDGATYYNPSLKS (SEQ ID NO: 6); a $V_H$ CDR3 region comprising the amino acid sequence of RPMLRGVWGNFRSNWFDP (SEQ ID NO: 7); a $V_L$ CDR1 region comprising the amino acid sequence of SGSSSNIGYSYVS (SEQ ID NO: 14); a $V_L$ CDR2 region comprising the amino acid sequence of ENNKRPS (SEQ ID NO: 15); and a $V_L$ CDR3 region comprising the amino acid sequence of GTWDTRLFGGV (SEQ ID NO: 16); (b) a $V_H$ CDR1 region comprising the amino acid sequence of DFAMH (SEQ ID NO: 21); a $V_H$ CDR2 region comprising the amino acid sequence of SISRDGSTKYSGDSVKG (SEQ ID NO: 22); a $V_H$ CDR3 region comprising the amino acid sequence of DSPYYLDIVGYRYFHHYGMDV (SEQ ID NO: 23); a $V_L$ CDR1 region comprising the amino acid sequence of RASQILHSYNLA (SEQ ID NO: 30); a $V_L$ CDR2 region comprising the amino acid sequence of GAYNRAS (SEQ ID NO: 31); and a $V_L$ CDR3 region comprising the amino acid sequence of QQYGDSPSPGLT (SEQ ID NO: 32); (c) a $V_H$ CDR1 region comprising the amino acid sequence of QNDYHWA (SEQ ID NO: 37); a $V_H$ CDR2 region comprising the amino acid sequence of SVHYRQKSYYSPSLKS (SEQ ID NO: 38); a $V_H$ CDR3 region comprising the amino acid sequence of HNREDYYDSNAYFDE (SEQ ID NO: 39); a $V_L$ CDR1 region comprising the amino acid sequence of SGDDLENTLVC (SEQ ID NO: 46); a $V_L$ CDR2 region comprising the amino acid sequence of QDSKRPS (SEQ ID NO: 47); and a $V_L$ CDR3 region comprising the amino acid sequence of QTWHRSTAQYV (SEQ ID NO: 48); or (d) a $V_H$ CDR1 region comprising the amino acid sequence of SNDQYWA (SEQ ID NO: 53); a $V_H$ CDR2 region comprising the amino acid sequence of SVHYRRRNYYSPSLES (SEQ ID NO: 54); a $V_H$ CDR3 region comprising the amino acid sequence of HNWEDYYESNAYFDY (SEQ ID NO: 55); a $V_L$ CDR1 region comprising the amino acid sequence of SGDQLENTFVC (SEQ ID NO: 62); a $V_L$ CDR2 region comprising the amino acid sequence of QGSKRPS (SEQ ID NO: 63); and a $V_L$ CDR3 region comprising the amino acid sequence of QAWDRSTAHYV (SEQ ID NO: 64).

The invention provides an isolated anti-HRV antibody, wherein the antibody comprises, a $V_H$ CDR1 region comprising the amino acid sequence of DFYWT (SEQ ID NO: 5); a $V_H$ CDR2 region comprising the amino acid sequence of EIDRDGATYYNPSLKS (SEQ ID NO: 6); a $V_H$ CDR3 region comprising the amino acid sequence of RPMLRGVWGNFRSNWFDP (SEQ ID NO: 7); a $V_L$ CDR1 region comprising the amino acid sequence of SGSSSNIGYSYVS (SEQ ID NO: 14); a $V_L$ CDR2 region comprising the amino acid sequence of ENNKRPS (SEQ ID NO: 15); and a $V_L$ CDR3 region comprising the amino acid sequence of GTWDTRLFGGV (SEQ ID NO: 16).

The invention provides an isolated anti-HRV antibody, wherein said antibody comprises, a $V_H$ CDR1 region comprising the amino acid sequence of DFAMH (SEQ ID NO: 21); a $V_H$ CDR2 region comprising the amino acid sequence of SISRDGSTKYSGDSVKG (SEQ ID NO: 22); a $V_H$ CDR3 region comprising the amino acid sequence of DSPYYLDIVGYRYFHHYGMDV (SEQ ID NO: 23); a $V_L$ CDR1 region comprising the amino acid sequence of RASQILHSYNLA (SEQ ID NO: 30); a $V_L$ CDR2 region comprising the amino acid sequence of GAYNRAS (SEQ ID NO: 31); and a $V_L$ CDR3 region comprising the amino acid sequence of QQYGDSPSPGLT (SEQ ID NO: 32).

The invention provides an isolated anti-HRV antibody, wherein said antibody comprises, a $V_H$ CDR1 region comprising the amino acid sequence of QNDYHWA (SEQ ID NO: 37); a $V_H$ CDR2 region comprising the amino acid sequence of SVHYRQKSYYSPSLKS (SEQ ID NO: 38); a $V_H$ CDR3 region comprising the amino acid sequence of HNREDYYDSNAYFDE (SEQ ID NO: 39); a $V_L$ CDR1 region comprising the amino acid sequence of SGDDLENTLVC (SEQ ID NO: 46); a $V_L$ CDR2 region comprising the amino acid sequence of QDSKRPS (SEQ ID NO: 47); and a $V_L$ CDR3 region comprising the amino acid sequence of QTWHRSTAQYV (SEQ ID NO: 48).

The invention provides an isolated anti-HRV antibody, wherein said antibody comprises, a $V_H$ CDR1 region comprising the amino acid sequence of SNDQYWA (SEQ ID NO: 53); a $V_H$ CDR2 region comprising the amino acid sequence of SVHYRRRNYYSPSLES (SEQ ID NO: 54); a $V_H$ CDR3 region comprising the amino acid sequence of HNWEDYYESNAYFDY (SEQ ID NO: 55); a $V_L$ CDR1 region comprising the amino acid sequence of SGDQLENTFVC (SEQ ID NO: 62); a $V_L$ CDR2 region comprising the amino acid sequence of QGSKRPS (SEQ ID NO: 63); and a $V_L$ CDR3 region comprising the amino acid sequence of QAWDRSTAHYV (SEQ ID NO: 64).

The invention provides an isolated monoclonal anti-HRV antibody comprising, $_a$) a heavy chain sequence comprising the amino acid sequence of SEQ ID NO: 4 and a light chain sequence comprising amino acid sequence SEQ ID NO: 13, or b) a heavy chain sequence comprising the amino acid sequence of SEQ ID NO: 20 and a light chain sequence comprising amino acid sequence SEQ ID NO: 29, or c) a heavy chain sequence comprising the amino acid sequence of SEQ ID NO: 36 and a light chain sequence comprising amino acid sequence SEQ ID NO: 45, or d) a heavy chain sequence comprising the amino acid sequence of SEQ ID NO: 52 and a light chain sequence comprising amino acid sequence SEQ ID NO: 61.

The invention provides a nucleic acid molecule encoding an antibody described herein. The invention provides a vector comprising this nucleic acid molecule. The invention provides a cell comprising this vector.

The invention provides an isolated B cell clone or immortalized B-cell clone expressing an isolated monoclonal anti-HRV antibody described herein.

The invention provides an isolated epitope which binds to an isolated monoclonal anti-HRV antibody described herein. The invention further provides an immunogenic polypeptide or glycopeptide comprising this epitope.

The invention provides a composition comprising an isolated anti-HRV antibody described herein. Moreover, the invention provides a pharmaceutical composition comprising at least one isolated anti-HRV antibody described herein and a pharmaceutically acceptable carrier.

In certain embodiments, this composition or this pharmaceutical composition further comprise a second therapeutic agent. The second therapeutic agent is a second antibody, an antiviral drug, an antibiotic, a bronchodilator, a leukotriene blocker, a steroid, an antiinflammatory drug, or an oxygen therapy. The second antibody may be specific for human rhinovirus, influenza, parainfluenza, coronavirus, adenovirus, respiratory syncytical virus, picornavirus, metapneumovirus, or anti-IgE antibody. If the second antibody is specific for human rhinovirus, the antibody may be an anti-HRV antibody described herein.

The second therapeutic agent is an antiviral drug. The anti-viral drug may be an entry inhibitor, a fusion inhibitor, an integrase inhibitor, a nucleoside analog, a protease inhibitor, or a reverse transcriptase inhibitor. Exemplary anti-viral drug include, but are not limited to, Abacavir, Acicolvir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Immunovir, Idoxuridine, Imiquimod, Indinavir, Inosine, Interferon (Type I, II, or III), Interferon-alpha, Interferon-beta, Lamivudine, Lopinavir, Loviride, Maraviroc, Moroxydine, Methisazone, Nelfinavir, Nevirapine, Nexavir, Oseltamivir, Peginterferon alpha-2a, Pencicolvir, Peramivir, Pleconaril, Podophyllotoxin, Raltegravir, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, or Zidovudine.

The second therapeutic agent is an antibiotic. The antibiotic may be an Aminoglycoside, a Carbapenem, a Cephalosporin, a Lincosamide, a Macrolide, a Penicillin, or a Quinolone. Exemplary antibiotics include, but are not limited to, Amikacin, Gentamicin, Kanamycin, Neomycin, Netilmycin, Tobramycin, Paromycin, Geldanamycin, Ertapenem, Dorpenem, Imipenem/Cilastatin, Meropenem, Cefadroxil, Cefazolin, Cefalotin, Cefalothin, Cefalexin, Cefaclor, Ceamandole, Cefoxitin, Cefprozil, Cefurozime, Cefixime, Cefdinir, Defditoren, Cefoperazone, Cefotaxime, Cefazidime, Ceftibuten, Ceftizoxime, Ceftriaxone, Cefepime, Ceftobiprole, Teicoplanin, Vancomycin, Telavancin, Clindamycin, Lincomycin, Daptomycin, Azithromyzin, Clarithromycin, Dirithromycin, Erythromycin, Roxithromycin, Troleandomycin, Spectinomycin, Aztreonam, Furazolidone, Nitofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, Trimethoprim-Sulfamethoxazole (Cotrumoxazole), Demeclocycline, Docycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifampin, Rifabutin, Rifapentin, Stretomycin, Arsphenamine, Choramphenicol, Fosfomycin, Fusidic acid, Linezolid, Metonidazole, Mupirocin, Platensimycin, Quinupristin/Dalfopristin, Rifaximin, Thamphenicol, Tigecycline, Tinidazole.

The second therapeutic agent is a bronchodialator. In certain aspects, the bronchodilator is alternatively a short- or long-acting agent. Exemplary short-acting bronchodilators include, but are not limited to, a β2-agonist or an anticholinergic compound. Exemplary long-acting bronchodilators include, but are not limited to, a β2-agonist or a theophylline compound.

The second therapeutic agent is a leukotriene antagonist, inhibitor, or blocker. Leukotrienes are fatty compounds produced by the immune system that cause the inflammation found in, for example, the upper respiratory tract that results from genetic predisposition (e.g., asthma or allergy), viral infection (e.g., bronchitis or COPD), or lifestyle and environmental factors (e.g., smoking, mining, or exposure to asbestos). Regardless of the cause, leukotriene-mediated inflammation constricts airways. Accordingly, leukotriene inhibitors are often bronchodilators. Common leukotriene inhibitors (or modifiers) either inhibit the 5-lipoxygenase pathway (leukotriene synthase inhibitors) or antagonize cysteinyl-leukotriene type 1 receptors (leukotriene receptor antagonists or LTRAs). Leukotriene inhibitors, modifiers, or antagonists involved in either pathway are contemplated. Specifically, zileuton (Zyflo®) is a commercially-available drug that inhibits 5-lipoxygenase. Montelukast (Singulair®) and zafirlukast (Accolate®) are commercially-available leukotriene inhibitors that block the activity of cysteinyl leukotrienes at the CysLT1 receptor on target cells (e.g., bronchial smooth muscle).

The second therapeutic agent is a steroid. In a preferred embodiment, the steroid is a corticosteroid. Exemplary corticosteroids include, but are not limited to, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate.

The second therapeutic agent is an anti-inflammatory agent. Exemplary anti-inflammatory agents include, but are not limited to, antihistamines and histamine receptor blockers.

The second therapeutic agent is oxygen therapy. Oxygen therapy includes, but is not limited to, supplemental oxygen gas. In a preferred embodiment, the arterial blood oxygen saturation of the subject following the oxygen treatment is greater than or equal to 85%. In a more preferred embodiment, the arterial blood oxygen saturation of the subject following the oxygen treatment is greater than or equal to 90%.

The invention further provides a method of immunizing a subject against human rhinovirus (HRV) infection, comprising administering to the subject a composition or pharmaceutical composition described herein.

The invention provides a method of preventing or treating a human rhinovirus infection, comprising administering to a subject a composition or pharmaceutical composition described herein. In certain embodiments of this method, the human rhinovirus infection causes or exacerbates the common cold, nasopharyngitis, croup, pneumonia, bronchiolitis, asthma, chronic obstructive pulmonary disease (COPD), sinusitis, bacterial superinfection, or cystic fibrosis.

The invention provides a method of preventing or treating a human rhinovirus (HRV)-related disease, comprising administering to a subject a composition or pharmaceutical composition described herein. In certain embodiments of this method, the human rhinovirus (HRV)-related disease is the common cold, nasopharyngitis, croup, pneumonia, bronchiolitis, asthma, chronic obstructive pulmonary disease (COPD), sinusitis, bacterial superinfection, or cystic fibrosis.

In certain embodiment of these methods, a subject in need of immunization, prophylaxis, or treatment for HRV-infection includes any individual who comes into frequent, routine, close, and/or direct contact with another individual who is infected with HRV. Moreover, a subject in need of the methods of the invention is an individual who is at an increased risk of infection following exposure to HRV, e.g. premature infants, those infants who do not receive their mother's antibodies through breast milk, infants, children, immunocompromised individuals, malnourished individuals, those individuals with inflammatory disease (and, therefore, high cell surface expression ICAM-1, the receptor for HRV), those individuals without acquired immunity to HRV (e.g., no prior exposure to HRV), and those individuals who live in areas of high density (cities), poor nutrition, and/or poor sanitation. Furthermore, a subject having asthma, bacterial infection within the upper respiratory tract or chronic obstructive pulmonary disease (COPD), is particularly susceptible to infection by HRV, because the cells of the respiratory tract in these individuals express ICAM-1 at higher levels. Subjects typically develop COPD following exposure to noxious particles or gases, which most frequently take the form of cigarette smoke. Thus, smokers have an increased risk of infection from HRV following exposure to the virus.

The invention provides a vaccine comprising either an isolated anti-HRV antibody as described herein or the epitope to which an antibody described herein binds.

The invention provides a kit comprising either an isolated anti-HRV antibody as described herein or the epitope to which an antibody described herein binds.

Other features and advantages of the invention will be apparent from and are encompassed by the following detailed description and claims.

BRIEF DESCRIPTION OF THE DRAWINGS

FIG. 1 is a graph depicting the potency of neutralization versus human rhinovirus (HRV) serotypes. The potency of neutralization is as the IC50 value on the Y-axis, which was determined in a microneutralization assay. The cross bar in each serotype indicates the median IC50 value. Data are representative of two independent experiments with similar results.

FIG. 2A-B is a pair of tables indicating the relative breadth of neutralization by TCN-717 (H17), TCN-722 (L22) and TCN-716 (F16) antibodies. The relative breadth of neutralization of each antibody is expressed as the % of virus serotypes neutralized. The 22 viruses in the major group of clade A (right panel, B) are a subset within the 38 viruses shown in the left panel (A). Neutralization by a combination of 2 antibodies is also shown.

FIG. 3 is a graph depicting the neutralization profile of TCN-717 (H17), TCN-722 (L22), and TCN-716 (F16) antibodies among 22 clade A major group serotypes and two clade D serotypes, as determined by microneutralization assay. Asterisks indicate those serotypes that were analyzed in a cytopathic effects (CPE) assay.

FIG. 5 is a graph depicting binding of TCN-711 (E11) to four HRV serotypes in infected HeLa cells.

DETAILED DESCRIPTION OF THE INVENTION

Figure 4A:
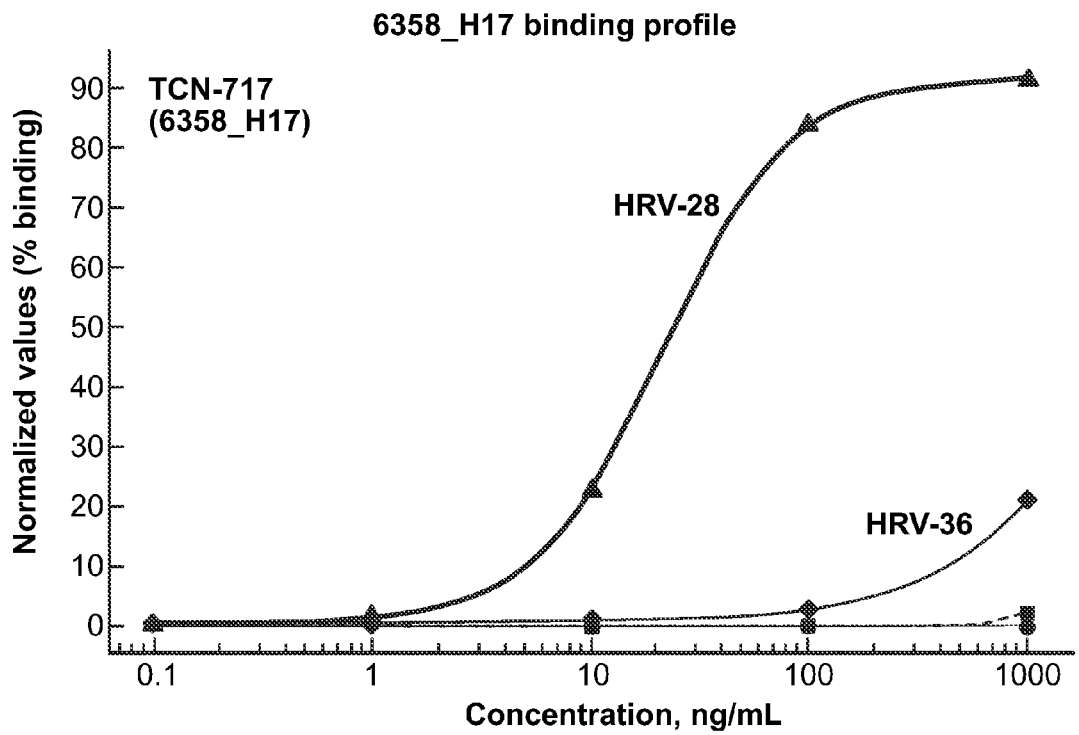
FIG. 4A-B is a pair of graphs depicting the direct binding of TCN-717 (H17) (A) and TCN-722 (L22) (B) to inactivated HRV virions in ELISA.

Human Rhinoviruses (HRVs) are small, nonenveloped viruses that contain a single-strand RNA genome within an icosahedral capsid. Over 100 serotypes of the virus have been identified (i.e. approximately 101 serotypes). Rhinoviruses belong to the Picornaviridae family.

The primary route of entry for human rhinovirus is the upper respiratory tract, and, specifically, the nasal mucosa, mouth, and eyes. Infection also occurs locally; confined to the upper respiratory tract by the temperature and pH sensitivity of the virus. The optimal temperature for rhinovirus replication is 33-35° C., and, thus, the virus does not efficiently replicate at body temperature. There is usually no gastrointestinal involvement because the virus is unstable in such acidic conditions. Consequently, rhinovirus does not spread from the respiratory tract.

Rhinoviruses travel rapidly throughout the local population because they are transmitted through air, e.g. via contaminated respiratory droplets of sneezes and coughs, via contact with contaminated surfaces, and via person-to-person contact. Infection also occurs rapidly.

The virus adheres to cell surface receptors of cells within the respiratory epithelium within minutes of entering the respiratory tract. The major receptor for the human rhinovirus is intercellular adhesion molecule-1 (ICAM-1). The virus uses the ICAM-1 receptor for both attachment and for uncoating. Because some HRV serotypes are capable of increasing the endogenous expression of ICAM-1 within infected cells, and, therefore, increasing the individual's susceptibility to infection, agents that inhibit up-regulation, block translation, increase degradation, or prohibit HRV attachment to ICAM-1 are therapeutic targets. Such targets are contemplated for use in combination with the anti-HRV antibodies of the invention.

Rhinoviruses are positive strand RNA viruses with a naked nucleocapsid. Positive-sense viral RNA is similar to mRNA, and, therefore, the single-stranded RNA genome of HRV can be immediately translated by the host cell. As a further consequence, isolated and purified RNA of HRV can directly cause infection, though it may be less infectious than the whole virus particle. For this reason, isolated and purified HRV RNA is used as an immunogen to develop and screen for anti-HRV antibodies of the invention. Upon infection of a cell, the HRV replicates its own genome, initially using the machinery that is already in place to replicate and/or express genes within the host cell's genome. The first proteins made by HRV are enzymes, including RNA-dependent RNA polymerase, which copies the viral RNA to form a double-stranded replicative form, which forms the blueprints for the replication of new virions. The virion is composed of an outer shell, also known as the capsid or nucleocapsid, which is made of protein. The capsid protects the contents of the core, establishes to what kind of cell the virion can attach, and infects that cell. The virion also contains an interior core composed of the genome, a positive, single-stranded RNA molecule encoding the few genes required for viral reproduction which are not present in the host cell. The virus often must supply its own enzymes for initiating replication of its genome.

Symptoms appear in most individuals within days. However, the incubation time can vary from approximately 12 hours to a week depending upon the health of the subject's immune system, the subject's genetic predisposition, and the HRV serotype. Viral shedding can occur a few days before cold symptoms are recognized by the patient, typically peaks on days 2-7 of the illness, and may last as long as 3-4 weeks. What most people recognize as cold-like symptoms are actually the local inflammatory response to the virus in the respiratory tract, mediated by interferon, which produces nasal discharge, nasal congestion, sneezing, and throat irritation.

The primary HRV infection results in the production of IgA antibodies in nasal secretions and IgG antibodies in the bloodstream. Since these viruses do not enter the circulation, the mucosal IgA response may be the most important for clearing the immediate infection, and may provide immunity for 1-2 year against that particular serotype. However, an broadly neutralizing IgG antibody raised against an invariant epitope of all HRV serotypes could be used as a vaccine or treatment for HRV infection, and, this is the foundation of the present invention.

Although rhinovirus is best known as the primary cause of the common cold, this virus also causes otitis media, nasopharyngitis, croup, bronchiolitis, and pneumonia. The common cold is mild and non-life-threatening in most subjects. However, even a mild respiratory infection can become serious in an infant or young child. Antibodies to viral serotypes develop over time. Because they simply lack the time and experience required to cultivate a mature immune system, the highest incidence of HRV infection is found in infants and young children. Children may also be more contagious than adults because they tend to have higher virus concentrations in their mucosal secretions and experience a longer duration of viral shedding. Thus, infants and young children are at heightened risk for developing, and, ultimately succumbing to, severe rhinoviral infection, e.g. nasopharyngitis, croup, bronchiolitis, and pneumonia.

Individuals who are immune-compromised or malnourished are also at greater risk for developing HRV infection. Immune-compromised individuals may have an underlying medical condition such as acquired immune deficiency syndrome, may be taking medication to suppress their immune system following a transplant, may have an autoimmune condition, or may be undergoing cancer therapy such as radiation. Malnourished individuals may also be immune-compromised, and, therefore, more susceptible to infection by HRV.

Individuals who experience frequent, close, personal contact with others are also at a heightened risk of exposure to HRV, and, therefore, infection. For instance, the individual who rides public transportation versus drives alone to work would be exposed to the virus with increased frequency. Students who attend classes are more susceptible during the school year than when they are on vacation. Individuals who live in cities are more susceptible than those who live in sparsely populated suburbs. For all of these reasons, increased risk of exposure to and infection by HRV often correlates with environmental factors such as poverty and overcrowding.

Rhinovirus infection may not cause inflammatory conditions such as asthma, but it can exacerbate its effects. Similarly, HRV causes an upper respiratory tract, which causes a blockage of one or more of the eustachian tubes, and, ultimately, development of the inflammatory middle ear infection/condition, otitis media. Binding of ICAM-1 by the rhinovirus could mediate intracellular signaling cascades that trigger further inflammation in both of these conditions. Specifically, ICAM-1 signaling could produce a recruitment of inflammatory immune cells such as macrophages and granulocytes to the upper respiratory tract (where it exacerbates asthma), and furthermore, the middle ear (where it could exacerbate otitis media). Thus, treatment of a subject with a composition of the invention (which includes an anti-HRV antibody) not only neutralizes HRV, but also eliminates the HRV-mediated inflammatory response that exacerbates any underlying inflammatory conditions, such as asthma, or any secondary inflammatory condition, such as otitis media.

Rhinovirus infection can also exacerbate cystic fibrosis. Cystic fibrosis (also known as CF or mucoviscidosis) is a recessive genetic disease, which affects the entire body, causing progressive disability until death. Impaired breathing is the most serious and well-recognized symptom. Individuals with CF experience frequent lung infections.

A preceding HRV infection can also cause bacterial superinfection, and, therefore, sinusitis.

The present invention provides a novel method for isolating novel broad and potent neutralizing monoclonal antibodies against HRV. The method involves selection of a PBMC donor with high neutralization titer of antibodies in the plasma. B cells are screened for neutralization activity prior to rescue of antibodies. Novel broadly neutralizing antibodies are obtained by emphasizing neutralization as the initial screen.

Peripheral Blood Mononuclear Cells (PBMCs) were obtained from an HRV-infected donor selected for HRV neutralizing activity in the plasma. Memory B cells were isolated and B cell culture supernatants were subjected to a primary screen of neutralization assay in a high throughput format. Optionally, HRV antigen binding assays using ELISA or like methods were also used as a screen. B cell lysates corresponding to supernatants exhibiting neutralizing activity were selected for rescue of monoclonal antibodies by standard recombinant methods.

In one embodiment, the recombinant rescue of the monoclonal antibodies involves use of a B cell culture system as described in Weitcamp J-H et al., J. Immunol. 171:4680-4688 (2003). Any other method for rescue of single B cells clones known in the art also may be employed such as EBV immortalization of B cells (Traggiai E., et al., Nat. Med. 10(8):871-875 (2004)), electrofusion (Buchacher, A., et al., 1994. AIDS Res. Hum. Retroviruses 10:359-369), and B cell hybridoma (Karpas A. et al., Proc. Natl. Acad. Sci. USA 98:1799-1804 (2001).

In some embodiments, monoclonal antibodies were rescued from the B cell cultures using variable chain gene-specific RT-PCR, and transfectant with combinations of H and L chain clones were screened again for neutralization and HRV antigen binding activities. mAbs with neutralization properties were selected for further characterization.

The antibodies of the invention are able to neutralize HRV.

Monoclonal antibodies can be produced by known procedures, e.g., as described by R. Kennet et al. in "Monoclonal Antibodies and Functional Cell Lines; Progress and Applications". Plenum Press (New York), 1984. Further materials and methods applied are based on known procedures, e.g., such as described in J. Virol. 67:6642-6647, 1993.

These antibodies can be used as prophylactic or therapeutic agents upon appropriate formulation, or as a diagnostic tool.

A "neutralizing antibody" is one that can neutralize the ability of that pathogen to initiate and/or perpetuate an infection in a host and/or in target cells in vitro. The invention provides a neutralizing monoclonal human antibody, wherein the antibody recognizes an antigen from HRV.

Preferably an antibody according to the invention is a novel monoclonal antibody referred to herein as TCN-711 (6893_E11), TCN-716 (6362_F16), TCN-717 (6358_H17), or TCN-722 (6385_L22). These antibodies were initially isolated from human samples and are produced by the B cell cultures referred to as 6893_E11, 6362_F16, 6358_H17, or 6385_L22. These antibodies have been shown to neutralize HRV in vitro. TCN-711 (6893_E11), TCN-716 (6362_F16), TCN-717 (6358_H17), and TCN-722 (6385_L22) have been shown to have broad, potent HRV neutralizing activity.

The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The positions of the CDR amino acids are defined according to the IMGT numbering system as: CDR1-IMGT positions 27 to 38, CDR2-IMGT positions 56 to 65 and CDR3-IMGT positions 105 to 117. (Lefranc, M P. et al. 2003 IMGT unique numbering for immunoglobulin and T cell receptor variable regions and Ig superfamily V-like domains. Dev Comp Immunol. 27(1):55-77; Lefranc, M P. 1997. Unique database numbering system for immunogenetic analysis. Immunology Today, 18:509; Lefranc, M P. 1999. The IMGT unique numbering for Immunoglobulins, T cell receptors and Ig-like domains. The Immunologist, 7:132-136.)

The sequences of the antibodies were determined, including the sequences of the variable regions of the Gamma heavy and Kappa or Lambda light chains of the antibodies designated TCN-711 (6893_E11), TCN-716 (6362_F16), TCN-717 (6358_H17), and TCN-722 (6385_L22). In addition, the sequence of each of the polynucleotides encoding the antibody sequences was determined. Shown below are the polypeptide and polynucleotide sequences of the gamma heavy chains and kappa light chains, with the signal peptides at the N-terminus (or 5' end) and the constant regions at the C-terminus (or 3' end) of the variable regions, which are shown in bolded text.

TCN-711 (6893_E11) gamma heavy chain nucleotide sequence: coding sequence (leader sequence in italics, variable region in bold)

(SEQ ID NO: 1)

```
ATGAAACACCTGTGGTTCTTCCTCCTCCTGGCGGCAGCTCCCAGATGGGTCCTGTCCCAGGTGC
AGCTACACCAGTGGGGCACAGGAGTGTTGAAGCCTTCGGGGACCCTGTCCCTCACCTGCGGTGT
CTATGGTGGGTCCCTCACTGATTTCTACTGGACCTGGATCCGTCAGTCCCCCGCGAGGGGCCTG
GAGTGGCTTGGAGAAATCGATCGTGATGGGGCCACGTACTATAATCCGTCCCTAAAGAGTCGAA
TCACCATTTCGATAGACACGTCCAAGAAACAATTCTCCTTGAATCTGCGGTCTGTGACCGCCGC
GGACAGGGCTGTCTACTACTGTGCGAGGCGCCCTATGTTACGAGGCGTTTGGGGGAATTTTCGT
TCCAACTGGTTCGACCCCTGGGGCCAGGGAACCCAGGTCACCGTCTCGAGCGCCTCCACCAAGG
GCCCATCGGTCTTCCCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGCGTGG
TGACCGTGCCCTCCAGCAGCTTGGGCACCCAGACCTACATCTGCAACGTGAATCACAAGCCCAG
CAACACCAAGGTGGACAAGAGAGTTGAGCCCAAATCTTGTGACAAAACTCACACATGCCCACCG
TGCCCAGCACCTGAACTCCTGGGGGGACCGTCAGTCTTCCTCTTCCCCCCAAAACCCAAGGACA
CCCTCATGATCTCCCGGACCCCTGAGGTCACATGCGTGGTGGTGGACGTGAGCCACGAAGACCC
TGAGGTCAAGTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGGA
CTCCGACGGCTCCTTCTTCCTCTATAGCAAGCTCACCGTGGACAAGAGCAGGTGGCAGCAGGGG
AACGTCTTCTCATGCTCCGTGATGCATGAGGCTCTGCACAACCACTACACGCAGAAGAGCCTCT
CCCTGTCTCCGGGTAAATGA
```

TCN-711 (6893_E11) gamma heavy chain variable region nucleotide sequence:

(SEQ ID NO: 2)
CAGGTGCAGCTACACCAGTGGGGCACAGGAGTGTTGAAGCCTTCGGG

GACCCTGTCCCTCACCTGCGGTGTCTATGGTGGGTCCCTCACTGATT

TCTACTGGACCTGGATCCGTCAGTCCCCCGCGAGGGGCCTGGAGTGG

CTTGGAGAAATCGATCGTGATGGGGCCACGTACTATAATCCGTCCCT

AAAGAGTCGAATCACCATTTCGATAGACACGTCCAAGAAACAATTCT

CCTTGAATCTGCGGTCTGTGACCGCCGCGGACAGGGCTGTCTACTAC

TGTGCGAGGCGCCCTATGTTACGAGGCGTTTGGGGGAATTTTCGTTC

CAACTGGTTCGACCCCTGGGGCCAGGGAACCCAGGTCACCGTCTCGA

GC

TCN-711 (6893_E11) gamma heavy chain amino acid sequence: expressed protein with leader sequence in italics and variable region in bold.

(SEQ ID NO: 3)
*MKHLWFFLLLAAAPRWVLS*QVQLHQWGTGVLKPSGTLSLTCGVYGGSL

TDFYWTWIRQSPARGLEWLGEIDRDGATYYNPSLKSRITISIDTSKKQ

FSLNLRSVTAADRAVYYCARRPMLRGVWGNFRSNWFDPWGQGTQVTVS

SASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVD

KRVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSF

FLYSKLTVDKSRWQQGNVFSCSVMHEALHNHYTQKSLSLSPGK

TCN-711 (6893_E11) gamma heavy chain variable region amino acid sequence: (Kabat CDRs underlined, Chothia CDRs in bold italics)

(SEQ ID NO: 4)
QVQLHQWGTGVLKPSGTLSLTCGVY*GGSLTD*DFYWTWI

RQSPARGLEWLG*EIDRDGATY*YNPSLKSRITISIDTS

KKQFSLNLRSVTAADRAVYYCAR***RPMLRGVWG

NFRSNWFDP***WGQGTQVTVSS

TCN-711 (6893_E11) gamma heavy chain Kabat CDRs:

CDR 1:
(SEQ ID NO: 5)
DFYWT

CDR 2:
(SEQ ID NO: 6)
EIDRDGATYYNPSLKS

CDR 3:
(SEQ ID NO: 7)
RPMLRGVWGNFRSNWFDP

TCN-711 (6893_E11) gamma heavy chain Chothia CDRs:

CDR 1:
(SEQ ID NO: 8)
GGSLTD

CDR 2:
(SEQ ID NO: 9)
EIDRDGATY

CDR 3:
(SEQ ID NO: 7)
RPMLRGVWGNFRSNWFDP

TCN-711 (6893_E11) lambda light chain nucleotide sequence: coding sequence (leader sequence in italics, variable region in bold)

(SEQ ID NO: 10)
*ATGGCCAGCTTCCCTCTCCTCCTCACCCTTCTCATTCACTGCACAGGG*

*TCCTGGGCC*CAGTCTGTCTTGACGCAGCCGCCCTCAGTGTCTGCGGCC

CCAGGACAGAAGGTCTCCATCTCCTGCTCTGGAAGCAGCTCCAACATT

GGGTATAGTTATGTATCCTGGTATCAACAAGTCCCAGGATCAGCCCCC

AAACTCCTCATCTATGAGAATAATAAGAGACCCTCAGGGATTCCTGAC

CGATTCTCGGCCTCCAAGTCTGGCACGTCAGCCACCCTGGACATCACC

GGACTCCAGACTGGGGACGAGGCCGATTATTATTGCGGAACATGGGAT

ACCAGGCTGTTTGGTGGAGTGTTCGGCGGAGGGACCAAGCTGACCGTT

CTAGGTCAGCCCAAGGCTGCCCCCTCGGTCACTCTGTTCCCGCCCTCC

TCTGAGGAGCTTCAAGCCAACAAGGCCACACTGGTGTGTCTCATAAGT

GACTTCTACCCGGGAGCCGTGACAGTGGCCTGGAAGGCAGATAGCAGC

CCCGTCAAGGCGGGAGTGGAGACCACCACACCCTCCAAACAAAGCAAC

AACAAGTACGCGGCCAGCAGCTACCTGAGCCTGACGCCTGAGCAGTGG

AAGTCCCACAAAAGCTACAGCTGCCAGGTCACGCATGAAGGGAGCACC

GTGGAGAAGACAGTGGCCCCTACAGAATGTTCATAG

TCN-711 (6893_E11) lambda light chain variable region nucleotide sequence:

(SEQ ID NO: 11)
CAGTCTGTCTTGACGCAGCCGCCCTCAGTGTCTGCGGCCCCAGGACAG

AAGGTCTCCATCTCCTGCTCTGGAAGCAGCTCCAACATTGGGTATAGT

TATGTATCCTGGTATCAACAAGTCCCAGGATCAGCCCCCAAACTCCTC

ATCTATGAGAATAATAAGAGACCCTCAGGGATTCCTGACCGATTCTCG

GCCTCCAAGTCTGGCACGTCAGCCACCCTGGACATCACCGGACTCCAG

ACTGGGGACGAGGCCGATTATTATTGCGGAACATGGGATACCAGGCTG

TTTGGTGGAGTGTTCGGCGGAGGGACCAAGCTGACCGTTCTA

TCN-711 (6893_E11) lambda light chain amino acid sequence: expressed protein with leader sequence in italics and variable region in bold.

(SEQ ID NO: 12)
*MASFPLLLTLLIHCTGSWA*QSVLTQPPSVSAAPGQKVSISCSGSSSNI

GYSYVSWYQQVPGSAPKLLIYENNKRPSGIPDRFSASKSGTSATLDIT

GLQTGDEADYYCGTWDTRLFGGVFGGGTKLTVLGQPKAAPSVTLFPPS
SEELQANKATLVCLISDFYPGAVTVAWKADSSPVKAGVETTTPSKQSN
NKYAASSYLSLTPEQWKSHKSYSCQVTHEGSTVEKTVAPTECS

TCN-711 (6893_E11) lambda light chain variable region amino acid sequence: (Kabat CDRs underlined, Chothia CDRs in bold italics)

(SEQ ID NO: 13)
QSVLTQPPSVSAAPGQKVSISC*SGSSSNIGYSYVS*WYQQVPGSAPKL
LIY*ENNKRPS*GIPDRFSASKSGTSATLDITGLQTGDEADYY
C*GTWDTRLFGGV*FGGGTKLTVL

TCN-711 (6893_E11) lambda light chain Kabat CDRs:

CDR 1:
(SEQ ID NO: 14)
SGSSSNIGYSYVS

CDR 2:
(SEQ ID NO: 15)
ENNKRPS

CDR 3:
(SEQ ID NO: 16)
GTWDTRLFGGV

TCN-711 (6893_E11) lambda light chain Chothia CDRs:

CDR 1:
(SEQ ID NO: 14)
SGSSSNIGYSYVS

CDR 2:
(SEQ ID NO: 15)
ENNKRPS

CDR 3:
(SEQ ID NO: 16)
GTWDTRLFGGV

TCN-716 (6362_F16) gamma heavy chain nucleotide sequence: coding sequence (leader sequence in italics, variable region in bold)

(SEQ ID NO: 17)
*ATGGAGTTTGGGCTGAGCTGGGTTCTCCTTGTTGCCATTTTAAAAGGTGCCCAGTGT*__GAGGTGC__
AACTGGTGGAGTCTGGGGGAGGCTTGGTCCTGCCGGGGGGCTCTCTGAGACTCTCGTGTTCAGC
GTCTGGATTCACATTGACTGACTTTGCTATGCACTGGGTCCGACAGGCTCCAGGGAAGGGACTG
GAGCTCGTCTCAAGTATTAGTCGGGATGGTTCTACTAAATACTCTGGAGACTCCGTGAAGGGCA
GGGTCGCCATCTCCAGGGACAGTGTGGAGAATAAGTTGCATCTTCAGATGAGCGGTCTGAGGTC
TGCGGACACGGCTGTGTATTATTGTGTGAGAGACTCCCCCTATTATCTTGATATTGTTGGTTAT
CGATACTTCCACCACTATGGAATGGACGTCTGGGGCCAGGGGACCACGGTCACCGTCTCGAGCG
CCTCCACCAAGGGCCCATCGGTCTTCCCCCTGGCACCCTCCTCCAAGAGCACCTCTGGGGGCAC
AGCGGCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTACTCCC
TCAGCAGCGTGGTGACCGTGCCCTCCAGCAGCTTGGGCACCCAGACCTACATCTGCAACGTGAA
TCACAAGCCCAGCAACACCAAGGTGGACAAGAGAGTTGAGCCCAAATCTTGTGACAAAACTCAC
ACATGCCCACCGTGCCCAGCACCTGAACTCCTGGGGGGACCGTCAGTCTTCCTCTTCCCCCCAA
AACCCAAGGACACCCTCATGATCTCCCGGACCCCTGAGGTCACATGCGTGGTGGTGGACGTGAG
CCACGAAGACCCTGAGGTCAAGTTCAACTGGTACGTGGACGGCGTGGAGGTGCATAATGCCAAG
ACAAAGCCGCGGGAGGAGCAGTACAACAGCACGTACCGTGTGGTCAGCGTCCTCACCGTCCTGC
ACCAGGACTGGCTGAATGGCAAGGAGTACAAGTGCAAGGTCTCCAACAAAGCCCTCCCAGCCCC
CATCGAGAAAACCATCTCCAAAGCCAAAGGGCAGCCCCGAGAACCACAGGTGTACACCCTGCCC
CCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCC
TCCCGTGCTGGACTCCGACGGCTCCTTCTTCCTCTATAGCAAGCTCACCGTGGACAAGAGCAGG
TGGCAGCAGGGGAACGTCTTCTCATGCTCCGTGATGCATGAGGCTCTGCACAACCACTACACGC
AGAAGAGCCTCTCCCTGTCTCCGGGTAAATGA

TCN-716 (6362_F16) gamma heavy chain variable region nucleotide sequence:

(SEQ ID NO: 18)
GAGGTGCAACTGGTGGAGTCTGGGGGAGGCTTGGTCCTGCCGGGGGGC
TCTCTGAGACTCTCGTGTTCAGCGTCTGGATTCACATTGACTGACTTT
GCTATGCACTGGGTCCGACAGGCTCCAGGGAAGGGACTGGAGCTCGTC
TCAAGTATTAGTCGGGATGGTTCTACTAAATACTCTGGAGACTCCGTG
AAGGGCAGGGTCGCCATCTCCAGGGACAGTGTGGAGAATAAGTTGCAT
CTTCAGATGAGCGGTCTGAGGTCTGCGGACACGGCTGTGTATTATTGT
GTGAGAGACTCCCCCTATTATCTTGATATTGTTGGTTATCGATACTTC
CACCACTATGGAATGGACGTCTGGGGCCAGGGGACCACGGTCACCGTC
TCGAGC

TCN-716 (6362_F16) gamma heavy chain amino acid sequence: expressed protein with leader sequence in italics and variable region in bold.

(SEQ ID NO: 19)
*MEFGLSWVLLVAILKGAQC*EVQLVESGGGLVLPGGSLRLSCSASGFTL
TDFAMHWVRQAPGKGLELVSSISRDGSTKYSGDSVKGRVAISRDSVEN
KLHLQMSGLRSADTAVYYCVRDSPYYLDIVGYRYFHHYGMDVWGQGTT
VTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSN
TKVDKRVEPKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK

TCN-716 (6362_F16) gamma heavy chain variable region amino acid sequence: (Kabat CDRs underlined, Chothia CDRs in bold italics)

(SEQ ID NO: 20)
EVQLVESGGGLVLPGGSLRLSCSAS*GFTLTD*<u>FAMH</u>WVRQAPGKGLEL
VS<u>*SISRDGSTKY*SGDSVKG</u>RVAISRDSVENKLHLQMSGLRSADTAVY
YCVR<u>*DSPYYLDIVGYRYFHHYGMDV*</u>WGQGTTVTVSS

TCN-716 (6362_F16) gamma heavy chain Kabat CDRs:

CDR 1:
(SEQ ID NO: 21)
DFAMH

CDR 2:
(SEQ ID NO: 22)
SISRDGSTKYSGDSVKG

CDR 3:
(SEQ ID NO: 23)
DSPYYLDIVGYRYFHHYGMDV

TCN-716 (6362_F16) gamma heavy chain Chothia CDRs:

CDR 1:
(SEQ ID NO: 24)
GFTLTD

CDR 2:
(SEQ ID NO: 25)
SISRDGSTKY

CDR 3:
(SEQ ID NO: 23)
DSPYYLDIVGYRYFHHYGMDV

TCN-716 (6362_F16) kappa light chain nucleotide sequence: coding sequence (leader sequence in italics, variable region in bold)

(SEQ ID NO: 26)
*ATGGAAACCCCAGCTCAGCTTCTCTTCCTCCTGCTACTCTGGCTCCCA*
*GATACCACCGGA*GAGATTGTGTTGACGCAGTCGCCAGGCACCCTGTCT
TTGTCTCCAGGGGACAGAGTCACCCTCTCCTGCAGGGCCAGTCAAATT
CTTCACAGCTATAATTTAGCCTGGTATCAGCACAGACCTGGCCAGGCT
CCCAGGCTCCTCATTTATGGTGCATATAACAGGGCCAGTGGCATCCCA
GACAGGTTCAGTGGCAGTGGGTCTGGGGCAGACTTCACCCTCACCATC
GGCAGACTGCAGCGTGACGATTTTGCAGTTTATTACTGTCAACAGTAT
GGTGACTCACCATCACCAGGCCTCACTTTCGGCGGAGGAACCAAACTG
GAGTTCAAACGTACGGTGGCTGCACCATCTGTCTTCATCTTCCCGCCA
TCTGATGAGCAGTTGAAATCTGGAACTGCCTCTGTTGTGTGCCTGCTG
AATAACTTCTATCCCAGAGAGGCCAAAGTACAGTGGAAGGTGGATAAC
GCCCTCCAATCGGGTAACTCCCAGGAGAGTGTCACAGAGCAGGACAGC
AAGGACAGCACCTACAGCCTCAGCAGCACCCTGACGCTGAGCAAAGCA
GACTACGAGAAACACAAAGTCTACGCCTGCGAAGTCACCCATCAGGGC
CTGAGCTCGCCCGTCACAAAGAGCTTCAACAGGGGAGAGTGTTAG

TCN-716 (6362_F16) kappa light chain variable region nucleotide sequence:

(SEQ ID NO: 27)
GAGATTGTGTTGACGCAGTCGCCAGGCACCCTGTCTTTGTCTCCAGGG
GACAGAGTCACCCTCTCCTGCAGGGCCAGTCAAATTCTTCACAGCTAT
AATTTAGCCTGGTATCAGCACAGACCTGGCCAGGCTCCCAGGCTCCTC
ATTTATGGTGCATATAACAGGGCCAGTGGCATCCCAGACAGGTTCAGT
GGCAGTGGGTCTGGGGCAGACTTCACCCTCACCATCGGCAGACTGCAG
CGTGACGATTTTGCAGTTTATTACTGTCAACAGTATGGTGACTCACCA
TCACCAGGCCTCACTTTCGGCGGAGGAACCAAACTGGAGTTCAAA

TCN-716 (6362_F16) kappa light chain amino acid sequence: expressed protein with leader sequence in italics and variable region in bold.

(SEQ ID NO: 28)
*METPAQLLFLLLLWLPDTTG*EIVLTQSPGTLSLSPGDRVTLSCRASQI
LHSYNLAWYQHRPGQAPRLLIYGAYNRASGIPDRFSGSGSGADFTLTI

GRLQRDDFAVYYCQQYGDSPSPGLTFGGGTKLEFKRTVAAPSVFIFPP
SDEQLKSGTASVVCLLNNFYPREAKVQWKVDNALQSGNSQESVTEQDS
KDSTYSLSSTLTLSKADYEKHKVYACEVTHQGLSSPVTKSFNRGEC

TCN-716 (6362_F16) kappa light chain variable region amino acid sequence: (Kabat CDRs underlined, Chothia CDRs in bold italics)

(SEQ ID NO: 29)
EIVLTQSPGTLSLSPGDRVTLSC*RASQILHSYNLA*WYQHRPGQAPR
LLIY*GAYNRAS*GIPDRFSGSGSGADFTLTIGRLQRDDFAVYY
C*QQYGDSPSPGLT*FGGGTKLEFK

TCN-716 (6362_F16) kappa light chain Kabat CDRs:

CDR 1:
(SEQ ID NO: 30)
RASQILHSYNLA

CDR 2:
(SEQ ID NO: 31)
GAYNRAS

CDR 3:
(SEQ ID NO: 32)
QQYGDSPSPGLT

TCN-716 (6362_F16) kappa light chain Chothia CDRs:

CDR 1:
(SEQ ID NO: 30)
RASQILHSYNLA

CDR 2:
(SEQ ID NO: 31)
GAYNRAS

CDR 3:
(SEQ ID NO: 32)
QQYGDSPSPGLT

TCN-717 (6358_H17) gamma heavy chain nucleotide sequence: coding sequence (leader sequence in italics, variable region in bold)

(SEQ ID NO: 33)
*ATGAAACACCTGTGGTTCTTCCTCCTACTGATGGCGGCTCCCAGATGG*
*GTCCTGTCCC*AGCTGCAACTGCTTGAGTCGGGCCCAAGACTGGTGAAG
GCTTCGGAGACCCTGTCACTCACCTGCAGTGTCCCTATGGGCTCCATC
CTCCAAAATGATTATCATTGGGCCTGGGTCCGCCAGCCCCCAGGGAGG
GGCCTGGAGTGGATTGGGAGTGTTCACTATAGACAAAAATCCTACTAC
AGCCCGTCCCTCAAGAGCCGAGTCTTCATGTCCGTAGACACGTCCAGA
GACCAGTTCTCCCTAAAACTCTTCTCTCTGGCCGCCGCGGACACGGCC
GTATATTATTGTGCGAGACATAATCGGGAAGATTATTATGACAGTAAT
GCCTACTTTGACGAGTGGGGCCTGGGAGCTCGGATCACCGTCTCGAGC
GCCTCCACCAAGGGCCCATCGGTCTTCCCCCTGGCACCCTCCTCCAAG
AGCACCTCTGGGGGCACAGCGGCCCTGGGCTGCCTGGTCAAGGACTAC
TTCCCCGAACCGGTGACGGTGTCGTGGAACTCAGGCGCCCTGACCAGC
GGCGTGCACACCTTCCCGGCTGTCCTACAGTCCTCAGGACTCTACTCC
CTCAGCAGCGTGGTGACCGTGCCCTCCAGCAGCTTGGGCACCCAGACC
TACATCTGCAACGTGAATCACAAGCCCAGCAACACCAAGGTGGACAAG
AGAGTTGAGCCCAAATCTTGTGACAAAACTCACACATGCCCACCGTGC
CCAGCACCTGAACTCCTGGGGGGACCGTCAGTCTTCCTCTTCCCCCCA
AAACCCAAGGACACCCTCATGATCTCCCGGACCCCTGAGGTCACATGC
GTGGTGGTGGACGTGAGCCACGAAGACCCTGAGGTCAAGTTCAACTGG
TACGTGGACGGCGTGGAGGTGCATAATGCCAAGACAAAGCCGCGGGAG
GAGCAGTACAACAGCACGTACCGTGTGGTCAGCGTCCTCACCGTCCTG
CACCAGGACTGGCTGAATGGCAAGGAGTACAAGTGCAAGGTCTCCAAC
AAAGCCCTCCCAGCCCCCATCGAGAAAACCATCTCCAAAGCCAAAGGG
CAGCCCCGAGAACCACAGGTGTACACCCTGCCCCCATCCCGGGAGGAG
ATGACCAAGAACCAGGTCAGCCTGACCTGCCTGGTCAAAGGCTTCTAT
CCCAGCGACATCGCCGTGGAGTGGGAGAGCAATGGGCAGCCGGAGAAC
AACTACAAGACCACGCCTCCCGTGCTGGACTCCGACGGCTCCTTCTTC
CTCTATAGCAAGCTCACCGTGGACAAGAGCAGGTGGCAGCAGGGGAAC
GTCTTCTCATGCTCCGTGATGCATGAGGCTCTGCACAACCACTACACG
CAGAAGAGCCTCTCCCTGTCTCCGGGTAAATGA

TCN-717 (6358_H17) gamma heavy chain variable region nucleotide sequence:

(SEQ ID NO: 34)
CAGCTGCAACTGCTTGAGTCGGGCCCAAGACTGGTGAAGGCTTCGGAG
ACCCTGTCACTCACCTGCAGTGTCCCTATGGGCTCCATCCTCCAAAAT
GATTATCATTGGGCCTGGGTCCGCCAGCCCCCAGGGAGGGGCCTGGAG
TGGATTGGGAGTGTTCACTATAGACAAAAATCCTACTACAGCCCGTCC
CTCAAGAGCCGAGTCTTCATGTCCGTAGACACGTCCAGAGACCAGTTC
TCCCTAAAACTCTTCTCTCTGGCCGCCGCGGACACGGCCGTATATTAT
TGTGCGAGACATAATCGGGAAGATTATTATGACAGTAATGCCTACTTT
GACGAGTGGGGCCTGGGAGCTCGGATCACCGTCTCGAGC

TCN-717 (6358_H17) gamma heavy chain amino acid sequence: expressed protein with leader sequence in italics and variable region in bold.

(SEQ ID NO: 35)
*MKHLWFFLLLMAAPRWVLSQ*LQLLESGPRLVKASETLSLTCSVPMGSI
LQNDYHWAWVRQPPGRGLEWIGSVHYRQKSYYSPSLKSRVFMSVDTSR
DQFSLKLFSLAAADTAVYYCARHNREDYYDSNAYFDEWGLGARITVSS
ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVL
HQDWLNGKEYKCKVSNKALPAPIEKTISKAKGQPREPQVYTLPPSREE

MTKNQVSLTCLVKGFYPSDIAVEWESNGQPENNYKTTPPVLDSDGSFF

LYSKLTVDKSRWQQGNVFSCSVMHEALHNHYTQKSLSLSPGK

TCN-717 (6358_H17) gamma heavy chain variable region amino acid sequence: (Kabat CDRs underlined, Chothia CDRs in bold italics)

(SEQ ID NO: 36)
QLQLLESGPRLVKASETLSLTCSVP*MGSILQND*YHWAWVRQPPGR

GLEWIG*SVHYRQKSY*YSPSLKSRVFMSVDTSRDQFSLKLFSLA

AADTAVYYCAR*HNREDYYDSNAYFDE*WGLGARITVSS

TCN-717 (6358_H17) gamma heavy chain Kabat CDRs:

```
CDR 1:
                          (SEQ ID NO: 37)
QNDYHWA

CDR 2:
                          (SEQ ID NO: 38)
SVHYRQKSYYSPSLKS

CDR 3:
                          (SEQ ID NO: 39)
HNREDYYDSNAYFDE
```

TCN-717 (6358_H17) gamma heavy chain Chothia CDRs:

```
CDR 1:
                          (SEQ ID NO: 40)
MGSILQND

CDR 2:
                          (SEQ ID NO: 41)
SVHYRQKSY

CDR 3:
                          (SEQ ID NO: 39)
HNREDYYDSNAYFDE
```

TCN-717 (6358_H17) lambda light chain nucleotide sequence: coding sequence (leader sequence in italics, variable region in bold)

(SEQ ID NO: 42)
*ATGGCCAGCTTCCCTCTCCTCCTCGGCGTCCTTGCTTACTGCACAGGG*

*TCGGGGGCC*TCCTATGAGTTGTCTCAGCCACCCTCAGTGTCCGTGTTC

CCGGGACAGACAGCAAGCATCACCTGTTCTGGAGATGACTTGGAAAAC

ACCCTTGTTTGTTGGTATCAACAAAAGTCAGGGCAGTCCCCTGTGTTG

GTCGTCTATCAAGATTCCAAGCGGCCCTCAGGGATCCCTGAGCGATTC

TCTGGCTCCAGAGTTAAAGACACAGCCACTCTGACCATCAGCGGGACG

CAGGCTTTCGATGAGGCTGACTATTATTGTCAGACGTGGCACAGGTCC

ACCGCCCAGTATGTCTTCGGACCTGGGACCAAGGTCACCGTTCTAGGT

CAGCCCAAGGCTGCCCCCTCGGTCACTCTGTTCCCGCCCTCCTCTGAG

GAGCTTCAAGCCAACAAGGCCACACTGGTGTGTCTCATAAGTGACTTC

TACCCGGGAGCCGTGACAGTGGCCTGGAAGGCAGATAGCAGCCCCGTC

AAGGCGGGAGTGGAGACCACCACACCCTCCAAACAAAGCAACAACAAG

TACGCGGCCAGCAGCTACCTGAGCCTGACGCCTGAGCAGTGGAAGTCC

CACAAAAGCTACAGCTGCCAGGTCACGCATGAAGGGAGCACCGTGGAG

AAGACAGTGGCCCCTACAGAATGTTCATAG

TCN-717 (6358_H17) lambda light chain variable region nucleotide sequence:

(SEQ ID NO: 43)
TCCTATGAGTTGTCTCAGCCACCCTCAGTGTCCGTGTTCCCGGGACAG

ACAGCAAGCATCACCTGTTCTGGAGATGACTTGGAAAACACCCTTGTT

TGTTGGTATCAACAAAAGTCAGGGCAGTCCCCTGTGTTGGTCGTCTAT

CAAGATTCCAAGCGGCCCTCAGGGATCCCTGAGCGATTCTCTGGCTCC

AGAGTTAAAGACACAGCCACTCTGACCATCAGCGGGACGCAGGCTTTC

GATGAGGCTGACTATTATTGTCAGACGTGGCACAGGTCCACCGCCCAG

TATGTCTTCGGACCTGGGACCAAGGTCACCGTTCTA

TCN-717 (6358_H17) lambda light chain amino acid sequence: expressed protein with leader sequence in italics and variable region in bold.

(SEQ ID NO: 44)
*MASFPLLLGVLAYCTGSGA*SYELSQPPSVSVFPGQTASITCSGDDLEN

TLVCWYQQKSGQSPVLVVYQDSKRPSGIPERFSGSRVKDTATLTISGT

QAFDEADYYCQTWHRSTAQYVFGPGTKVTVLGQPKAAPSVTLFPPSSE

ELQANKATLVCLISDFYPGAVTVAWKADSSPVKAGVETTTPSKQSNNK

YAASSYLSLTPEQWKSHKSYSCQVTHEGSTVEKTVAPTECS

TCN-717 (6358_H17) lambda light chain variable region amino acid sequence: (Kabat CDRs underlined, Chothia CDRs in bold italics)

(SEQ ID NO: 45)
SYELSQPPSVSVFPGQTASITC*SGDDLENTLVC*WYQQKSGQSPVLVVY*QDSKRPS*GIPER

FSGSRVKDTATLTISGTQAFDEADYYC*QTWHRSTTAQYV*FGPGTKVTVL

TCN-717 (6358_H17) lambda light chain Kabat CDRs:

| | | |
|---|---|---|
| CDR 1: | SGDDLENTLVC | (SEQ ID NO: 46) |
| CDR 2: | QDSKRPS | (SEQ ID NO: 47) |
| CDR 3: | QTWHRSTAQYV | (SEQ ID NO: 48) |

TCN-717 (6358_H17) lambda light chain Chothia CDRs:

| | | |
|---|---|---|
| CDR 1: | SGDDLENTLVC | (SEQ ID NO: 46) |
| CDR 2: | QDSKRPS | (SEQ ID NO: 47) |
| CDR 3: | QTWHRSTAQYV | (SEQ ID NO: 48) |

TCN-722 (6385_L22) gamma heavy chain nucleotide sequence: coding sequence (leader sequence in italics, variable region in bold)

(SEQ ID NO: 49)
*ATGAAACACCTGTGGTTCTTCCTCCTGCTGGTGGCGGCTCCCAGATGGGTCCTGTCC*CAGTTGC
AGCTGCTTGAGTCGGGCCCAGGACTGGTGAAGCCTTCGGAGACCCTTTCACTCACCTGCAGTGT
CTCTGGGGACTCCCTCCTCAGTAATGATCAATACTGGGCCTGGGTCCGCCAGCCCCCAGGGAGG
GGCCTGGAGTGGATTGGGAGTGTTCACTATAGACGACGAAACTACTACAGCCCGTCCCTGGAGA
GCCGGATCTTCATGTCAGTAGACACGTCCAGAAACGAGTTCTCCTTAAAAGTTTTCTCTGTGAC
GGCCGCGGACACGGCCGTGTATTATTGTGCGAGACACAATTGGGAAGATTATTATGAGAGTAAT
GCCTACTTTGACTACTGGGGCCTGGGAACCCGGATCACCGTCTCGAGCGCCTCCACCAAGGGCC
CATCGGTCTTCCCCCTGGCACCCTCCTCCAAGAGCACCTCTGGGGGCACAGCGGCCCTGGGCTG
CCTGGTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAATCACAAGCCCAGCAA
CACCAAGGTGGACAAGAGAGTTGAGCCCAAATCTTGTGACAAAACTCACACATGCCCACCGTGC
CCAGCACCTGAACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCACGAAGACCCTGA
GGTCAAGTTCAACTGGTACGTGGACGGCGTGGAGGTGCATAATGCCAAGACAAAGCCGCGGGAG
GAGCAGTACAACAGCACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCTGGACTC
CGACGGCTCCTTCTTCCTCTATAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTCTCCC
TGTCTCCGGGTAAATGA

TCN-722 (6385_L22) gamma heavy chain variable region nucleotide sequence:

(SEQ ID NO: 50)
CAGTTGCAGCTGCTTGAGTCGGGCCCAGGACTGGTGAAGCCTTCGGAGACCCTTTCACTCACCT
GCAGTGTCTCTGGGGACTCCCTCCTCAGTAATGATCAATACTGGGCCTGGGTCCGCCAGCCCCC
AGGGAGGGGCCTGGAGTGGATTGGGAGTGTTCACTATAGACGACGAAACTACTACAGCCCGTCC
CTGGAGAGCCGGATCTTCATGTCAGTAGACACGTCCAGAAACGAGTTCTCCTTAAAAGTTTTCT
CTGTGACGGCCGCGGACACGGCCGTGTATTATTGTGCGAGACACAATTGGGAAGATTATTATGA
GAGTAATGCCTACTTTGACTACTGGGGCCTGGGAACCCGGATCACCGTCTCGAGC

TCN-722 (6385_L22) gamma heavy chain amino acid sequence: expressed protein with leader sequence in italics and variable region in bold.

(SEQ ID NO: 51)
*MKHLWFFLLLVAAPRWVLS*QLQLLESGPGLVKPSETLSLTCSVSGDSLLSNDQYWAW
VRQPPGRGLEWIGSVHYRRRNYYSPSLESRIFMSVDTSRNEFSLKVFSVTAADTAVY
YCARHNWEDYYESNAYFDYWGLGTRITVSSASTKGPSVFPLAPSSKSTSGGTAALGC
LVKDYFPEPVTVSWNSGALTSGVHTFPAVLQSSGLYSLSSVVTVPSSSLGTQTYICNVNH
KPSNTKVDKRVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYT
QKSLSLSPGK

TCN-722 (6385_L22) gamma heavy chain variable region amino acid sequence: (Kabat CDRs underlined, Chothia CDRs in bold italics)

(SEQ ID NO: 52)
QLQLLESGPGLVKPSETLSLTCSVS*GDSLL*<u>*SND*QYWA</u>WVRQPPGRGLEWIG
<u>S*VHYRRRNY*YSPSLES</u>RIFMSVDTSRNEFSLKVFSVTAADTAVYYCAR
<u>*HNWEDYYESNAYFDY*</u>WGLGTRITVSS

TCN-722 (6385_L22) gamma heavy chain Kabat CDRs:

| | | |
|---|---|---|
| CDR 1: | SNDQYWA | (SEQ ID NO: 53) |
| CDR 2: | SVHYRRRNYYSPSLES | (SEQ ID NO: 54) |
| CDR 3: | HNWEDYYESNAYFDY | (SEQ ID NO: 55) |

TCN-722 (6385_L22) gamma heavy chain Chothia CDRs:

| | | |
|---|---|---|
| CDR 1: | GDSLLSND | (SEQ ID NO: 56) |
| CDR 2: | SVHYRRRNY | (SEQ ID NO: 57) |
| CDR 3: | HNWEDYYESNAYFDY | (SEQ ID NO: 55) |

TCN-722 (6385_L22) lambda light chain nucleotide sequence: coding sequence (leader sequence in italics, variable region in bold)

(SEQ ID NO: 58)
*ATGGCCAGCTTCCCTCTCTTCCTCGGCGTCCTTGCTTACTGCACAGGATCGGGGGCC*TCCTTTG
ACTTGACTCAGCCACCCTCAGTGTCCGTGTCCCCAGGACAGACCGCAACCATCACCTGTTCTGG
AGATCAATTGGAAAATACCTTTGTTTGCTGGTATCAACAGAGGTCAGGCCAGGCCCCTGTGTTG
GTCATCTATCAAGGTTCCAAGCGGCCCTCAGGGATCCCTGAGCGATTCTCTGGCTCCAGGTCTG
GGAACACAGCCACTCTGACCATCAGCAGGACCCAGGCTTTGGATGAGGCTGACTATTACTGTCA
GGCGTGGGACAGGTCCACCGCCCACTATGTCTTCGGAACTGGGACCAAGGTCACCGTTCTAGGT
CAGCCCAAGGCTGCCCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACAGTGGCCTGGAAGGC
AGATAGCAGCCCCGTCAAGGCGGGAGTGGAGACCACCACACCCTCCAAACAAAGCAACAACAAG
TACGCGGCCAGCAGCTACCTGAGCCTGACGCCTGAGCAGTGGAAGTCCCACAAAAGCTACAGCT
GCCAGGTCACGCATGAAGGGAGCACCGTGGAGAAGACAGTGGCCCCTACAGAATGTTCATAG

TCN-722 (6385_L22) lambda light chain variable region nucleotide sequence:

(SEQ ID NO: 59)
TCCTTTGACTTGACTCAGCCACCCTCAGTGTCCGTGTCCCCAGGACAGACCGCAACCATCACCT
GTTCTGGAGATCAATTGGAAAATACCTTTGTTTGCTGGTATCAACAGAGGTCAGGCCAGGCCCC
TGTGTTGGTCATCTATCAAGGTTCCAAGCGGCCCTCAGGGATCCCTGAGCGATTCTCTGGCTCC
AGGTCTGGGAACACAGCCACTCTGACCATCAGCAGGACCCAGGCTTTGGATGAGGCTGACTATT

```
ACTGTCAGGCGTGGGACAGGTCCACCGCCCACTATGTCTTCGGACCTGGGACCAAGGTCACCGT

TCTA
```

TCN-722 (6385_L22) lambda light chain amino acid sequence: expressed protein with leader sequence in italics and variable region in bold.

(SEQ ID NO: 60)
*MASFPLFLGVLAYCTGSGA*SFDLTQPPSVSVSPGQTATITCSGDQLENTF

VCWYQQRSGQAPVLVIYQGSKRPSGIPERFSGSRSGNTATLTISRTQALD

EADYYCQAWDRSTAHYVFGPGTKVTVLGQPKAAPSVTLFPPSSEELQANK

ATLVCLISDFYPGAVTVAWKADSSPVKAGVETTTPSKQSNNKYAASSYLS

LTPEQWKSHKSYSCQVTHEGSTVEKTVAPTECS

TCN-722 (6385_L22) lambda light chain variable region amino acid sequence: (Kabat CDRs underlined, Chothia CDRs in bold italics)

(SEQ ID NO: 61)
SFDLTQPPSVSVSPGQTATITC*SGDQLEMTFVC*WYQQRSGQAPVLVIY*QGSKRPS*GIPER

FSGSRSGNTATLTISRTQALDEADYYC*QAWDRSTAHYV*FGPGTKVTVL

TCN-722 (6385_L22) lambda light chain Kabat CDRs:

| CDR 1: | SGDQLENTFVC | (SEQ ID NO: 62) |
| CDR 2: | QGSKRPS | (SEQ ID NO: 63) |
| CDR 3: | QAWDRSTAHYV | (SEQ ID NO: 64) |

TCN-722 (6385_L22) lambda light chain Chothia CDRs:

| CDR 1: | SGDQLENTFVC | (SEQ ID NO: 62) |
| CDR 2: | QGSKRPS | (SEQ ID NO: 63) |
| CDR 3: | QAWDRSTAHYV | (SEQ ID NO: 64) |

The TCN-711 (6893_E11) antibody includes a heavy chain variable region (SEQ ID NO: 4), encoded by the nucleic acid sequence shown in SEQ ID NO: 2, and a light chain variable region (SEQ ID NO: 13) encoded by the nucleic acid sequence shown in SEQ ID NO: 11.

The heavy chain CDRs of the TCN-711 (6893_E11) antibody have the following sequences per Kabat definition: CDR 1: DFYWT (SEQ ID NO: 5), CDR 2: EIDRDGATYYNPSLKS (SEQ ID NO: 6) and CDR 3: RPMLRGVWGNFRSNWFDP (SEQ ID NO: 7). The light chain CDRs of the TCN-711 (6893_E11) antibody have the following sequences per Kabat definition: CDR 1: SGSSSNIGYSYVS (SEQ ID NO: 14), CDR 2: ENNKRPS (SEQ ID NO: 15), and CDR 3: GTWDTRLFGGV (SEQ ID NO: 16).

The heavy chain CDRs of the TCN-711 (6893_E11) antibody have the following sequences per Chothia definition: CDR 1: GGSLTD (SEQ ID NO: 8), CDR 2: EIDRDGATY (SEQ ID NO: 9), and CDR 3: RPMLRGVWGNFRSNWFDP (SEQ ID NO: 7). The light chain CDRs of the TCN-711 (6893_E11) antibody have the following sequences per Chothia definition: CDR 1: SGSSSNIGYSYVS (SEQ ID NO: 14), CDR 2: ENNKRPS (SEQ ID NO: 15), and CDR 3: GTWDTRLFGGV (SEQ ID NO: 16).

The TCN-716 (6362_F16) antibody includes a heavy chain variable region (SEQ ID NO: 20), encoded by the nucleic acid sequence shown in SEQ ID NO: 18, and a light chain variable region (SEQ ID NO: 29) encoded by the nucleic acid sequence shown in SEQ ID NO: 27.

The heavy chain CDRs of the TCN-716 (6362_F16) antibody have the following sequences per Kabat definition: CDR 1: DFAMH (SEQ ID NO: 21), CDR 2: SISRDGSTKYSGDSVKG (SEQ ID NO: 22), and CDR 3: DSPYYLDIVGYRYFHHYGMDV (SEQ ID NO: 23). The light chain CDRs of the TCN-716 (6362_F16) antibody have the following sequences per Kabat definition: CDR 1: RASQILHSYNLA (SEQ ID NO: 30), CDR 2: GAYNRAS (SEQ ID NO: 31), CDR 3: QQYGDSPSPGLT (SEQ ID NO: 32).

The heavy chain CDRs of the TCN-716 (6362_F16) antibody have the following sequences per Chothia definition: CDR 1: GFTLTD (SEQ ID NO: 24), CDR 2: SISRDGSTKY (SEQ ID NO: 25), and CDR 3: DSPYYLDIVGYRYFHHYGMDV (SEQ ID NO: 23). The light chain CDRs of the TCN-716 (6362_F16) antibody have the following sequences per Chothia definition: CDR 1: RASQILHSYNLA (SEQ ID NO: 30), CDR 2: GAYNRAS (SEQ ID NO: 31), CDR 3: QQYGDSPSPGLT (SEQ ID NO: 32).

The TCN-717 (6358_H17) antibody includes a heavy chain variable region (SEQ ID NO: 36), encoded by the nucleic acid sequence shown in SEQ ID NO: 34, and a light chain variable region (SEQ ID NO: 45) encoded by the nucleic acid sequence shown in SEQ ID NO: 43.

The heavy chain CDRs of the TCN-717 (6358_H17) antibody have the following sequences per Kabat definition: CDR 1: QNDYHWA (SEQ ID NO: 37), CDR 2: SVHYRQKSYYSPSLKS (SEQ ID NO: 38), and CDR 3: HNREDYYDSNAYFDE (SEQ ID NO: 39). The light chain CDRs of the TCN-717 (6358_H17) antibody have the following sequences per Kabat definition: CDR 1: SGDLENTLVC (SEQ ID NO: 46), CDR 2: QDSKRPS (SEQ ID NO: 47), and CDR 3: QTWHRSTAQYV (SEQ ID NO: 48).

The heavy chain CDRs of the TCN-717 (6358_H17) antibody have the following sequences per Chothia definition: CDR 1: MGSILQND (SEQ ID NO: 40), CDR 2: SVHYRQKSY (SEQ ID NO: 41), and CDR 3: HNREDYYDSNAYFDE (SEQ ID NO: 39). The light chain CDRs of the TCN-717 (6358_H17) antibody have the following sequences per Chothia definition: CDR 1: SGDLENTLVC (SEQ ID NO: 46), CDR 2: QDSKRPS (SEQ ID NO: 47), and CDR 3: QTWHRSTAQYV (SEQ ID NO: 48).

The TCN-722 (6385_L22) antibody includes a heavy chain variable region (SEQ ID NO: 52), encoded by the nucleic acid sequence shown in SEQ ID NO: 50, and a light chain variable region (SEQ ID NO: 61) encoded by the nucleic acid sequence shown in SEQ ID NO: 59.

The heavy chain CDRs of the TCN-722 (6385_L22) antibody have the following sequences per Kabat definition: CDR 1: SNDQYWA (SEQ ID NO: 53), CDR 2: SVHYR- RRNYYSPSLES (SEQ ID NO: 54), and CDR 3: HNWEDYYESNAYFDY (SEQ ID NO: 55). The light chain CDRs of the TCN-722 (6385_L22) antibody have the following sequences per Kabat definition: CDR 1: SGDQLENTFVC (SEQ ID NO: 62), CDR 2: QGSKRPS (SEQ ID NO: 63), and CDR 3: QAWDRSTAHYV (SEQ ID NO: 64).

The heavy chain CDRs of the TCN-722 (6385_L22) antibody have the following sequences per Chothia definition: CDR 1: GDSLLSND (SEQ ID NO: 56), CDR 2: SVHYRRNY (SEQ ID NO: 57), and CDR 3: HNWEDYYESNAYFDY (SEQ ID NO: 55). The light chain CDRs of the TCN-722 (6385_L22) antibody have the following sequences per Chothia definition: CDR 1: SGDQLENTFVC (SEQ ID NO: 62), CDR 2: QGSKRPS (SEQ ID NO: 63), and CDR 3: QAWDRSTAHYV (SEQ ID NO: 64).

In one aspect, an antibody according to the invention contains a heavy chain having the amino acid sequence of SEQ ID NOs: 3, 19, 35, or 51, and a light chain having the amino acid sequence of SEQ ID NOs: 12, 28, 44, or 60. Alternatively, an antibody according to the invention contains a heavy chain variable region having the amino acid sequence of SEQ ID NOs: 4, 20, 36, or 52, and a light chain variable region having the amino acid sequence of SEQ ID NOs: 13, 29, 45, or 61.

In another aspect, an antibody according to the invention contains a heavy chain having the amino acid sequence encoded by the nucleic acid sequence of SEQ ID NOs: 1, 17, 33, or 49, and a light chain having the amino acid sequence encoded by the nucleic acid sequence of SEQ ID NOs: 10, 26, 42, or 58. Alternatively, an antibody according to the invention contains a heavy chain variable region having the amino acid sequence encoded by the nucleic acid sequence of SEQ ID NOs: 2, 18, 34, or 50 and a light chain variable region having the amino acid sequence encoded by the nucleic acid sequence of SEQ ID NOs: 11, 27, 43, or 59. Furthermore, an antibody according to the invention contains a heavy chain having the amino acid sequence encoded by a nucleic acid sequence of SEQ ID NOs: 2, 18, 34, or 50, which contains a silent or degenerate mutation, and a light chain having the amino acid sequence encoded by the nucleic acid sequence of SEQ ID NOs: 11, 27, 43, or 59, which contains a silent or degenerate mutation. Silent and degenerate mutations alter the nucleic acid sequence, but do not alter the resultant amino acid sequence.

Preferably the three heavy chain CDRs include an amino acid sequence of at least 90%, 92%, 95%, 97%, 98%, 99%, or more identical to the amino acid sequences of SEQ ID NOs: 5, 6, 7, 21, 22, 23, 37, 38, 39, 53, 54, or 55 (as determined by the Kabat method) or 8, 9, 7, 24, 25, 23, 40, 41, 39, 56, 57, or 55 (as determined by the Chothia method) and a light chain with three CDRs that include an amino acid sequence of at least 90%, 92%, 95%, 97%, 98%, 99%, or more identical to the amino acid sequence of 14, 15, 16, 30, 31, 32, 46, 47, 48, 62, 63, or 64 (as determined by the Kabat or Chothia method).

The heavy chain of the anti-HRV monoclonal antibody is derived from a germ line variable (V) gene such as, for example, the IGHV4-34*01, IGHV4-34*02, IGHV3-64*05, IGHV3-64*03, IGHV4-39*07 germline genes.

The anti-HRV antibodies of the invention include a variable heavy chain ($V_H$) region encoded by human IGHV4-34*01, IGHV4-34*02, IGHV3-64*05, IGHV3-64*03, IGHV4-39*07 germline gene sequences. The germline IGHV4-34*01, IGHV4-34*02, IGHV3-64*05, IGHV3-64*03, IGHV4-39*07 gene sequences are shown, e.g., in Accession numbers AB019439, M99684, M77301, M77298, X92259, AM940222, AM940222. The anti-HRV antibodies of the invention include a $V_H$ region that is encoded by a nucleic acid sequence that is at least 80% homologous to the IGHV4-34*01, IGHV4-34*02, IGHV3-64*05, IGHV3-64*03, IGHV4-39*07 germline gene sequences. Preferably, the nucleic acid sequence is at least 90%, 95%, 96%, 97% homologous to the IGHV4-34*01, IGHV4-34*02, IGHV3-64*05, IGHV3-64*03, IGHV4-39*07 germline gene sequences, and more preferably, at least 98%, 99% homologous to the IGHV4-34*01, IGHV4-34*02, IGHV3-64*05, IGHV3-64*03, IGHV4-39*07 germline gene sequences. The $V_H$ region of the anti-HRV antibody is at least 80% homologous to the amino acid sequence of the $V_H$ region encoded by the IGHV4-34*01, IGHV4-34*02, IGHV3-64*05, IGHV3-64*03, IGHV4-39*07 $V_H$ germline gene sequences. Preferably, the amino acid sequence of $V_H$ region of the anti-HRV antibody is at least 90%, 95%, 96%, 97% homologous to the amino acid sequence encoded by the IGHV4-34*01, IGHV4-34*02, IGHV3-64*05, IGHV3-64*03, IGHV4-39*07 germline gene sequences, and more preferably, at least 98%, 99% homologous to the sequence encoded by the IGHV4-34*01, IGHV4-34*02, IGHV3-64*05, IGHV3-64*03, IGHV4-39*07 germline gene sequences.

The light chain of the anti-HRV monoclonal antibody is derived from a germ line variable (V) gene such as, for example, the IGLV1-51*02, IGLV1-51*01, IGKV3-20*01, IGLV3-1*01 germline genes.

The anti-HRV antibodies of the invention also include a variable light chain ($V_L$) region encoded by human IGLV1-51*02, IGLV1-51*01, IGKV3-20*01, IGLV3-1*01 germline gene sequences. The human IGLV1-51*02, IGLV1-51*01, IGKV3-20*01, IGLV3-1*01 $V_L$ germline gene sequences are shown, e.g., Accession numbers M30446, Z73661, X12686, X57826.

The anti-HRV antibodies include a $V_L$ region that is encoded by a nucleic acid sequence that is at least 80% homologous to the IGLV1-51*02, IGLV1-51*01, IGKV3-20*01, IGLV3-1*01 germline gene sequences. Preferably, the nucleic acid sequence is at least 90%, 95%, 96%, 97% homologous to the IGLV1-51*02, IGLV1-51*01, IGKV3-20*01, IGLV3-1*01 germline gene sequences, and more preferably, at least 98%, 99% homologous to the IGLV1-51*02, IGLV1-51*01, IGKV3-20*01, IGLV3-1*01 germline gene sequences. The $V_L$ region of the anti-HRV antibody is at least 80% homologous to the amino acid sequence of the $V_L$ region encoded the IGLV1-51*02, IGLV1-51*01, IGKV3-20*01, IGLV3-1*01 germline gene sequences. Preferably, the amino acid sequence of $V_L$ region of the anti-HRV antibody is at least 90%, 95%, 96%, 97% homologous to the amino acid sequence encoded by the IGLV1-51*02, IGLV1-51*01, IGKV3-20*01, IGLV3-1*01 germline gene sequences, and more preferably, at least 98%, 99% homologous to the sequence encoded by the IGLV1-51*02, IGLV1-51*01, IGKV3-20*01, IGLV3-1*01 germline gene sequences.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

As mentioned above, the antibodies of the invention can be used to map the epitopes to which they bind. Applicants have discovered that antibodies TCN-711 (6893_E11), TCN-716 (6362_F16), TCN-717 (6358_H17), and TCN-722 (6385_L22) neutralize HRV. Although the Applicant does not wish to be bound by this theory, it is postulated that the antibodies TCN-711 (6893_E11), TCN-716 (6362_F16), TCN-717 (6358_H17), and TCN-722 (6385_L22) bind to one or more conformational epitopes formed by HRV-encoded proteins.

The epitopes recognized by these antibodies may have a number of uses. The epitopes and mimotopes in purified or synthetic form can be used to raise immune responses (i.e. as a vaccine, or for the production of antibodies for other uses) or for screening patient serum for antibodies that immunoreact with the epitopes or mimotopes. Preferably, such an epitope or mimotope, or antigen comprising such an epitope or mimotope is used as a vaccine for raising an immune response. The antibodies of the invention can also be used in a method to monitor the quality of vaccines in particular to check that the antigen in a vaccine contains the correct immunogenic epitope in the correct conformation.

The epitopes may also be useful in screening for ligands that bind to said epitopes. Such ligands preferably block the epitopes and thus prevent infection. Such ligands are encompassed within the scope of the invention.

Standard techniques of molecular biology may be used to prepare DNA sequences coding for the antibodies or fragments of the antibodies of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, HEK293T, PER.C6, myeloma or hybridoma cells.

The present invention also provides a process for the production of an antibody molecule according to the present invention comprising culturing a host cell comprising a vector of the present invention under conditions suitable for leading to expression of protein from DNA encoding the antibody molecule of the present invention, and isolating the antibody molecule. The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a cell, and ii) isolating the expressed antibody product. Additionally, the method may include iii) purifying the antibody. Transformed B cells are screened for those producing antibodies of the desired antigen specificity, and individual B cell clones can then be produced from the positive cells. The screening step may be carried out by ELISA, by staining of tissues or cells (including transfected cells), a neutralization assay or one of a number of other methods known in the art for identifying desired antigen specificity. The assay may select on the basis of simple antigen recognition, or may select on the additional basis of a desired function e.g. to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

The cloning step for separating individual clones from the mixture of positive cells may be carried out using limiting dilution, micromanipulation, single cell deposition by cell sorting or another method known in the art. Preferably the cloning is carried out using limiting dilution.

The immortalized B cell clones of the invention can be used in various ways e.g. as a source of monoclonal antibodies, as a source of nucleic acid (DNA or mRNA) encoding a monoclonal antibody of interest, for research, etc.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention.

The term "antibody" (Ab) as used herein includes monoclonal antibodies, polyclonal antibodies, multispecific antibodies (e.g., bispecific antibodies), and antibody fragments, as long as they exhibit the desired biological activity. The term "immunoglobulin" (Ig) is used interchangeably with "antibody" herein.

A "neutralizing antibody" may inhibit the entry of HRV virus.

By "broad and potent neutralizing antibodies" are meant antibodies that neutralize more than one HRV virus species (from diverse clades and different strains within a clade) in a neutralization assay. A broad neutralizing antibody may neutralize at least 2, 3, 4, 5, 6, 7, 8, 9 or more different strains or serotypes of HRV, the strains belonging to the same or different clades. A broad neutralizing antibody may neutralize multiple HRV serotypes belonging to at least 2, 3, or 4, different clades. Preferably, the half-maximal inhibitory concentration of the monoclonal antibody may be equal to or less than about 100 ng/ml to neutralize about 50% of the input virus in the neutralization assay. However, the half-maximal inhibitory concentration of the monoclonal antibody may be equal to or less than about 100 ng/ml, 90 ng/ml, 80 ng/ml, 70 ng/ml, 60 ng/ml, 50 ng/ml, 40 ng/ml, 30 ng/ml, 20 ng/ml, 10 ng/ml, 1 ng/ml, or any concentration in between to neutralize about 50% of the input virus in the neutralization assay.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the α and γ chains and four $C_H$ domains for μ and ε isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Ten and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

In some aspects, the alternative EBV immortalization method described in WO2004/076677 is used. Using this method, B-cells producing the antibody of the invention can be transformed with EBV in the presence of a polyclonal B cell activator. Transformation with EBV is a standard technique and can easily be adapted to include polyclonal B cell activators. Additional stimulants of cellular growth and differentiation may be added during the transformation step to further enhance the efficiency. These stimulants may be cytokines such as IL-2 and IL-15. In a particularly preferred aspect, IL-2 is added during the immortalization step to further improve the efficiency of immortalization, but its use is not essential.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable region antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable region antigen binding sequence of one antibody class or subclass and another sequence, e.g., FR or C region sequence, derived from another antibody class or subclass. Chimeric antibodies of interest herein also include those containing variable region antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable region. Humanization is traditionally performed following the method of Winter and co-workers (Jones et al., Nature, 321:522-525 (1986); Reichmann et al., Nature, 332:323-327 (1988); Verhoeyen et al., Science, 239: 1534-1536 (1988)), by substituting import hypervariable region sequences for the corresponding sequences of a human antibody. Accordingly, such "humanized" antibodies are chimeric antibodies (U.S. Pat. No. 4,816,567), wherein substantially less than an intact human variable region has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', $F(ab')_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, $Fc_\epsilon RI$.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from 11 kDa to 15 kDa. dAbs are the robust variable regions of the heavy and light chains of immunoglobulins (VH and VL respectively). They are highly expressed in microbial cell culture, show favorable biophysical properties including solubility and temperature stability, and are well suited to selection and affinity maturation by in vitro selection systems such as phage display. dAbs are bioactive as monomers and, owing to their small size and inherent stability, can be formatted into larger molecules to create drugs with prolonged serum half-lives or other pharmacological activities. Examples of this technology have been described in WO9425591 for antibodies derived from Camelidae heavy chain Ig, as well in US20030130496 describing the isolation of single domain fully human antibodies from phage libraries.

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HRV antibody specifically binds to an HRV polypeptide if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (Ann. N.Y. Acad. Sci. USA 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An "antibody that inhibits the growth of infected cells" or a "growth inhibitory" antibody is one that binds to and results in measurable growth inhibition of infected cells expressing or capable of expressing an HRV epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 µg/ml or about 0.5 nM to 200 nM in cell culture, where the growth inhibition is determined 1-10 days after exposure of the infected cells to the antibody. Growth inhibition of infected cells in vivo can be determined in various ways known in the art.

The antibody is growth inhibitory in vivo if administration of the antibody at about 1 μg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 4 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells.

Alternatively, or additionally, ADCC activity of the molecule of interest may be assessed in vivo, e.g., in a animal model such as that disclosed in Clynes et al., *Proc. Natl. Acad. Sci*. (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain (see review M. in Daeron, Annu Rev. Immunol. 15:203-234 (1997)). FcRs are reviewed in Ravetch and Kinet, Annu Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

A "mammal" for purposes of treating an infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™

The term "cytotoxic agent" as used herein refers to a substance that inhibits or prevents the function of cells and/or causes destruction of cells. The term is intended to include radioactive isotopes (e.g., $At^{21}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classical M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or HRV-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, it's underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below. As used in this specification and the appended claims, the singular forms "a," "an" and "the" include plural references unless the content clearly dictates otherwise.

The invention also includes nucleic acid sequences encoding part or all of the light and heavy chains and CDRs of the present invention. Due to redundancy of the genetic code, variants of these sequences will exist that encode the same amino acid sequences.

Variant antibodies are also included within the scope of the invention. Thus, variants of the sequences recited in the application are also included within the scope of the invention. Further variants of the antibody sequences having improved affinity may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody.

Preferably, such variant antibody sequences will share 70% or more (i.e. 80, 85, 90, 95, 97, 98, 99% or more) sequence identity with the sequences recited in the application. Preferably such sequence identity is calculated with regard to the full length of the reference sequence (i.e. the sequence recited in the application). Preferably, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Further included within the scope of the invention are vectors such as expression vectors, comprising a nucleic acid sequence according to the invention. Cells transformed with such vectors are also included within the scope of the invention.

As will be understood by the skilled artisan, general description of antibodies herein and methods of preparing and using the same also apply to individual antibody polypeptide constituents and antibody fragments.

The antibodies of the present invention may be polyclonal or monoclonal antibodies. However, in preferred embodiments, they are monoclonal. In particular embodiments, antibodies of the present invention are human antibodies. Methods of producing polyclonal and monoclonal antibodies are known in the art and described generally, e.g., in U.S. Pat. No. 6,824,780.

Typically, the antibodies of the present invention are produced recombinantly, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or Primatized™. In practice, humanized antibodies are typically human antibodies in which some hypervariable region residues and possibly some FR residues are substituted by residues from analogous sites in rodent antibodies.

In the context of the present invention, chimeric antibodies also include human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences.

Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well: IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils and mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, comprise a variable light chain that is either kappa or lambda. The lambda chain may be any of subtype, including, e.g., lambda 1, lambda 2, lambda 3, and lambda 4.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')$_2$ and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

In certain embodiments, antibodies of the present invention are bispecific or multi-specific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-HRV arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the infected cell. Bispecific antibodies may also be used to localize cytotoxic agents to infected cells. These antibodies possess an HRV-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HRV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from $E.\ coli$, which can be chemically coupled to form bispecific antibodies. Shalaby et al., J. Exp. Med., 175: 217-225 (1992) describe the production of a humanized bispecific antibody F(ab')$_2$ molecule. Each Fab' fragment was separately secreted from $E.\ coli$ and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1)$_n$-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH—CH$_1$-flexible linker-VH—CH$_1$-Fc region chain; or VH—CH$_1$—VH—CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Antibodies of the invention further include single chain antibodies. In particular embodiments, antibodies of the invention are internalizing antibodies.

Amino acid sequence modification(s) of the antibodies described herein are contemplated. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics. The amino acid changes also may alter post-translational processes of the antibody, such as changing the number or position of glycosylation sites. Any of the variations and modifications described above for polypeptides of the present invention may be included in antibodies of the present invention.

A useful method for identification of certain residues or regions of an antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody include the fusion to the N- or C-terminus of the antibody to an enzyme (e.g., for ADEPT) or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative and non-conservative substitutions are contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and an antigen or infected cell. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibody of the invention is modified with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148:2918-2922 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies of the present invention may also be modified to include an epitope tag or label, e.g., for use in purification or diagnostic applications. The invention also pertains to therapy with immunoconjugates comprising an antibody conjugated to an anti-cancer agent such as a cytotoxic agent or a growth inhibitory agent. Chemotherapeutic agents useful in the generation of such immunoconjugates have been described above.

Conjugates of an antibody and one or more small molecule toxins, such as a calicheamicin, maytansinoids, a trichothene, and CC1065, and the derivatives of these toxins that have toxin activity, are also contemplated herein.

In one preferred embodiment, an antibody (full length or fragments) of the invention is conjugated to one or more maytansinoid molecules. Maytansinoids are mitototic inhibitors that act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, Cancer Research 52: 127-131 (1992); U.S. Pat. No. 5,208,020) may be used.

Another immunoconjugate of interest comprises an antibody conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Another drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Examples of other agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof that can be used include, e.g., diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232.

The present invention further includes an immunoconjugate formed between an antibody and a compound with nucleolytic activity (e.g., a ribonuclease or a DNA endonuclease such as a deoxyribonuclease; DNase).

For selective destruction of infected cells, the antibody includes a highly radioactive atom. A variety of radioactive isotopes are available for the production of radioconjugated anti-PSCA antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as Magnetic Resonance Imaging, MRI), such as iodine-123, iodine-131, indium-111, fluorine-19, carbon-13, nitrogen-15, oxygen-17, gadolinium, manganese or iron.

The radio- or other label is incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Alternatively, a fusion protein comprising the antibody and cytotoxic agent is made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. The antibodies of the present invention are also used in antibody dependent enzyme mediated prodrug therapy (ADET) by conjugating the antibody to a prodrug-activating enzyme which converts a prodrug (e.g., a peptidyl chemotherapeutic agent, see WO81/01145) to an active anti-cancer drug (see, e.g., WO 88/07378 and U.S. Pat. No. 4,975, 278).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to an infected cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies disclosed herein are also formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81 (19) 1484 (1989). Antibodies of the present invention, or fragments thereof, may possess any of a variety of biological or functional characteristics. In certain embodiments, these antibodies are HRV protein specific antibodies, indicating that they specifically bind to or preferentially bind to HRV as compared to a normal control cell.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

HRV-expressing cells or virus described above are used to screen the biological sample obtained from a patient infected with HRV for the presence of antibodies that preferentially bind to the cell expressing HRV polypeptides using standard biological techniques. For example, in certain embodiments, the antibodies may be labeled, and the presence of label associated with the cell detected, e.g., using FMAT or FACs analysis. In particular embodiments, the biological sample is blood, serum, plasma, bronchial lavage, or saliva. Methods of the present invention may be practiced using high throughput techniques.

Identified human antibodies may then be characterized further. For example the particular conformational epitopes with in the HRV polypeptides that are necessary or sufficient for binding of the antibody may be determined, e.g., using site-directed mutagenesis of expressed HRV polypeptides. These methods may be readily adapted to identify human antibodies that bind any protein expressed on a cell surface. Furthermore, these methods may be adapted to determine binding of the antibody to the virus itself, as opposed to a cell expressing a recombinant HRV protein or infected with the virus.

Polynucleotide sequences encoding the antibodies, variable regions thereof, or antigen-binding fragments thereof may be subcloned into expression vectors for the recombinant production of human anti-HRV antibodies. In one embodiment, this is accomplished by obtaining mononuclear cells from the patient from the serum containing the identified HRV antibody was obtained; producing B cell clones from the mononuclear cells; inducing the B cells to become antibody-producing plasma cells; and screening the supernatants produced by the plasma cells to determine if it contains the HRV antibody. Once a B cell clone that produces an HRV antibody is identified, reverse-transcription polymerase chain reaction (RT-PCR) is performed to clone the DNAs encoding the variable regions or portions thereof of the HRV antibody. These sequences are then subcloned into expression vectors suitable for the recombinant production of human HRV antibodies. The binding specificity may be confirmed by determining the recombinant antibody's ability to bind cells expressing HRV polypeptide.

In particular embodiments of the methods described herein, B cells isolated from peripheral blood or lymph nodes are sorted, e.g., based on their being CD19 positive, and plated, e.g., as low as a single cell specificity per well, e.g., in 96, 384, or 1536 well configurations. The cells are induced to differentiate into antibody-producing cells, e.g., plasma cells, and the culture supernatants are harvested and tested for binding to cells expressing the infectious agent polypeptide on their surface using, e.g., FMAT or FACS analysis. Positive wells are then subjected to whole well RT-PCR to amplify heavy and light chain variable regions of the IgG molecule expressed by the clonal daughter plasma cells. The resulting PCR products encoding the heavy and light chain variable regions, or portions thereof, are subcloned into human antibody expression vectors for recombinant expression. The resulting recombinant antibodies are then tested to confirm their original binding specificity and may be further tested for pan-specificity across various strains of isolates of the infectious agent.

Thus, in one embodiment, a method of identifying HRV antibodies is practiced as follows. First, full length or approximately full length HRV cDNAs are transfected into a cell line for expression of HRV polypeptides. Secondly, individual human plasma or sera samples are tested for antibodies that bind the cell-expressed HRV polypeptides. And lastly, MAbs derived from plasma- or serum-positive individuals are characterized for binding to the same cell-expressed HRV polypeptides. Further definition of the fine specificities of the MAbs can be performed at this point.

Polynucleotides that encode the HRV antibodies or portions thereof of the present invention may be isolated from cells expressing HRV antibodies, according to methods available in the art and described herein, including amplification by polymerase chain reaction using primers specific for conserved regions of human antibody polypeptides. For example, light chain and heavy chain variable regions may be cloned from the B cell according to molecular biology techniques described in WO 92/02551; U.S. Pat. No. 5,627,052; or Babcook et al., *Proc. Natl. Acad. Sci. USA* 93:7843-48 (1996). In certain embodiments, polynucleotides encoding all or a region of both the heavy and light chain variable regions of the IgG molecule expressed by the clonal daughter plasma cells expressing the HRV antibody are subcloned and sequenced. The sequence of the encoded polypeptide may be readily determined from the polynucleotide sequence.

Isolated polynucleotides encoding a polypeptide of the present invention may be subcloned into an expression vector to recombinantly produce antibodies and polypeptides of the present invention, using procedures known in the art and described herein.

Binding properties of an antibody (or fragment thereof) to HRV polypeptides or HRV infected cells or tissues may generally be determined and assessed using immunodetection methods including, for example, immunofluorescence-based assays, such as immuno-histochemistry (IHC) and/or fluorescence-activated cell sorting (FACS). Immunoassay methods may include controls and procedures to determine whether antibodies bind specifically to HRV polypeptides from one or more specific clades or strains of HRV, and do not recognize or cross-react with normal control cells.

Following pre-screening of serum to identify patients that produce antibodies to an infectious agent or polypeptide thereof, e.g., HRV, the methods of the present invention typically include the isolation or purification of B cells from a biological sample previously obtained from a patient or subject. The patient or subject may be currently or previously diagnosed with or suspect or having a particular disease or infection, or the patient or subject may be considered free or a particular disease or infection. Typically, the patient or subject is a mammal and, in particular embodiments, a human. The biological sample may be any sample that contains B cells, including but not limited to, lymph node or lymph node tissue, pleural effusions, peripheral blood, ascites, tumor tissue, or cerebrospinal fluid (CSF). In various embodiments, B cells are isolated from different types of biological samples, such as a biological sample affected by a particular disease or infection. However, it is understood that any biological sample comprising B cells may be used for any of the embodiments of the present invention.

Once isolated, the B cells are induced to produce antibodies, e.g., by culturing the B cells under conditions that support B cell proliferation or development into a plasmacyte, plasmablast, or plasma cell. The antibodies are then screened, typically using high throughput techniques, to identify an antibody that specifically binds to a target antigen, e.g., a particular tissue, cell, infectious agent, or polypeptide. In certain embodiments, the specific antigen, e.g., cell surface polypeptide bound by the antibody is not known, while in other embodiments, the antigen specifically bound by the antibody is known.

According to the present invention, B cells may be isolated from a biological sample, e.g., a tumor, tissue, peripheral blood or lymph node sample, by any means known and available in the art. B cells are typically sorted by FACS based on the presence on their surface of a B cell-specific marker, e.g., CD19, CD138, and/or surface IgG. However, other methods known in the art may be employed, such as, e.g., column purification using CD19 magnetic beads or IgG-specific magnetic beads, followed by elution from the column. However, magnetic isolation of B cells utilizing any marker may result in loss of certain B cells. Therefore, in certain embodiments, the isolated cells are not sorted but, instead, phicol-purified mononuclear cells isolated from tumor are directly plated to the appropriate or desired number of specificities per well.

In order to identify B cells that produce an infectious agent-specific antibody, the B cells are typically plated at low density (e.g., a single cell specificity per well, 1-10 cells per well, 10-100 cells per well, 1-100 cells per well, less than 10 cells per well, or less than 100 cells per well) in multi-well or microtiter plates, e.g., in 96, 384, or 1536 well configurations. When the B cells are initially plated at a density greater than one cell per well, then the methods of the present invention may include the step of subsequently diluting cells in a well identified as producing an antigen-specific antibody, until a single cell specificity per well is achieved, thereby facilitating the identification of the B cell that produces the antigen-specific antibody. Cell supernatants or a portion thereof and/or cells may be frozen and stored for future testing and later recovery of antibody polynucleotides.

In certain embodiments, the B cells are cultured under conditions that favor the production of antibodies by the B cells. For example, the B cells may be cultured under conditions favorable for B cell proliferation and differentiation to yield antibody-producing plasmablast, plasmacytes, or plasma cells. In particular embodiments, the B cells are cultured in the presence of a B cell mitogen, such as lipopolysaccharide (LPS) or CD40 ligand. In one specific embodiment, B cells are differentiated to antibody-producing cells by culturing them with feed cells and/or other B cell activators, such as CD40 ligand.

Cell culture supernatants or antibodies obtained therefrom may be tested for their ability to bind to a target antigen, using routine methods available in the art, including those described herein. In particular embodiments, culture supernatants are tested for the presence of antibodies that bind to a target antigen using high-throughput methods. For example, B cells may be cultured in multi-well microtiter dishes, such that robotic plate handlers may be used to simultaneously sample multiple cell supernatants and test for the presence of antibodies that bind to a target antigen. In particular embodiments, antigens are bound to beads, e.g., paramagnetic or latex beads) to facilitate the capture of antibody/antigen complexes. In other embodiments, antigens and antibodies are fluorescently labeled (with different labels) and FACS analysis is performed to identify the presence of antibodies that bind to target antigen. In one embodiment, antibody binding is determined using FMAT™ analysis and instrumentation (Applied Biosystems, Foster City, Calif.). FMAT™ is a fluorescence macro-confocal platform for high-throughput screening, which mix-and-read, non-radioactive assays using live cells or beads.

In the context of comparing the binding of an antibody to a particular target antigen (e.g., a biological sample such as infected tissue or cells, or infectious agents) as compared to a control sample (e.g., a biological sample such as uninfected cells, or a different infectious agent), in various embodiments, the antibody is considered to preferentially bind a particular target antigen if at least two-fold, at least three-fold, at least five-fold, or at least ten-fold more antibody binds to the particular target antigen as compared to the amount that binds a control sample.

Polynucleotides encoding antibody chains, variable regions thereof, or fragments thereof, may be isolated from cells utilizing any means available in the art. In one embodiment, polynucleotides are isolated using polymerase chain reaction (PCR), e.g., reverse transcription-PCR (RT-PCR) using oligonucleotide primers that specifically bind to heavy or light chain encoding polynucleotide sequences or complements thereof using routine procedures available in the art. In one embodiment, positive wells are subjected to whole well RT-PCR to amplify the heavy and light chain variable regions of the IgG molecule expressed by the clonal daughter plasma cells. These PCR products may be sequenced.

The resulting PCR products encoding the heavy and light chain variable regions or portions thereof are then subcloned into human antibody expression vectors and recombinantly expressed according to routine procedures in the art (see, e.g., U.S. Pat. No. 7,112,439). The nucleic acid molecules encoding a tumor-specific antibody or fragment thereof, as described herein, may be propagated and expressed according to any of a variety of well-known procedures for nucleic acid excision, ligation, transformation, and transfection. Thus, in certain embodiments expression of an antibody fragment may be preferred in a prokaryotic host cell, such as *Escherichia coli* (see, e.g., Pluckthun et al., *Methods Enzymol.* 178:497-515 (1989)). In certain other embodiments, expression of the antibody or an antigen-binding fragment thereof may be preferred in a eukaryotic host cell, including yeast (e.g., *Saccharomyces cerevisiae, Schizosaccharomyces pombe*, and *Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the tumor-specific antibody (or fragment thereof) may be inserted. The regulatory elements will vary according to the particular host.

One or more replicable expression vectors containing a polynucleotide encoding a variable and/or constant region may be prepared and used to transform an appropriate cell line, for example, a non-producing myeloma cell line, such as a mouse NSO line or a bacterium, such as *E. coli*, in which production of the antibody will occur. In order to obtain efficient transcription and translation, the polynucleotide sequence in each vector should include appropriate regulatory sequences, particularly a promoter and leader sequence operatively linked to the variable region sequence. Particular methods for producing antibodies in this way are generally well known and routinely used. For example, molecular biology procedures are described by Sambrook et al. (*Molecular Cloning, A Laboratory Manual,* 2nd ed., Cold Spring Harbor Laboratory, New York, 1989; see also Sambrook et al., 3rd ed., Cold Spring Harbor Laboratory, New York, (2001)). While not required, in certain embodiments, regions of polynucleotides encoding the recombinant antibodies may be sequenced. DNA sequencing can be performed as described in Sanger et al. (*Proc. Natl. Acad. Sci. USA* 74:5463 (1977)) and the Amersham International plc sequencing handbook and including improvements thereto.

In particular embodiments, the resulting recombinant antibodies or fragments thereof are then tested to confirm their original specificity and may be further tested for pan-specificity, e.g., with related infectious agents. In particular embodiments, an antibody identified or produced according to methods described herein is tested for cell killing via antibody dependent cellular cytotoxicity (ADCC) or apoptosis, and/or well as its ability to internalize.

The present invention, in other aspects, provides polynucleotide compositions. In preferred embodiments, these polynucleotides encode a polypeptide of the invention, e.g., a region of a variable chain of an antibody that binds to HRV. Polynucleotides of the invention are single-stranded (coding or antisense) or double-stranded DNA (genomic, cDNA or synthetic) or RNA molecules. RNA molecules include, but are not limited to, HnRNA molecules, which contain introns and correspond to a DNA molecule in a one-to-one manner, and mRNA molecules, which do not contain introns. Alternatively, or in addition, coding or non-coding sequences are present within a polynucleotide of the present invention. Also alternatively, or in addition, a polynucleotide is linked to other molecules and/or support materials of the invention. Polynucleotides of the invention are used, e.g., in hybridization assays to detect the presence of an HRV antibody in a biological sample, and in the recombinant production of polypeptides of the invention. Further, the invention includes all polynucleotides that encode any polypeptide of the present invention.

In other related embodiments, the invention provides polynucleotide variants having substantial identity to the sequences of SEQ ID NOs: 1, 2, 10, 11, 17, 18, 26, 27, 33, 34, 42, 43, 49, 50, 58, 59, for example those comprising at least 70% sequence identity, preferably at least 75%, 80%, 85%, 90%, 95%, 96%, 97%, 98%, or 99% or higher, sequence identity compared to a polynucleotide sequence of this invention, as determined using the methods described herein, (e.g., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

Typically, polynucleotide variants contain one or more substitutions, additions, deletions and/or insertions, preferably such that the immunogenic binding properties of the polypeptide encoded by the variant polynucleotide is not substantially diminished relative to a polypeptide encoded by a polynucleotide sequence specifically set forth herein.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. As used herein, the term "intermediate lengths" is meant to describe any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In preferred embodiments, the polypeptide encoded by the polynucleotide variant or fragment has the same binding specificity (i.e., specifically or preferentially binds to the same epitope or HRV strain) as the polypeptide encoded by the native polynucleotide. In certain preferred embodiments, the polynucleotides described above, e.g., polynucleotide variants, fragments and hybridizing sequences, encode polypeptides that have a level of binding activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. A nucleic acid fragment of almost any length is employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are included in many implementations of this invention.

It will be appreciated by those of ordinary skill in the art that, as a result of the degeneracy of the genetic code, there are multiple nucleotide sequences that encode a polypeptide as described herein. Some of these polynucleotides bear minimal homology to the nucleotide sequence of any native gene. Nonetheless, polynucleotides that encode a polypeptide of the present invention but which vary due to differences in codon usage are specifically contemplated by the invention. Further, alleles of the genes including the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In certain embodiments of the present invention, mutagenesis of the disclosed polynucleotide sequences is performed in order to alter one or more properties of the encoded polypeptide, such as its binding specificity or binding strength. Techniques for mutagenesis are well-known in the art, and are widely used to create variants of both polypeptides and polynucleotides. A mutagenesis approach, such as site-specific mutagenesis, is employed for the preparation of variants and/or derivatives of the polypeptides described herein. By this approach, specific modifications in a polypeptide sequence are made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences include the nucleotide sequence of the desired mutation, as well as a sufficient number of adjacent nucleotides, to provide a primer sequence of sufficient size and sequence complexity to form a stable duplex on both sides of the deletion junction being traversed. Mutations are employed in a selected polynucleotide sequence to improve, alter, decrease, modify, or otherwise change the properties of the polynucleotide itself, and/or alter the properties, activity, composition, stability, or primary sequence of the encoded polypeptide.

In other embodiments of the present invention, the polynucleotide sequences provided herein are used as probes or primers for nucleic acid hybridization, e.g., as PCR primers. The ability of such nucleic acid probes to specifically hybridize to a sequence of interest enables them to detect the presence of complementary sequences in a given sample. However, other uses are also encompassed by the invention, such as the use of the sequence information for the preparation of mutant species primers, or primers for use in preparing other genetic constructions. As such, nucleic acid segments of the invention that include a sequence region of at least about a 15-nucleotide long contiguous sequence that has the same sequence as, or is complementary to, a 15 nucleotide long contiguous sequence disclosed herein is particularly useful. Longer contiguous identical or complementary sequences, e.g., those of about 20, 30, 40, 50, 100, 200, 500, 1000 (including all intermediate lengths) including full length sequences, and all lengths in between, are also used in certain embodiments.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting, and/or primers for use in, e.g., polymerase chain reaction (PCR). The total size of fragment, as well as the size of the complementary stretch (es), ultimately depends on the intended use or application of the particular nucleic acid segment. Smaller fragments are generally used in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 12 bases in length are generally preferred, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer where desired, are generally preferred.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences is governed by various factors. For example, one may wish to employ primers from towards the termini of the total sequence.

Polynucleotide of the present invention, or fragments or variants thereof, are readily prepared by, for example, directly synthesizing the fragment by chemical means, as is commonly practiced using an automated oligonucleotide synthesizer. Also, fragments are obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

The invention provides vectors and host cells comprising a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors comprising a polynucleotide of the present invention are vectors suitable for propagation or replication of the polynucleotide, or vectors suitable for expressing a polypeptide of the present invention. Such vectors are known in the art and commercially available.

Polynucleotides of the present invention are synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

Within one embodiment, the variable regions of a gene expressing a monoclonal antibody of interest are amplified from a hybridoma cell using nucleotide primers. These primers are synthesized by one of ordinary skill in the art, or may be purchased from commercially available sources (see, e.g., Stratagene (La Jolla, Calif.), which sells primers for amplifying mouse and human variable regions. The primers are used to amplify heavy or light chain variable regions, which are then inserted into vectors such as ImmunoZAP™ H or ImmunoZAP™ L (Stratagene), respectively. These vectors are then introduced into E. coli, yeast, or mammalian-based systems for expression. Large amounts of a single-chain protein containing a fusion of the $V_H$ and $V_L$ domains are produced using these methods (see Bird et al., Science 242:423-426 (1988)).

The "control elements" or "regulatory sequences" present in an expression vector are those non-translated regions of the vector, e.g., enhancers, promoters, 5' and 3' untranslated regions, that interact with host cellular proteins to carry out transcription and translation. Such elements may vary in their strength and specificity. Depending on the vector system and host utilized, any number of suitable transcription and translation elements, including constitutive and inducible promoters, is used.

Examples of promoters suitable for use with prokaryotic hosts include the phoa promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also usually contain a Shine-Dalgarno sequence operably linked to the DNA encoding the polypeptide. Inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like are used.

A variety of promoter sequences are known for eukaryotes and any are used according to the present invention. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells are controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40 (SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA-3.1 (Invitrogen, Carlsbad, Calif.), which includes a CMV promoter.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

In bacterial systems, any of a number of expression vectors is selected depending upon the use intended for the expressed polypeptide. For example, when large quantities are desired, vectors that direct high level expression of fusion proteins that are readily purified are used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264:5503-5509); and the like. pGEX Vectors (Promega, Madison, Wis.) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al. (supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) EMBO J. 6:307-311. Alternatively, plant promoters such as the small subunit of RUBISCO or heat shock promoters are used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide are cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses are then used to infect, for example, *S. frugiperda* cells or *Trichoplusia* larvae, in which the polypeptide of interest is expressed (Engelhard, E. K. et al. (1994) Proc. Natl. Acad. Sci. 91:3224-3227).

Specific initiation signals are also used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon are provided. Furthermore, the initiation codon is in the correct reading frame to ensure correct translation of the inserted polynucleotide. Exogenous translational elements and initiation codons are of various origins, both natural and synthetic.

Transcription of a DNA encoding a polypeptide of the invention is often increased by inserting an enhancer sequence into the vector. Many enhancer sequences are known, including, e.g., those identified in genes encoding globin, elastase, albumin, α-fetoprotein, and insulin. Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer is spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

Suitable host cells for cloning or expressing the DNA in the vectors herein are the prokaryote, yeast, plant or higher eukaryote cells described above. Examples of suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

*Saccharomyces cerevisiae*, or common baker's yeast, is the most commonly used among lower eukaryotic host microorganisms. However, a number of other genera, species, and strains are commonly available and used herein, such as *Schizosaccharomyces pombe; Kluyveromyces* hosts such as, e.g., K lactis, *K. fragilis* (ATCC 12,424), *K. bulgaricus* (ATCC 16,045), K wickeramii (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris*. (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

In certain embodiments, a host cell strain is chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing that cleaves a "prepro" form of the protein is also used to facilitate correct insertion, folding and/or function. Different host cells such as CHO, COS, HeLa, MDCK, HEK293, and WI38, which have specific cellular machinery and characteristic mechanisms for such post-translational activities, are chosen to ensure the correct modification and processing of the foreign protein.

Methods and reagents specifically adapted for the expression of antibodies or fragments thereof are also known and available in the art, including those described, e.g., in U.S. Pat. Nos. 4,816,567 and 6,331,415. In various embodiments, antibody heavy and light chains, or fragments thereof, are expressed from the same or separate expression vectors. In one embodiment, both chains are expressed in the same cell, thereby facilitating the formation of a functional antibody or fragment thereof.

Full length antibody, antibody fragments, and antibody fusion proteins are produced in bacteria, in particular when glycosylation and Fc effector function are not needed, such as when the therapeutic antibody is conjugated to a cytotoxic agent (e.g., a toxin) and the immunoconjugate by itself shows effectiveness in infected cell destruction. For expression of antibody fragments and polypeptides in bacteria, see, e.g., U.S. Pat. Nos. 5,648,237, 5,789,199, and 5,840,523, which describes translation initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out using a process similar to that used for purifying antibody expressed e.g., in CHO cells.

Suitable host cells for the expression of glycosylated polypeptides and antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses are used as the virus herein according to the present invention, particularly for transfection of *Spodoptera frugiperda* cells. Plant cell cultures of cotton, corn, potato, soybean, petunia, tomato, and tobacco are also utilized as hosts.

Methods of propagation of antibody polypeptides and fragments thereof in vertebrate cells in culture (tissue culture) are encompassed by the invention. Examples of mammalian host cell lines used in the methods of the invention are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

For long-term, high-yield production of recombinant proteins, stable expression is generally preferred. For example, cell lines that stably express a polynucleotide of interest are transformed using expression vectors that contain viral origins of replication and/or endogenous expression elements and a selectable marker gene on the same or on a separate vector. Following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells are proliferated using tissue culture techniques appropriate to the cell type.

A plurality of selection systems are used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes that are employed in tk⁻ or aprt⁻ cells, respectively. Also, antimetabolite, antibiotic or herbicide resistance is used as the basis for selection; for example, dhfr, which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al. (1981) *J. Mol. Biol.* 150:1-14); and als or pat, which confer resistance to chlorsulfuron and phosphinotricin acetyltransferase, respectively (Murry, supra). Additional selectable genes have been described. For example, trpB allows cells to utilize indole in place of tryptophan, and hisD allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression is confirmed. For example, if the sequence encoding a polypeptide is inserted within a marker gene sequence, recombinant cells containing sequences are identified by the absence of marker gene function. Alternatively, a marker gene is placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence are identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Nonlimiting examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide is preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

Various labels and conjugation techniques are known by those skilled in the art and are used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof are cloned into a vector for the production of an mRNA probe. Such vectors are known in the art, are commercially available, and are used to synthesize RNA probes in vitro by addition of an appropriate RNA polymerase such as T7, T3, or SP6 and labeled nucleotides. These procedures are conducted using a variety of commercially available kits. Suitable reporter molecules or labels, which are used include, but are not limited to, radionucleotides, enzymes, fluorescent, chemiluminescent, or chromogenic agents as well as substrates, cofactors, inhibitors, magnetic particles, and the like.

The polypeptide produced by a recombinant cell is secreted or contained intracellularly depending on the sequence and/or the vector used. Expression vectors containing polynucleotides of the invention are designed to contain signal sequences that direct secretion of the encoded polypeptide through a prokaryotic or eukaryotic cell membrane.

In certain embodiments, a polypeptide of the invention is produced as a fusion polypeptide further including a polypeptide domain that facilitates purification of soluble proteins. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Amgen, Seattle, Wash.). The inclusion of cleavable linker sequences such as those specific for Factor XA or enterokinase (Invitrogen. San Diego, Calif.) between the purification domain and the encoded polypeptide are used to facilitate purification. An exemplary expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors used for producing fusion proteins is provided in Kroll, D. J. et al. (1993; *DNA Cell Biol.* 12:441-453).

In certain embodiments, a polypeptide of the present invention is fused with a heterologous polypeptide, which may be a signal sequence, or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells, the signal sequence is selected, for example, from the group of the alkaline phosphatase, penicillinase, 1 pp, or heat-stable enterotoxin II leaders. For yeast secretion, the signal sequence is selected from, e.g., the yeast invertase leader, a factor leader (including *Saccharomyces* and *Kluyveromyces* α factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

When using recombinant techniques, the polypeptide or antibody is produced intracellularly, in the periplasmic space, or directly secreted into the medium. If the polypeptide or antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris is removed by centrifugation. Where the polypeptide or antibody is secreted into the medium, supernatants from such expression systems are generally first concentrated using a commercially available protein concentration filter, for example, an Amicon or Millipore Pellicon ultrafiltration unit. Optionally, a protease inhibitor such as PMSF is included in any of the foregoing steps to inhibit proteolysis and antibiotics are included to prevent the growth of adventitious contaminants.

The polypeptide or antibody composition prepared from the cells are purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the polypeptide or antibody. Protein A is used to purify antibodies or fragments thereof that are based on human $\gamma_1$, $\gamma_2$, or $\gamma_4$ heavy chains (Lindmark et al., J. Immunol. Meth. 62:1-13 (1983)). Protein G is recommended for all mouse isotypes and for human $\gamma_3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the polypeptide or antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide or antibody to be recovered.

Following any preliminary purification step(s), the mixture comprising the polypeptide or antibody of interest and contaminants are subjected to low pH hydrophobic interaction chromatography using an elution buffer at a pH between about 2.5-4.5, preferably performed at low salt concentrations (e.g., from about 0-0.25M salt).

The invention further includes pharmaceutical formulations including a polypeptide, antibody, or modulator of the present invention, at a desired degree of purity, and a pharmaceutically acceptable carrier, excipient, or stabilizer (Remingion's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions.

Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). In certain embodiments, the therapeutic formulation preferably comprises the polypeptide or antibody at a concentration of between 5-200 mg/ml, preferably between 10-100 mg/ml.

The formulations herein also contain one or more additional therapeutic agents suitable for the treatment of the particular indication, e.g., infection being treated, or to prevent undesired side-effects. Preferably, the additional therapeutic agent has an activity complementary to the polypeptide or antibody of the resent invention, and the two do not adversely affect each other. For example, in addition to the polypeptide or antibody of the invention, an additional or second antibody, anti-viral agent, anti-infective agent and/or cardioprotectant is added to the formulation. Such molecules are suitably present in the pharmaceutical formulation in amounts that are effective for the purpose intended.

The active ingredients, e.g., polypeptides and antibodies of the invention and other therapeutic agents, are also entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nano-particles and nanocapsules) or in macroemulsions. Such techniques are disclosed in Remingion's Pharmaceutical Sciences 16th edition, Osol, A. Ed. (1980).

Sustained-release preparations are prepared. Suitable examples of sustained-release preparations include, but are not limited to, semi-permeable matrices of solid hydrophobic polymers containing the antibody, which matrices are in the form of shaped articles, e.g., films, or microcapsules. Non-limiting examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxyburyric acid.

Formulations to be used for in vivo administration are preferably sterile. This is readily accomplished by filtration through sterile filtration membranes.

Antibodies of the invention can be coupled to a drug for delivery to a treatment site or coupled to a detectable label to facilitate imaging of a site comprising cells of interest, such as cells infected with HRV. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an HRV epitope) can be facilitated by attaching a detectable substance to the antibody. Suitable detection means include the use of labels such as radionucleotides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labeled reagents may be used in a variety of well-known assays, such as radioimmunoassays, enzyme immunoassays, e.g., ELISA, fluorescent immunoassays, and the like.

The antibodies are tagged with such labels by known methods. For instance, coupling agents such as aldehydes, carbodiimides, dimaleimide, imidates, succinimides, bid-diazotized benzadine and the like are used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, Methods in Enzymology 32b, 103 (1974), Syvanen et al., J. Biol. Chem. 284, 3762 (1973) and Bolton and Hunter, Biochem J. 133, 529 (1973).

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Amon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurds, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Diagnostic methods generally involve contacting a biological sample obtained from a patient, such as, e.g., blood, serum, saliva, urine, sputum, a cell swab sample, or a tissue biopsy, with an HRV antibody and determining whether the antibody preferentially binds to the sample as compared to a control sample or predetermined cut-off value, thereby indicating the presence of infected cells. In particular embodiments, at least two-fold, three-fold, or five-fold more HRV antibody binds to an infected cell as compared to an appropriate control normal cell or tissue sample. A pre-determined cut-off value is determined, e.g., by averaging the amount of HRV antibody that binds to several different appropriate control samples under the same conditions used to perform the diagnostic assay of the biological sample being tested.

Bound antibody is detected using procedures described herein and known in the art. In certain embodiments, diagnostic methods of the invention are practiced using HRV antibodies that are conjugated to a detectable label, e.g., a fluorophore, to facilitate detection of bound antibody. However, they are also practiced using methods of secondary detection of the HRV antibody. These include, for example, RIA, ELISA, precipitation, agglutination, complement fixation and immuno-fluorescence.

HRV antibodies of the present invention are capable of differentiating between patients with and patients without an HRV infection, and determining whether or not a patient has an infection, using the representative assays provided herein. According to one method, a biological sample is obtained from a patient suspected of having or known to have HRV infection. In preferred embodiments, the biological sample includes cells from the patient. The sample is contacted with an HRV antibody, e.g., for a time and under conditions sufficient to allow the HRV antibody to bind to infected cells present in the sample. For instance, the sample is contacted with an HRV antibody for 10 seconds, 30 seconds, 1 minute, 5 minutes, 10 minutes, 30 minutes, 1 hour, 6 hours, 12 hours, 24 hours, 3 days or any point in between. The amount of bound HRV antibody is determined and compared to a control value, which may be, e.g., a pre-determined value or a value determined from normal tissue sample. An increased amount of antibody bound to the patient sample as compared to the control sample is indicative of the presence of infected cells in the patient sample.

In a related method, a biological sample obtained from a patient is contacted with an HRV antibody for a time and under conditions sufficient to allow the antibody to bind to infected cells. Bound antibody is then detected, and the presence of bound antibody indicates that the sample contains infected cells. This embodiment is particularly useful when the HRV antibody does not bind normal cells at a detectable level.

Different HRV antibodies possess different binding and specificity characteristics. Depending upon these characteristics, particular HRV antibodies are used to detect the presence of one or more strains of HRV. For example, certain antibodies bind specifically to only one or several strains of HRV, whereas others bind to all or a majority of different strains of HRV. Antibodies specific for only one strain of HRV are used to identify the strain of an infection.

In certain embodiments, antibodies that bind to an infected cell preferably generate a signal indicating the presence of an infection in at least about 20% of patients with the infection being detected, more preferably at least about 30% of patients. Alternatively, or in addition, the antibody generates a negative signal indicating the absence of the infection in at least about 90% of individuals without the infection being detected. Each antibody satisfies the above criteria; however, antibodies of the present invention are used in combination to improve sensitivity.

The present invention also includes kits useful in performing diagnostic and prognostic assays using the antibodies of the present invention. Kits of the invention include a suitable container comprising an HRV antibody of the invention in either labeled or unlabeled form. In addition, when the antibody is supplied in a labeled form suitable for an indirect binding assay, the kit further includes reagents for performing the appropriate indirect assay. For example, the kit includes one or more suitable containers including enzyme substrates or derivatizing agents, depending on the nature of the label. Control samples and/or instructions are also included.

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using human monoclonal antibodies provides an immediate treatment strategy for emergency prophylaxis and treatment of HRV.

HRV antibodies and fragments thereof, and therapeutic compositions, of the invention specifically bind or preferentially bind to infected cells, as compared to normal control uninfected cells and tissue. Thus, these HRV antibodies are used to selectively target infected cells or tissues in a patient, biological sample, or cell population. In light of the infection-specific binding properties of these antibodies, the present invention provides methods of regulating (e.g., inhibiting) the growth of infected cells, methods of killing infected cells, and methods of inducing apoptosis of infected cells. These methods include contacting an infected cell with an HRV antibody of the invention. These methods are practiced in vitro, ex vivo, and in vivo.

In various embodiments, antibodies of the invention are intrinsically therapeutically active. Alternatively, or in addition, antibodies of the invention are conjugated to a cytotoxic agent or growth inhibitory agent, e.g., a radioisotope or toxin that is used in treating infected cells bound or contacted by the antibody.

Subjects at risk for HRV-related diseases or disorders include patients who have come into contact with an infected person or who have been exposed to HRV in some other way. Administration of a prophylactic agent can occur prior to the manifestation of symptoms characteristic of HRV-related disease or disorder, such that a disease or disorder is prevented or, alternatively, delayed in its progression.

Methods for preventing an increase in HRV virus titer, virus replication, virus proliferation or an amount of an HRV viral protein in a subject are further provided. In one embodiment, a method includes administering to the subject an amount of an HRV antibody effective to prevent an increase in HRV titer, virus replication or an amount of an HRV protein of one or more HRV strains or isolates in the subject.

For in vivo treatment of human and non-human patients, the patient is usually administered or provided a pharmaceutical formulation including an HRV antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the target cell site, or intravenously. Intravenous or subcutaneous administration of the antibody is preferred in certain embodiments. Therapeutic compositions of the invention are administered to a patient or subject systemically, parenterally, or locally.

For parenteral administration, the antibodies are formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. The antibodies are typically formulated in such vehicles at concentrations of about 1 mg/ml to 10 mg/ml.

The dose and dosage regimen depends upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In particular embodiments, the amount of antibody administered is in the range of about 0.1 mg/kg to about 50 mg/kg of patient body weight. Depending on the type and severity of the infection, about 0.1 mg/kg to about 50 mg/kg body weight (e.g., about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art.

In one particular embodiment, an immunoconjugate including the antibody conjugated with a cytotoxic agent is administered to the patient. Preferably, the immunoconjugate is internalized by the cell, resulting in increased therapeutic efficacy of the immunoconjugate in killing the cell to which it binds. In one embodiment, the cytotoxic agent targets or interferes with the nucleic acid in the infected cell. Examples of such cytotoxic agents are described above and include, but are not limited to, maytansinoids, calicheamicins, ribonucleases and DNA endonucleases.

Other therapeutic regimens are combined with the administration of the HRV antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In certain embodiments, it is desirable to combine administration of an antibody of the invention with another antibody directed against another antigen associated with the infectious agent.

Aside from administration of the antibody protein to the patient, the invention provides methods of administration of the antibody by gene therapy. Such administration of nucleic acid encoding the antibody is encompassed by the expression "administering a therapeutically effective amount of an antibody". See, for example, PCT Patent Application Publication WO96/07321 concerning the use of gene therapy to generate intracellular antibodies.

In another embodiment, anti-HRV antibodies of the invention are used to determine the structure of bound antigen, e.g., conformational epitopes, the structure of which is then used to develop a vaccine having or mimicking this structure, e.g., through chemical modeling and SAR methods. Such a vaccine could then be used to prevent HRV infection.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Isolation and Characterization of Cross-Serotype Neutralizing Monoclonal Antibodies Against Rhinovirus IgG expressing memory B cells were isolated from a healthy individual by negative depletion of other peripheral blood mononuclear cells (PBMC) on magnetic beads. Memory B cells were activated at near clonal density in 384-well microplates in the presence of cytokines and feeder cells that promote polyclonal B cell activation. Supernatants of B cell culture wells containing secreted antibodies were screened for neutralization against 2 serotypes of rhinovirus (HRV) in cytopathic effect (CPE) assay. Variable regions of the IgG heavy and light chains from the B cell clones that neutralized both serotypes were rescued by RT-PCR and the sequences were determined by 454 pyrosequencing (also known as deep sequencing). The sequences from an individual B cell clone were then compared with those from other B cell clones to identify clonally related antibodies also known "sister" mAbs. These clonally related sister clones are likely derived from the same precursor B cell. The variable regions were synthesized as DNA and cloned in expression vectors with the appropriate IgG1, Igκ or Igλ constant domain. Monoclonal antibodies were reconstituted by transient transfection in HEK293 cells followed by purification from serum-free culture supernatants.

Figure 4B:
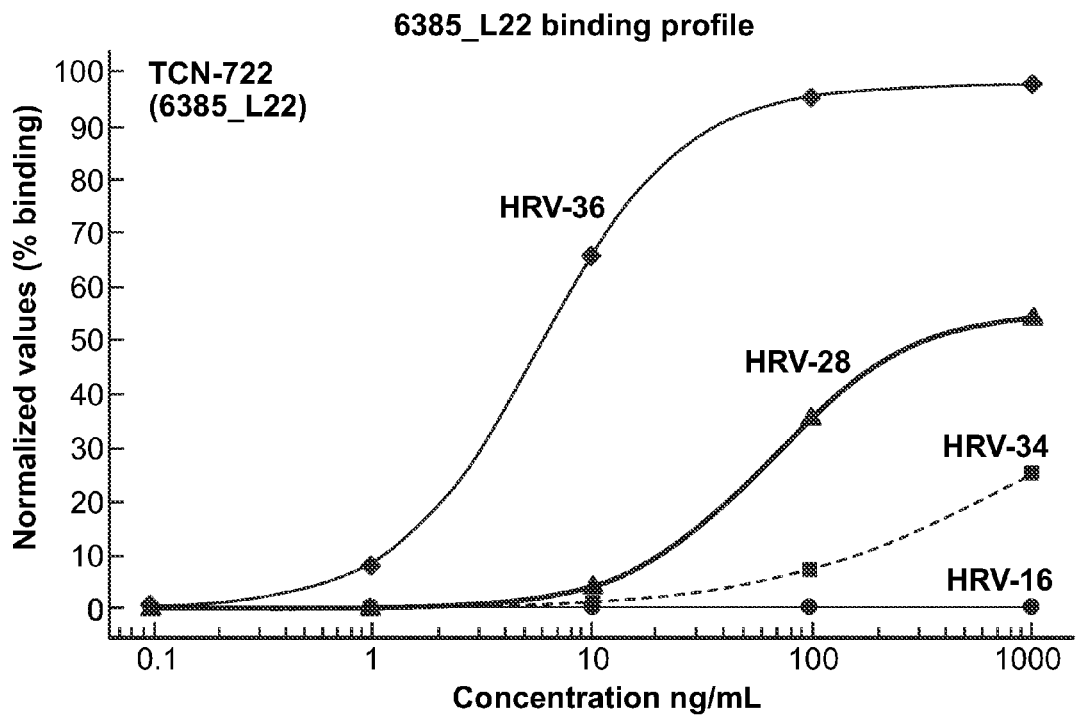

Purified monoclonal antibodies were analyzed in a titration series of concentrations for neutralization activity against a panel of 38 HRV serotypes that include 22 major group viruses and 4 minor group viruses in clade A, 2 viruses in clade D, and 10 viruses in clade B in microneutralization or CPE assay. The IC50 values determined for three monoclonal antibodies, TCN-717 (or H17), TCN-722 (or L22) and TCN-716 (or F16) against each virus that was neutralized are shown in FIG. 1. FIG. 2 shows the % serotypes in the panel of 38 viruses and in the subset of 22 viruses from the clade A major group that were neutralized by each of the three monoclonal antibodies or by two antibodies in combination. The percent (%) serotypes neutralized represents the relative breadth of neutralization by these antibodies. From this panel of 38 HRV serotypes, TCN-717, TCN-722 or TCN-716 neutralized only viruses belonging to the clade A major group and clade D. FIG. 3 shows the neutralization profile of each antibody for 26 clade A serotypes and two clade D serotypes. Although TCN-717 and TCN-722 are clonally related by sequence, their neutralization profiles reveal differences in the fine specificities. TCN-717 and TCN-722 were further analyzed for direct binding to intact inactivated virus immobilized on plastic by ELISA. The direct binding of TCN-717 to HRV-28 and HRV-36 and binding of TCN-722 to HRV-28, HRV-34 and HRV-36 are shown in FIG. 4.

Example 2

Isolation and Characterization of Cross-Serotype Non-Neutralizing Monoclonal Antibodies Against Rhinovirus Memory B cells were isolated from a healthy individual different from the one described in Example 1 using similar method. B cell culture supernatants were screened for cross-serotype binding reactivity by capturing human IgG on microarray glass slides and incubating with inactivated virus of ten different serotypes separately. Variable regions of the IgG heavy and light chains from a B cell clone, TCN-711 (or E11), that bound to nine serotypes were rescued by RT-PCR and the sequences were determined by deep sequencing. The variable regions were synthesized as DNA and cloned in an expression vector with IgG1 constant domain and another one with Igλ constant domain. Monoclonal antibodies were reconstituted by transient transfection in HEK293 cells followed by purification from serum-free culture supernatants.

Purified TCN-711 was analyzed in a titration series of concentrations for binding activity against a panel of 38 HRV serotypes that include 22 major group viruses and 4 minor group viruses in clade A, 2 viruses in clade D, and 10 viruses in clade B. The panel of serotypes tested is the same as used in Example 1. To detect binding activity of TCN-711, HeLa cells were infected with individual HRV serotype overnight. After washing to remove free virus, infected cells were fixed, permeabilized one day later and incubated with TCN-711 at 2 µg/ml for one hour. Bound TCN-711 was detected by incubation with Alexafluor-647 conjugated anti-human Fc and visualized by imaging on an InCell Analyzer. Table 1 shows the specific binding of TCN-711 to 35 HRV serotypes that include viruses from clade A major and minor groups, clade B and clade D, which represents 92% of the serotypes in the panel of 38 viruses. The binding of TCN-711 to four serotypes in a titration series of concentrations was shown in FIG. 5. Half-maximal binding of TCN-711 was detected from 1 to 10 ng/ml.

TABLE 1

Binding profile of TCN-711 to a panel of HRV serotypes.

| Serotype | Clade | Binding of TCN-711 |
|---|---|---|
| HRV-12 | A/major gp | + |
| HRV-13 | | + |
| HRV-16 | | + |
| HRV-21 | | + |
| HRV-23 | | + |
| HRV-24 | | + |
| HRV-28 | | + |
| HRV-34 | | + |
| HRV-36 | | + |
| HRV-38 | | + |
| HRV-40 | | + |
| HRV-51 | | + |
| HRV-54 | | + |
| HRV-61 | | + |
| HRV-63 | | + |
| HRV-64 | | − |
| HRV-67 | | + |
| HRV-74 | | + |
| HRV-75 | | + |
| HRV-76 | | + |
| HRV-88 | | + |
| HRV-89 | | + |
| HRV-29 | A/minor gp | + |
| HRV-31 | | + |
| HRV-49 | | + |
| HRV-62 | | + |
| HRV-14 | B | + |
| HRV-26 | | − |
| HRV-37 | | + |
| HRV-48 | | − |
| HRV-52 | | + |
| HRV-70 | | + |
| HRV-83 | | + |
| HRV-84 | | + |
| HRV-86 | | + |
| HRV-93 | | + |
| HRV-08 | D | + |
| HRV-45 | | + |

Other Embodiments

Although specific embodiments of the invention have been described herein for purposes of illustration, various modifications may be made without deviating from the spirit and scope of the invention. Accordingly, the invention is not limited except as by the appended claims. While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated fully human monoclonal antibody, wherein said monoclonal antibody has the following characteristics
   a) binds to an epitope in the rhinovirus capsid protein selected from the group consisting of VP1, VP2, VP3, and VP4;
   b) binds to rhinovirus inside infected cells; and
   c) binds to rhinovirus
wherein the antibody comprises,
   (a) a VH CDR1 region comprising the amino acid sequence of DFYWT (SEQ ID NO: 5); a VH CDR2 region comprising the amino acid sequence of EIDRDGATYYNPSLKS (SEQ ID NO: 6); a VH CDR3 region comprising the amino acid sequence of RPMLRGVWGNFRSNWFDP (SEQ ID NO: 7); a VL CDR1 region comprising the amino acid sequence of SGSSSNIGYSYVS (SEQ ID NO: 14); a VL CDR2 region comprising the amino acid sequence of ENNKRPS (SEQ ID NO: 15); and a VL CDR3 region comprising the amino acid sequence of GTWDTRLFGGV (SEQ ID NO: 16);
   (b) a VH CDR1 region comprising the amino acid sequence of DFAMH (SEQ ID NO: 21); a VH CDR2 region comprising the amino acid sequence of SISRDGSTKYSGDSVKG (SEQ ID NO: 22); a VH CDR3 region comprising the amino acid sequence of DSPYYLDIVGYRYFHHYGMDV (SEQ ID NO: 23); a VL CDR1 region comprising the amino acid sequence of RASQILHSYNLA (SEQ ID NO: 30); a VL CDR2 region comprising the amino acid sequence of GAYNRAS (SEQ ID NO: 31); and a VL CDR3 region comprising the amino acid sequence of QQYGDSPSPGLT (SEQ ID NO: 32);
   (c) a VH CDR1 region comprising the amino acid sequence of QNDYHWA (SEQ ID NO: 37); a VH CDR2 region comprising the amino acid sequence of SVHYRQKSYYSPSLKS (SEQ ID NO: 38); a VH CDR3 region comprising the amino acid sequence of HNREDYYDSNAYFDE (SEQ ID NO: 39); a VL CDR1 region comprising the amino acid sequence of SGDDLENTLVC (SEQ ID NO: 46); a VL CDR2 region comprising the amino acid sequence of QDSKRPS (SEQ ID NO: 47); and a VL CDR3 region comprising the amino acid sequence of QTWHRSTAQYV (SEQ ID NO: 48); or
   (d) a VH CDR1 region comprising the amino acid sequence of SNDQYWA (SEQ ID NO: 53); a VH CDR2 region comprising the amino acid sequence of SVHYRRRNYYSPSLES (SEQ ID NO: 54); a VH CDR3 region comprising the amino acid sequence of HNWEDYYESNAYFDY (SEQ ID NO: 55); a VL CDR1 region comprising the amino acid sequence of SGDQLENTFVC (SEQ ID NO: 62); a VL CDR2 region comprising the amino acid sequence of QGSKRPS (SEQ ID NO: 63); and a VL CDR3 region comprising the amino acid sequence of QAWDRSTAHYV (SEQ ID NO: 64).

2. An isolated fully human monoclonal antibody, wherein said monoclonal antibody has the following characteristics
   a) binds to an epitope in the rhinovirus capsid protein selected from the group consisting of VP1, VP2, VP3, and VP4;
   b) binds to rhinovirus inside infected cells; and
   c) binds to rhinovirus having serotypes from one or more clades selected from the group consisting of Glade A (major group), Glade A (minor group), Glade B, and Glade D
wherein the antibody comprises,
   (a) a VH CDR1 region comprising the amino acid sequence of DFAMH (SEQ ID NO: 21); a VH CDR2 region comprising the amino acid sequence of SISRDGSTKYSGDSVKG (SEQ ID NO: 22); a VH CDR3 region comprising the amino acid sequence of DSPYYLDIVGYRYFHHYGMDV (SEQ ID NO: 23); a VL CDR1 region comprising the amino acid sequence of RASQILHSYNLA (SEQ ID NO: 30); a VL CDR2 region comprising the amino acid sequence of GAYNRAS (SEQ ID NO: 31); and a VL CDR3 region comprising the amino acid sequence of QQYGDSPSPGLT (SEQ ID NO: 32); or
   (b) a VH CDR1 region comprising the amino acid sequence of QNDYHWA (SEQ ID NO: 37); a VH CDR2 region comprising the amino acid sequence of SVHYRQKSYYSPSLKS (SEQ ID NO: 38); a VH CDR3 region comprising the amino acid sequence of HNREDYYDSNAYFDE (SEQ ID NO: 39); a VL CDR1 region comprising the amino acid sequence of SGDDLENTLVC (SEQ ID NO: 46); a VL CDR2 region comprising the amino acid sequence of QDSKRPS (SEQ ID NO: 47); and a VL CDR3 region comprising the amino acid sequence of QTWHRSTAQYV (SEQ ID NO: 48); or
   (c) a VH CDR1 region comprising the amino acid sequence of SNDQYWA (SEQ ID NO: 53); a VH CDR2 region comprising the amino acid sequence of SVHYRRRNYYSPSLES (SEQ ID NO: 54); a VH CDR3 region comprising the amino acid sequence of HNWEDYYESNAYFDY (SEQ ID NO: 55); a VL CDR1 region comprising the amino acid sequence of SGDQLENTFVC (SEQ ID NO: 62); a VL CDR2 region comprising the amino acid sequence of QGSKRPS (SEQ ID NO: 63); and
   a VL CDR3 region comprising the amino acid sequence of QAWDRSTAHYV (SEQ ID NO: 64).

3. An isolated anti-HRV antibody, wherein said antibody comprises,
- a VH CDR1 region comprising the amino acid sequence of DFYWT (SEQ ID NO: 5);
- a VH CDR2 region comprising the amino acid sequence of EIDRDGATYYNPSLKS (SEQ ID NO: 6);
- a VH CDR3 region comprising the amino acid sequence of RPMLRGVWGNFRSNWFDP (SEQ ID NO: 7);
- a VL CDR1 region comprising the amino acid sequence of SGSSSNIGYSYVS (SEQ ID NO: 14);
- a VL CDR2 region comprising the amino acid sequence of ENNKRPS (SEQ ID NO: 15); and
- a VL CDR3 region comprising the amino acid sequence of GTWDTRLFGGV (SEQ ID NO: 16).

4. An isolated anti-HRV antibody, wherein said antibody comprises,
- a VH CDR1 region comprising the amino acid sequence of DFAMH (SEQ ID NO: 21);
- a VH CDR2 region comprising the amino acid sequence of SISRDGSTKYSGDSVKG (SEQ ID NO: 22);
- a VH CDR3 region comprising the amino acid sequence of DSPYYLDIVGYRYFHHYGMDV (SEQ ID NO: 23);
- a VL CDR1 region comprising the amino acid sequence of RASQILHSYNLA (SEQ ID NO: 30);
- a VL CDR2 region comprising the amino acid sequence of GAYNRAS (SEQ ID NO: 31); and
- a VL CDR3 region comprising the amino acid sequence of QQYGDSPSPGLT (SEQ ID NO: 32).

5. An isolated anti-HRV antibody, wherein said antibody comprises,
- a VH CDR1 region comprising the amino acid sequence of QNDYHWA (SEQ ID NO: 37);
- a VH CDR2 region comprising the amino acid sequence of SVHYRQKSYYSPSLKS (SEQ ID NO: 38);
- a VH CDR3 region comprising the amino acid sequence of HNREDYYDSNAYFDE (SEQ ID NO: 39);
- a VL CDR1 region comprising the amino acid sequence of SGDDLENTLVC (SEQ ID NO: 46);
- a VL CDR2 region comprising the amino acid sequence of QDSKRPS (SEQ ID NO: 47); and
- a VL CDR3 region comprising the amino acid sequence of QTWHRSTAQYV (SEQ ID NO: 48).

6. An isolated anti-HRV antibody, wherein said antibody comprises,
- a VH CDR1 region comprising the amino acid sequence of SNDQYWA (SEQ ID NO: 53);
- a VH CDR2 region comprising the amino acid sequence of SVHYRRRNYYSPSLES (SEQ ID NO: 54);
- a VH CDR3 region comprising the amino acid sequence of HNWEDYYESNAYFDY (SEQ ID NO: 55);
- a VL CDR1 region comprising the amino acid sequence of SGDQLENTFVC (SEQ ID NO: 62);
- a VL CDR2 region comprising the amino acid sequence of QGSKRPS (SEQ ID NO: 63); and
- a VL CDR3 region comprising the amino acid sequence of QAWDRSTAHYV (SEQ ID NO: 64).

7. An antibody that binds the same epitope as an antibody comprising,
- (a) a VH CDR1 region comprising the amino acid sequence of DFYWT (SEQ ID NO: 5); a VH CDR2 region comprising the amino acid sequence of EIDRDGATYYNPSLKS (SEQ ID NO: 6); a VH CDR3 region comprising the amino acid sequence of RPMLRGVWGNFRSNWFDP (SEQ ID NO: 7); a VL CDR1 region comprising the amino acid sequence of SGSSSNIGYSYVS (SEQ ID NO: 14); a VL CDR2 region comprising the amino acid sequence of ENNKRPS (SEQ ID NO: 15); and a VL CDR3 region comprising the amino acid sequence of GTWDTRLFGGV (SEQ ID NO: 16);
- (b) a VH CDR1 region comprising the amino acid sequence of DFAMH (SEQ ID NO: 21); a VH CDR2 region comprising the amino acid sequence of SISRDGSTKYSGDSVKG (SEQ ID NO: 22); a VH CDR3 region comprising the amino acid sequence of DSPYYLDIVGYRYFHHYGMDV (SEQ ID NO: 23); a VL CDR1 region comprising the amino acid sequence of RASQILHSYNLA (SEQ ID NO: 30); a VL CDR2 region comprising the amino acid sequence of GAYNRAS (SEQ ID NO: 31); and a VL CDR3 region comprising the amino acid sequence of QQYGDSPSPGLT (SEQ ID NO: 32);
- (c) a VH CDR1 region comprising the amino acid sequence of QNDYHWA (SEQ ID NO: 37); a VH CDR2 region comprising the amino acid sequence of SVHYRQKSYYSPSLKS (SEQ ID NO: 38); a VH CDR3 region comprising the amino acid sequence of HNREDYYDSNAYFDE (SEQ ID NO: 39); a VL CDR1 region comprising the amino acid sequence of SGDDLENTLVC (SEQ ID NO: 46); a VL CDR2 region comprising the amino acid sequence of QDSKRPS (SEQ ID NO: 47); and a VL CDR3 region comprising the amino acid sequence of QTWHRSTAQYV (SEQ ID NO: 48); or
- (d) a VH CDR1 region comprising the amino acid sequence of SNDQYWA (SEQ ID NO: 53); a VH CDR2 region comprising the amino acid sequence of SVHYRRRNYYSPSLES (SEQ ID NO: 54); a VH CDR3 region comprising the amino acid sequence of HNWEDYYESNAYFDY (SEQ ID NO: 55); a VL CDR1 region comprising the amino acid sequence of SGDQLENTFVC (SEQ ID NO: 62); a VL CDR2 region comprising the amino acid sequence of QGSKRPS (SEQ ID NO: 63); and a VL CDR3 region comprising the amino acid sequence of QAWDRSTAHYV (SEQ ID NO: 64).

8. An isolated monoclonal anti-HRV antibody comprising,
- a) a heavy chain sequence comprising the amino acid sequence of SEQ ID NO: 4 and a light chain sequence comprising amino acid sequence SEQ ID NO: 13, or
- b) a heavy chain sequence comprising the amino acid sequence of SEQ ID NO: 20 and a light chain sequence comprising amino acid sequence SEQ ID NO: 29, or
- c) a heavy chain sequence comprising the amino acid sequence of SEQ ID NO: 36 and a light chain sequence comprising amino acid sequence SEQ ID NO: 45, or
- d) a heavy chain sequence comprising the amino acid sequence of SEQ ID NO: 52 and a light chain sequence comprising amino acid sequence SEQ ID NO: 61.

9. A composition comprising an isolated anti-HRV antibody of any one of claims 1-8.

10. A pharmaceutical composition comprising at least one antibody as recited in any one of claims 1-8, and a pharmaceutically acceptable carrier.

11. The composition of claim 9, further comprising a second therapeutic agent.

12. The composition of claim 11, wherein the second therapeutic agent is a second antibody, an antiviral drug, an antibiotic, a bronchodilator, a leukotriene blocker, a steroid, an antiinflammatory drug, or an oxygen therapy.

13. The composition of claim 12, wherein the second antibody is specific for human rhinovirus, influenza, parainfluenza, coronavirus, adenovirus, respiratory syncytical virus, picornavirus, metapneumovirus, or anti-IgE antibody.

14. The composition of claim 12, wherein the anti-viral drug is an entry inhibitor, a fusion inhibitor, an integrase inhibitor, a nucleoside analog, a protease inhibitor, or a reverse transcriptase inhibitor.

15. The composition of claim 12, wherein the anti-viral drug is Abacavir, Acicolvir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Immunovir, Idoxuridine, Imiquimod, Indinavir, Inosine, Interferon (Type I, II, or III), Lamivudine, Lopinavir, Loviride, Maraviroc, Moroxydine, Methisazone, Nelfinavir, Nevirapine, Nexavir, Oseltamivir, Peginterferon alpha-2a, Pencicolvir, Peramivir, Pleconaril, Podophyllotoxin, Raltegravir, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, or Zidovudine.

16. The composition of claim 12, wherein the antibiotic is an Aminoglycoside, a Carbapenem, a Cephalosporin, a Lincosamide, a Macrolide, a Penicillin, or a Quinolone.

17. The composition of claim 12, wherein the antibiotic is Amikacin, Gentamicin, Kanamycin, Neomycin, Netilmycin, Tobramycin, Paromycin, Geldanamycin, Ertapenem, Dorpenem, Imipenem/Cilastatin, Meropenem, Cefadroxil, Cefazolin, Cefalotin, Cefalothin, Cefalexin, Cefaclor, Ceamandole, Cefoxitin, Cefprozil, Cefurozime, Cefixime, Cefdinir, Defditoren, Cefoperazone, Cefotaxime, Cefazidime, Ceftibuten, Ceftizoxime, Ceftriaxone, Cefepime, Ceftobiprole, Teicoplanin, Vancomycin, Telavancin, Clindamycin, Lincomycin, Daptomycin, Azithromyzin, Clarithromycin, Dirithromycin, Erythromycin, Roxithromycin, Troleandomycin, Spectinomycin, Aztreonam, Furazolidone, Nitofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, Trimethoprim-Sulfamethoxazole (Cotrumoxazole), Demeclocycline, Docycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifampin, Rifabutin, Rifapentin, Stretomycin, Arsphenamine, Choramphenicol, Fosfomycin, Fusidic acid, Linezolid, Metonidazole, Mupirocin, Platensimycin, Quinupristin/Dalfopristin, Rifaximin, Thamphenicol, Tigecycline, Tinidazole.

18. The composition of claim 12, wherein the bronchodilator is a short- or long-acting agent.

19. The composition of claim 12, wherein the short-acting bronchodilator is a β2-agonist or an anticholinergic.

20. The composition of claim 18, wherein the long-acting bronchodilator is a β2-agonist or a theophylline.

21. The composition of claim 12, wherein the steroid is a corticosteroid.

22. The composition of claim 21, wherein corticosteroid is hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate.

23. The composition of claim 12, wherein the anti-inflammatory drug is an antihistamine or a histamine receptor blocker.

24. The composition of claim 12, wherein the oxygen therapy is supplemental oxygen gas, and wherein the arterial blood oxygen saturation of the subject following treatment is greater than or equal to 85%.

25. A vaccine comprising an isolated anti-HRV antibody as recited in any one of claims 1-8.

26. A kit comprising an isolated anti-HRV antibody as recited in any one of claims 1-8.

27. The antibody of one of claims 1-8, wherein the antibody binds to an epitope comprising a portion of two or more rhinovirus capsid proteins selected from the group consisting of VP1, VP2, VP3, and VP4.

28. The antibody of any one of claims 1, 3, 4, 5, 6, 7 and 8, wherein the antibody binds to rhinovirus serotypes from one or more clades selected from the group consisting of Glade A (major group), Glade A (minor group), Glade B, and Glade D.

29. The antibody of any one of claims 1-8, wherein the antibody cross-neutralizes multiple rhinovirus serotypes from the group consisting of Glade A (major group), Glade A (minor group), Glade B, and Glade D.

30. The antibody of any one of claims 1-8, wherein the antibody neutralizes at least 40% of HRV serotypes selected from the group consisting of HRV-12, HRV-13, HRV-16, HRV-21, HRV-23, HRV-24, HRV-28, HRV-34, HRV-36, HRV-38, HRV-40, HRV-51, HRV-54, HRV-61, HRV-63, HRV-64, HRV-67, HRV-74, HRV-75, HRV-76, HRV-88, HRV-89, HRV-29, HRV-31, HRV-49, HRV-62, HRV-14, HRV-26, HRV-37, HRV-48, HRV-52, HRV-70, HRV-83, HRV-84, HRV-86, HRV-93, HRV-08, and HRV-45.

31. The antibody of any one of claims 1-8, wherein the antibody binds to at least 90% of the HRV serotypes.

32. The antibody of claim 28, wherein the antibody neutralizes the HRV serotypes with a median IC50 value of equal to or less than 100 ng/ml.

33. The antibody of any one of claims 1-8, wherein the antibody is isolated from a B-cell from a human donor.

34. The antibody of any one of claims 1-8, wherein said epitope is non-linear.

35. The composition of claim 10, further comprising a second therapeutic agent.

36. The composition of claim 35, wherein the second therapeutic agent is a second antibody, an antiviral drug, an antibiotic, a bronchodilator, a leukotriene blocker, a steroid, an antiflammatory drug, or an oxygen therapy.

37. The composition of claim 36, wherein the second antibody is specific for human rhinovirus, influenza, parainfluenza, coronavirus, adenovirus, respiratory syncytical virus, picornavirus, metapneumovirus, or anti-IgE antibody.

38. The composition of claim 36, wherein the anti-viral drug is an entry inhibitor, a fusion inhibitor, an integrase inhibitor, a nucleoside analog, a protease inhibitor, or a reverse transcriptase inhibitor.

39. The composition of claim 36, wherein the anti-viral drug is Abacavir, Acicolvir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Immunovir, Idoxuridine, Imiquimod, Indinavir, Inosine, Interferon (Type I, II, or III), Lamivudine, Lopinavir, Loviride, Maraviroc, Moroxydine, Methisazone, Nelfinavir, Nevirapine, Nexavir, Oseltamivir, Peginterferon alpha-2a, Pencicolvir, Peramivir, Pleconaril, Podophyllotoxin, Raltegravir, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, or Zidovudine.

40. The composition of claim 36, wherein the antibiotic is an Aminoglycoside, a Carbapenem, a Cephalosporin, a Lincosamide, a Macrolide, a Penicillin, or a Quinolone.

41. The composition of claim 36, wherein the antibiotic is Amikacin, Gentamicin, Kanamycin, Neomycin, Netilmycin, Tobramycin, Paromycin, Geldanamycin, Ertapenem, Dorpenem, Imipenem/Cilastatin, Meropenem, Cefadroxil, Cefazolin, Cefalotin, Cefalothin, Cefalexin, Cefaclor, Ceamandole, Cefoxitin, Cefprozil, Cefurozime, Cefixime, Cefdinir, Defditoren, Cefoperazone, Cefotaxime, Cefazidime, Ceftibuten, Ceftizoxime, Ceftriaxone, Cefepime, Ceftobiprole, Teicoplanin, Vancomycin, Telavancin, Clindamycin, Lincomycin, Daptomycin, Azithromyzin, Clarithromycin, Dirithromycin, Erythromycin, Roxithromycin, Troleandomycin, Spectinomycin, Aztreonam, Furazolidone, Nitofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, Trimethoprim-Sulfamethoxazole (Cotrumoxazole), Demeclocycline, Docycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifampin, Rifabutin, Rifapentin, Stretomycin, Arsphenamine, Choramphenicol, Fosfomycin, Fusidic acid, Linezolid, Metonidazole, Mupirocin, Platensimycin, Quinupristin/Dalfopristin, Rifaximin, Thamphenicol, Tigecycline, Tinidazole.

42. The composition of claim 36, wherein the bronchodilator is a short- or long-acting agent.

43. The composition of claim 42, wherein the short-acting bronchodilator is a β2-agonist or an anticholinergic.

44. The composition of claim 42, wherein the long-acting bronchodilator is a β2-agonist or a theophylline.

45. The composition of claim 36, wherein the steroid is a corticosteroid.

46. The composition of claim 45, wherein corticosteroid is hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate.

47. The composition of claim 36, wherein the anti-inflammatory drug is an antihistamine or a histamine receptor blocker.

48. The composition of claim 36, wherein the oxygen therapy is supplemental oxygen gas, and wherein the arterial blood oxygen saturation of the subject following treatment is greater than or equal to 85%.

* * * * *

SEQUENCE LISTING

```
<160> NUMBER OF SEQ ID NOS: 64

<210> SEQ ID NO 1
<211> LENGTH: 1428
<212> TYPE: DNA
<213> ORGANISM: Homo sapiens

<400> SEQUENCE: 1
atgaaacacc tgtggttctt cctcctcctg gcggcagctc ccagatgggt cctgtcccag      60
gtgcagctac accagtgggg cacaggagtg ttgaagcctt cggggaccct gtccctcacc     120
tgcggtgtct atggtgggtc cctcactgat ttctactgga cctggatccg tcagtcccca     180 gcgagggcc tggagtggct tggagaaatc gatcgtgatg gggccacgta ctataatccg      240
tccctaaaga gtcgaatcac catttcgata gacacgtcca agaaacaatt ctccttgaat     300
ctgcggtctg tgaccgccgc ggacagggct gtctactact gtgcgaggcg ccctatgtta     360
cgaggcgttt gggggaattt tcgttccaac tggttcgacc cctggggcca gggaacccag     420
gtcaccgtct cgagcgcctc caccaagggc ccatcggtct tccccctggc accctcctcc     480
aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtggac     720
aagagagttg agcccaaatc ttgtgacaaa actcacacat gcccaccgtg cccagcacct     780
gaactcctgg ggggaccgtc agtcttcctc ttccccccaa aacccaagga caccctcatg     840
atctcccgga cccctgaggt cacatgcgtg gtggtggacg tgagccacga agaccctgag     900
gtcaagttca actggtacgt ggacggcgtg gaggtgcata atgccaagac aaagccgcgg     960
gaggagcagt acaacagcac gtaccgtgtg gtcagcgtcc tcaccgtcct gcaccaggac    1020
tggctgaatg gcaaggagta caagtgcaag gtctccaaca aagccctccc agcccccatc    1080
gagaaaacca tctccaaagc caaagggcag ccccgagaac cacaggtgta ccctgcc     1140 ccatcccggg aggagatgac caagaaccag gtcagcctga cctgcctggt caaaggcttc    1200
tatcccagcg acatcgccgt ggagtgggag agcaatgggc agccggagaa caactacaag    1260
accacgcctc ccgtgctgga ctccgacggc tccttcttcc tctatagcaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaatga            1428
```

<210> SEQ ID NO 2
<211> LENGTH: 378
<212> TYPE: DNA
<213> ORGANISM: Homo sapiens

<400> SEQUENCE: 2

```
caggtgcagc tacaccagtg gggcacagga gtgttgaagc cttcggggac cctgtccctc      60
acctgcggtg tctatggtgg gtccctcact gatttctact ggacctggat ccgtcagtcc     120
cccgcgaggg gcctggagtg gcttggagaa atcgatcgtg atggggccac gtactataat     180
ccgtccctaa agagtcgaat caccatttcg atagacacgt ccaagaaaca attctccttg     240
aatctgcggt ctgtgaccgc cgcggacagg gctgtctact actgtgcgag cgcccctatg     300
ttacgaggcg tttgggggaa ttttcgttcc aactggttcg acccctgggg ccagggaacc     360
caggtcaccg tctcgagc                                                    378
```

<210> SEQ ID NO 3
<211> LENGTH: 475
<212> TYPE: PRT
<213> ORGANISM: Homo sapiens

<400> SEQUENCE: 3

```
Met Lys His Leu Trp Phe Phe Leu Leu Leu Ala Ala Pro Arg Trp
  1               5                  10                  15
Val Leu Ser Gln Val Gln Leu His Gln Trp Gly Thr Gly Val Leu Lys
         20                  25                  30
Pro Ser Gly Thr Leu Ser Leu Thr Cys Gly Val Tyr Gly Gly Ser Leu
         35                  40                  45
Thr Asp Phe Tyr Trp Thr Trp Ile Arg Gln Ser Pro Ala Arg Gly Leu
 50                  55                  60
Glu Trp Leu Gly Glu Ile Asp Arg Asp Gly Ala Thr Tyr Tyr Asn Pro
 65                  70                  75                  80
Ser Leu Lys Ser Arg Ile Thr Ile Ser Ile Asp Thr Ser Lys Lys Gln
                 85                  90                  95
Phe Ser Leu Asn Leu Arg Ser Val Thr Ala Ala Asp Arg Ala Val Tyr
                100                 105                 110
Tyr Cys Ala Arg Arg Pro Met Leu Arg Gly Val Trp Gly Asn Phe Arg
            115                 120                 125
Ser Asn Trp Phe Asp Pro Trp Gly Gln Gly Thr Gln Val Thr Val Ser
        130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                165                 170                 175
Tyr Phe Pro Glu Pro Val Thr Val Ser Trp Asn Ser Gly Ala Leu Thr
            180                 185                 190
Ser Gly Val His Thr Phe Pro Ala Val Leu Gln Ser Ser Gly Leu Tyr
        195                 200                 205
Ser Leu Ser Ser Val Val Thr Val Pro Ser Ser Leu Gly Thr Gln
    210                 215                 220
Thr Tyr Ile Cys Asn Val Asn His Lys Pro Ser Asn Thr Lys Val Asp
225                 230                 235                 240
Lys Arg Val Glu Pro Lys Ser Cys Asp Lys Thr His Thr Cys Pro Pro
                245                 250                 255
Cys Pro Ala Pro Glu Leu Leu Gly Gly Pro Ser Val Phe Leu Phe Pro
            260                 265                 270
```

```
Pro Lys Pro Lys Asp Thr Leu Met Ile Ser Arg Thr Pro Glu Val Thr
        275                 280                 285

Cys Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 4
<211> LENGTH: 126
<212> TYPE: PRT
<213> ORGANISM: Homo sapiens

<400> SEQUENCE: 4

Gln Val Gln Leu His Gln Trp Gly Thr Gly Val Leu Lys Pro Ser Gly
1               5                   10                  15

Thr Leu Ser Leu Thr Cys Gly Val Tyr Gly Gly Ser Leu Thr Asp Phe
            20                  25                  30

Tyr Trp Thr Trp Ile Arg Gln Ser Pro Ala Arg Gly Leu Glu Trp Leu
        35                  40                  45

Gly Glu Ile Asp Arg Asp Gly Ala Thr Tyr Tyr Asn Pro Ser Leu Lys
    50                  55                  60

Ser Arg Ile Thr Ile Ser Ile Asp Thr Ser Lys Lys Gln Phe Ser Leu
65                  70                  75                  80

Asn Leu Arg Ser Val Thr Ala Ala Asp Arg Ala Val Tyr Tyr Cys Ala
                85                  90                  95

Arg Arg Pro Met Leu Arg Gly Val Trp Gly Asn Phe Arg Ser Asn Trp
            100                 105                 110

Phe Asp Pro Trp Gly Gln Gly Thr Gln Val Thr Val Ser Ser
        115                 120                 125

<210> SEQ ID NO 5
<211> LENGTH: 5
<212> TYPE: PRT
<213> ORGANISM: Homo sapiens

<400> SEQUENCE: 5
```

```
Asp Phe Tyr Trp Thr
1               5

<210> SEQ ID NO 6
<211> LENGTH: 16
<212> TYPE: PRT
<213> ORGANISM: Homo sapiens

<400> SEQUENCE: 6

Glu Ile Asp Arg Asp Gly Ala Thr Tyr Tyr Asn Pro Ser Leu Lys Ser
1               5                   10                  15

<210> SEQ ID NO 7
<211> LENGTH: 18
<212> TYPE: PRT
<213> ORGANISM: Homo sapiens

<400> SEQUENCE: 7

Arg Pro Met Leu Arg Gly Val Trp Gly Asn Phe Arg Ser Asn Trp Phe
1               5                   10                  15

Asp Pro

<210> SEQ ID NO 8
<211> LENGTH: 6
<212> TYPE: PRT
<213> ORGANISM: Homo sapiens

<400> SEQUENCE: 8

Gly Gly Ser Leu Thr Asp
1               5

<210> SEQ ID NO 9
<211> LENGTH: 9
<212> TYPE: PRT
<213> ORGANISM: Homo sapiens

<400> SEQUENCE: 9

Glu Ile Asp Arg Asp Gly Ala Thr Tyr
1               5

<210> SEQ ID NO 10
<211> LENGTH: 708
<212> TYPE: DNA
<213> ORGANISM: Homo sapiens

<400> SEQUENCE: 10
atggccagct tccctctcct cctcacccTT tcattcact gcacagggtc ctgggcccag    60
tctgtcttga cgcagccgcc ctcagtgtct gcggccccag gacagaaggt ctccatctcc   120
tgctctggaa gcagctccaa cattgggtat agttatgtat cctggtatca acaagtccca   180
ggatcagccc ccaaactcct catctatgag aataataaga ccctcaggga ttcctgac     240
cgattctcgg cctccaagtc tggcacgtca gccaccctgg acatcaccgg actccagact   300
ggggacgagg ccgattatta ttgcggaaca tgggatacca ggctgtttgg tggagtgttc   360
ggcggaggga ccaagctgac cgttctaggt cagcccaagg ctgccccctc ggtcactctg   420
ttcccgccct cctctgagga gcttcaagcc aacaaggcca cactggtgtg tctcataagt   480
gacttctacc cgggagccgt gacagtggcc tggaaggcag atagcagccc cgtcaaggcg   540
ggagtggaga ccaccacacc ctccaaacaa agcaacaaca gtacgcggc cagcagctac   600
ctgagcctga cgcctgagca gtggaagtcc cacaaaagct acagctgcca ggtcacgcat   660
```
gaagggagca ccgtggagaa gacagtggcc cctacagaat gttcatag        708

<210> SEQ ID NO 11
<211> LENGTH: 330
<212> TYPE: DNA
<213> ORGANISM: Homo sapiens

<400> SEQUENCE: 11
cagtctgtct tgacgcagcc gccctcagtg tctgcggccc caggacagaa ggtctccatc        60
tcctgctctg gaagcagctc caacattggg tatagttatg tatcctggta tcaacaagtc       120
ccaggatcag cccccaaact cctcatctat gagaataata agagaccctc agggattcct       180
gaccgattct cggcctccaa gtctggcacg tcagccaccc tggacatcac cggactccag       240
actggggacg aggccgatta ttattgcgga acatgggata ccaggctgtt tggtggagtg       300
ttcggcggag ggaccaagct gaccgttcta                                         330

<210> SEQ ID NO 12
<211> LENGTH: 235
<212> TYPE: PRT
<213> ORGANISM: Homo sapiens

<400> SEQUENCE: 12

Met Ala Ser Phe Pro Leu Leu Leu Thr Leu Leu Ile His Cys Thr Gly
1               5                   10                  15

Ser Trp Ala Gln Ser Val Leu Thr Gln Pro Pro Ser Val Ser Ala Ala
            20                  25                  30

Pro Gly Gln Lys Val Ser Ile Ser Cys Ser Gly Ser Ser Ser Asn Ile
        35                  40                  45

Gly Tyr Ser Tyr Val Ser Trp Tyr Gln Gln Val Pro Gly Ser Ala Pro
    50                  55                  60

Lys Leu Leu Ile Tyr Glu Asn Asn Lys Arg Pro Ser Gly Ile Pro Asp
65                  70                  75                  80

Arg Phe Ser Ala Ser Lys Ser Gly Thr Ser Ala Thr Leu Asp Ile Thr
                85                  90                  95

Gly Leu Gln Thr Gly Asp Glu Ala Asp Tyr Tyr Cys Gly Thr Trp Asp
            100                 105                 110

Thr Arg Leu Phe Gly Gly Val Phe Gly Gly Gly Thr Lys Leu Thr Val
        115                 120                 125

Leu Gly Gln Pro Lys Ala Ala Pro Ser Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 13
<211> LENGTH: 110

-continued

<212> TYPE: PRT
<213> ORGANISM: Homo sapiens

<400> SEQUENCE: 13

Gln Ser Val Leu Thr Gln Pro Pro Ser Val Ser Ala Ala Pro Gly Gln
1               5                   10                  15

Lys Val Ser Ile Ser Cys Ser Gly Ser Ser Asn Ile Gly Tyr Ser
            20                  25                  30

Tyr Val Ser Trp Tyr Gln Gln Val Pro Gly Ser Ala Pro Lys Leu Leu
        35                  40                  45

Ile Tyr Glu Asn Asn Lys Arg Pro Ser Gly Ile Pro Asp Arg Phe Ser
    50                  55                  60

Ala Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp Asp Thr Arg Leu
                85                  90                  95

Phe Gly Gly Val Phe Gly Gly Gly Thr Lys Leu Thr Val Leu
            100                 105                 110

<210> SEQ ID NO 14
<211> LENGTH: 13
<212> TYPE: PRT
<213> ORGANISM: Homo sapiens

<400> SEQUENCE: 14

Ser Gly Ser Ser Ser Asn Ile Gly Tyr Ser Tyr Val Ser
1               5                   10

<210> SEQ ID NO 15
<211> LENGTH: 7
<212> TYPE: PRT
<213> ORGANISM: Homo sapiens

<400> SEQUENCE: 15

Glu Asn Asn Lys Arg Pro Ser
1               5

<210> SEQ ID NO 16
<211> LENGTH: 11
<212> TYPE: PRT
<213> ORGANISM: Homo sapiens

<400> SEQUENCE: 16

Gly Thr Trp Asp Thr Arg Leu Phe Gly Gly Val
1               5                   10

<210> SEQ ID NO 17
<211> LENGTH: 1440
<212> TYPE: DNA
<213> ORGANISM: Homo sapiens

<400> SEQUENCE: 17
atggagtttg ggctgagctg ggttctcctt gttgccattt taaaaggtgc ccagtgtgag      60
gtgcaactgg tggagtctgg gggaggcttg gtcctgccgg ggggctctct gagactctcg     120
tgttcagcgt ctggattcac attgactgac tttgctatgc actgggtccg acaggctcca     180
gggaagggac tggagctcgt ctcaagtatt agtcgggatg gttctactaa atactctgga     240
gactccgtga aggcagggt cgccatctcc agggacagtg tggagaataa gttgcatctt      300
cagatgagcg gtctgaggtc tgcggacacg gctgtgtatt attgtgtgag agactccccc     360

```
tattatcttg atattgttgg ttatcgatac ttccaccact atggaatgga cgtctggggc    420 cagggggacca cggtcaccgt ctcgagcgcc tccaccaagg gcccatcggt cttccccctg    480
gcaccctcct ccaagagcac ctctgggggc acagcggccc tgggctgcct ggtcaaggac    540
tacttccccg aaccggtgac ggtgtcgtgg aactcaggcg ccctgaccag cggcgtgcac    600
accttcccgg ctgtcctaca gtcctcagga ctctactccc tcagcagcgt ggtgaccgtg    660
ccctccagca gcttgggcac ccagacctac atctgcaacg tgaatcacaa gcccagcaac    720
accaaggtgg acaagagagt tgagcccaaa tcttgtgaca aaactcacac atgcccaccg    780
tgcccagcac ctgaactcct ggggggaccg tcagtcttcc tcttccccc aaaacccaag    840 gacaccctca tgatctcccg gacccctgag gtcacatgcg tggtggtgga cgtgagccac    900
gaagaccctg aggtcaagtt caactggtac gtggacggcg tggaggtgca taatgccaag    960
acaaagccgc gggaggagca gtacaacagc acgtaccgtg tggtcagcgt cctcaccgtc    1020
ctgcaccagg actggctgaa tggcaaggag tacaagtgca aggtctccaa caaagccctc    1080 ccagcccca tcgagaaaac catctccaaa gccaagggc agccccgaga ccacaggtg    1140 tacaccctgc ccccatcccg ggaggagatg accaagaacc aggtcagcct gacctgcctg    1200
gtcaaaggct tctatcccag cgacatcgcc gtggagtggg agagcaatgg gcagccggag    1260
aacaactaca agaccacgcc tcccgtgctg gactccgacg gctccttctt cctctatagc    1320
aagctcaccg tggacaagag caggtggcag caggggaacg tcttctcatg ctccgtgatg    1380
catgaggctc tgcacaacca ctacacgcag aagagcctct ccctgtctcc gggtaaatga    1440
```

<210> SEQ ID NO 18
<211> LENGTH: 390
<212> TYPE: DNA
<213> ORGANISM: Homo sapiens

<400> SEQUENCE: 18

```
gaggtgcaac tggtggagtc tgggggaggc ttggtcctgc cggggggctc tctgagactc     60
tcgtgttcag cgtctggatt cacattgact gactttgcta tgcactgggt ccgacaggct    120
ccagggaagg gactgagct cgtctcaagt attagtcggg atggttctac taaatactct    180
ggagactccg tgaagggcag ggtcgccatc tccagggaca gtgtggagaa taagttgcat    240
cttcagatga acggtctgag gtctgcggac acggctgtgt attattgtgt gagagactcc    300
ccctattatc ttgatattgt tggttatcga tacttccacc actatggaat ggacgtctgg    360
ggccagggga ccacggtcac cgtctcgagc                                     390
```

<210> SEQ ID NO 19
<211> LENGTH: 479
<212> TYPE: PRT
<213> ORGANISM: Homo sapiens

<400> SEQUENCE: 19

```
Met Glu Phe Gly Leu Ser Trp Val Leu Leu Val Ala Ile Leu Lys Gly
1               5                   10                  15

Ala Gln Cys Glu Val Gln Leu Val Glu Ser Gly Gly Gly Leu Val Leu
            20                  25                  30

Pro Gly Gly Ser Leu Arg Leu Ser Cys Ser Ala Ser Gly Phe Thr Leu
        35                  40                  45

Thr Asp Phe Ala Met His Trp Val Arg Gln Ala Pro Gly Lys Gly Leu
    50                  55                  60

Glu Leu Val Ser Ser Ile Ser Arg Asp Gly Ser Thr Lys Tyr Ser Gly
```

```
            65                   70                  75                  80
Asp Ser Val Lys Gly Arg Val Ala Ile Ser Arg Asp Ser Val Glu Asn
                85                  90                  95
Lys Leu His Leu Gln Met Ser Gly Leu Arg Ser Ala Asp Thr Ala Val
                100                 105                 110
Tyr Tyr Cys Val Arg Asp Ser Pro Tyr Tyr Leu Asp Ile Val Gly Tyr
                115                 120                 125
Arg Tyr Phe His His Tyr Gly Met Asp Val Trp Gly Gln Gly Thr Thr
                130                 135                 140
Val Thr Val Ser Ser Ala Ser Thr Lys Gly Pro Ser Val Phe Pro Leu
145                 150                 155                 160
Ala Pro Ser Ser Lys Ser Thr Ser Gly Gly Thr Ala Ala Leu Gly Cys
                165                 170                 175
Leu Val Lys Asp Tyr Phe Pro Glu Pro Val Thr Val Ser Trp Asn Ser
                180                 185                 190
Gly Ala Leu Thr Ser Gly Val His Thr Phe Pro Ala Val Leu Gln Ser
                195                 200                 205
Ser Gly Leu Tyr Ser Leu Ser Ser Val Val Thr Val Pro Ser Ser Ser
            210                 215                 220
Leu Gly Thr Gln Thr Tyr Ile Cys Asn Val Asn His Lys Pro Ser Asn
225                 230                 235                 240
Thr Lys Val Asp Lys Arg Val Glu Pro Lys Ser Cys Asp Lys Thr His
                245                 250                 255
Thr Cys Pro Pro Cys Pro Ala Pro Glu Leu Leu Gly Gly Pro Ser Val
                260                 265                 270
Phe Leu Phe Pro Pro Lys Pro Lys Asp Thr Leu Met Ile Ser Arg Thr
            275                 280                 285
Pro Glu Val Thr Cys Val Val Val Asp Val Ser His Glu Asp Pro Glu
            290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Glu Tyr Lys
                340                 345                 350
Cys Lys Val Ser Asn Lys Ala Leu Pro Ala Pro Ile Glu Lys Thr Ile
            355                 360                 365
Ser Lys Ala Lys Gly Gln Pro Arg Glu Pro Gln Val Tyr Thr Leu Pro
            370                 375                 380
Pro Ser Arg Glu Glu Met Thr Lys Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
                420                 425                 430
Asp Gly Ser Phe Phe Leu Tyr Ser Lys Leu Thr Val Asp Lys Ser Arg
            435                 440                 445
Trp Gln Gln Gly Asn Val Phe Ser Cys Ser Val Met His Glu Ala Leu
            450                 455                 460
His Asn His Tyr Thr Gln Lys Ser Leu Ser Leu Ser Pro Gly Lys
465                 470                 475

<210> SEQ ID NO 20
```

```
<211> LENGTH: 130
<212> TYPE: PRT
<213> ORGANISM: Homo sapiens

<400> SEQUENCE: 20

Glu Val Gln Leu Val Glu Ser Gly Gly Gly Leu Val Leu Pro Gly Gly
1               5                   10                  15

Ser Leu Arg Leu Ser Cys Ser Ala Ser Gly Phe Thr Leu Thr Asp Phe
            20                  25                  30

Ala Met His Trp Val Arg Gln Ala Pro Gly Lys Gly Leu Glu Leu Val
        35                  40                  45

Ser Ser Ile Ser Arg Asp Gly Ser Thr Lys Tyr Ser Gly Asp Ser Val
    50                  55                  60

Lys Gly Arg Val Ala Ile Ser Arg Asp Ser Val Glu Asn Lys Leu His
65                  70                  75                  80

Leu Gln Met Ser Gly Leu Arg Ser Ala Asp Thr Ala Val Tyr Tyr Cys
                85                  90                  95

Val Arg Asp Ser Pro Tyr Tyr Leu Asp Ile Val Gly Tyr Arg Tyr Phe
            100                 105                 110

His His Tyr Gly Met Asp Val Trp Gly Gln Gly Thr Thr Val Thr Val
        115                 120                 125

Ser Ser
130

<210> SEQ ID NO 21
<211> LENGTH: 5
<212> TYPE: PRT
<213> ORGANISM: Homo sapiens

<400> SEQUENCE: 21

Asp Phe Ala Met His
1               5

<210> SEQ ID NO 22
<211> LENGTH: 17
<212> TYPE: PRT
<213> ORGANISM: Homo sapiens

<400> SEQUENCE: 22

Ser Ile Ser Arg Asp Gly Ser Thr Lys Tyr Ser Gly Asp Ser Val Lys
1               5                   10                  15

Gly

<210> SEQ ID NO 23
<211> LENGTH: 21
<212> TYPE: PRT
<213> ORGANISM: Homo sapiens

<400> SEQUENCE: 23

Asp Ser Pro Tyr Tyr Leu Asp Ile Val Gly Tyr Arg Tyr Phe His His
1               5                   10                  15

Tyr Gly Met Asp Val
            20

<210> SEQ ID NO 24
<211> LENGTH: 6
<212> TYPE: PRT
<213> ORGANISM: Homo sapiens

<400> SEQUENCE: 24
```

<210> SEQ ID NO 25
<211> LENGTH: 10
<212> TYPE: PRT
<213> ORGANISM: Homo sapiens

<400> SEQUENCE: 25

Ser Ile Ser Arg Asp Gly Ser Thr Lys Tyr
1               5                   10

<210> SEQ ID NO 26
<211> LENGTH: 717
<212> TYPE: DNA
<213> ORGANISM: Homo sapiens

<400> SEQUENCE: 26

```
atggaaaccc cagctcagct tctcttcctc ctgctactct ggctcccaga taccaccgga    60
gagattgtgt tgacgcagtc gccaggcacc ctgtctttgt ctccagggga cagagtcacc   120
ctctcctgca gggccagtca aattcttcac agctataatt tagcctggta tcagcacaga   180
cctggccagg ctcccaggct cctcatttat ggtgcatata cagggccag tggcatccca    240
gacaggttca gtggcagtgg gtctgggca gacttcaccc tcaccatcgg cagactgcag    300
cgtgacgatt ttgcagttta ttactgtcaa cagtatggtg actcaccatc accaggcctc   360
actttcggcg gaggaaccaa actggagttc aaacgtacgg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc    660
acccatcagg gcctgagctc gcccgtcaca aagagcttca caggggaga gtgttag       717
```

<210> SEQ ID NO 27
<211> LENGTH: 333
<212> TYPE: DNA
<213> ORGANISM: Homo sapiens

<400> SEQUENCE: 27

```
gagattgtgt tgacgcagtc gccaggcacc ctgtctttgt ctccagggga cagagtcacc    60
ctctcctgca gggccagtca aattcttcac agctataatt tagcctggta tcagcacaga   120
cctggccagg ctcccaggct cctcatttat ggtgcatata cagggccag tggcatccca    180
gacaggttca gtggcagtgg gtctgggca gacttcaccc tcaccatcgg cagactgcag    240
cgtgacgatt ttgcagttta ttactgtcaa cagtatggtg actcaccatc accaggcctc   300
actttcggcg gaggaaccaa actggagttc aaa                                333
```

<210> SEQ ID NO 28
<211> LENGTH: 238
<212> TYPE: PRT
<213> ORGANISM: Homo sapiens

<400> SEQUENCE: 28

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

```
Leu Ser Pro Gly Asp Arg Val Thr Leu Ser Cys Arg Ala Ser Gln Ile
            35                  40                  45

Leu His Ser Tyr Asn Leu Ala Trp Tyr Gln His Arg Pro Gly Gln Ala
 50                  55                  60

Pro Arg Leu Leu Ile Tyr Gly Ala Tyr Asn Arg Ala Ser Gly Ile Pro
 65                  70                  75                  80

Asp Arg Phe Ser Gly Ser Gly Ser Gly Ala Asp Phe Thr Leu Thr Ile
                 85                  90                  95

Gly Arg Leu Gln Arg Asp Asp Phe Ala Val Tyr Tyr Cys Gln Gln Tyr
                100                 105                 110

Gly Asp Ser Pro Ser Pro Gly Leu Thr Phe Gly Gly Gly Thr Lys Leu
            115                 120                 125

Glu Phe Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 29
<211> LENGTH: 111
<212> TYPE: PRT
<213> ORGANISM: Homo sapiens

<400> SEQUENCE: 29

Glu Ile Val Leu Thr Gln Ser Pro Gly Thr Leu Ser Leu Ser Pro Gly
 1               5                  10                  15

Asp Arg Val Thr Leu Ser Cys Arg Ala Ser Gln Ile Leu His Ser Tyr
                20                  25                  30

Asn Leu Ala Trp Tyr Gln His Arg Pro Gly Gln Ala Pro Arg Leu Leu
            35                  40                  45

Ile Tyr Gly Ala Tyr Asn Arg Ala Ser Gly Ile Pro Asp Arg Phe Ser
 50                  55                  60

Gly Ser Gly Ser Gly Ala Asp Phe Thr Leu Thr Ile Gly Arg Leu Gln
 65                  70                  75                  80

Arg Asp Asp Phe Ala Val Tyr Tyr Cys Gln Gln Tyr Gly Asp Ser Pro
                 85                  90                  95

Ser Pro Gly Leu Thr Phe Gly Gly Gly Thr Lys Leu Glu Phe Lys
            100                 105                 110

<210> SEQ ID NO 30
<211> LENGTH: 12
<212> TYPE: PRT
<213> ORGANISM: Homo sapiens

<400> SEQUENCE: 30

Arg Ala Ser Gln Ile Leu His Ser Tyr Asn Leu Ala
 1               5                  10
```

<210> SEQ ID NO 31
<211> LENGTH: 7
<212> TYPE: PRT
<213> ORGANISM: Homo sapiens

<400> SEQUENCE: 31

Gly Ala Tyr Asn Arg Ala Ser
1               5

<210> SEQ ID NO 32
<211> LENGTH: 12
<212> TYPE: PRT
<213> ORGANISM: Homo sapiens

<400> SEQUENCE: 32

Gln Gln Tyr Gly Asp Ser Pro Ser Pro Gly Leu Thr
1               5                   10

<210> SEQ ID NO 33
<211> LENGTH: 1425
<212> TYPE: DNA
<213> ORGANISM: Homo sapiens

<400> SEQUENCE: 33

```
atgaaacacc tgtggttctt cctcctactg atggcggctc ccagatgggt cctgtcccag     60
ctgcaactgc ttgagtcggg cccaagactg gtgaaggctt cggagaccct gtcactcacc    120
tgcagtgtcc ctatgggctc catcctccaa aatgattatc attgggcctg ggtccgccag    180
ccccaggga ggggcctgga gtggattggg agtgttcact atagacaaaa atcctactac    240
agcccgtccc tcaagagccg agtcttcatg tccgtagaca cgtccagaga ccagttctcc    300
ctaaaactct tctctctggc cgccgcggac acggccgtat attattgtgc gagacataat    360
cgggaagatt attatgacag taatgcctac tttgacgagt ggggcctggg agctcggatc    420
accgtctcga gcgcctccac caagggccca tcggtcttcc cctggcacc tcctccaag    480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg    660
ggcacccaga cctacatctg caacgtgaat cacaagccca gcaacaccaa ggtggacaag    720
agagttgagc ccaaatcttg tgacaaaact cacacatgcc caccgtgccc agcacctgaa    780
ctcctggggg gaccgtcagt cttcctcttc ccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgccccca   1140
tcccgggagg agatgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct atagcaagct caccgtggac   1320
aagagcaggt ggcagcaggg gaacgtcttc tcatgctccg tgatgcatga ggctctgcac   1380
aaccactaca cgcagaagag cctctccctg tctccgggta aatga              1425
```

<210> SEQ ID NO 34
<211> LENGTH: 375
<212> TYPE: DNA
<213> ORGANISM: Homo sapiens

<400> SEQUENCE: 34

```
cagctgcaac tgcttgagtc gggcccaaga ctggtgaagg cttcggagac cctgtcactc      60
acctgcagtg tccctatggg ctccatcctc caaaatgatt atcattgggc tgggtccgc      120 cagcccccag ggagggcct ggagtggatt gggagtgttc actatagaca aaatcctac       180 tacagcccgt ccctcaagag ccgagtcttc atgtccgtag acacgtccag agaccagttc     240
tccctaaaac tcttctctct ggccgccgcg gacacggccg tatattattg tgcgagacat     300
aatcgggaag attattatga cagtaatgcc tactttgacg agtggggcct gggagctcgg     360
atcaccgtct cgagc                                                     375
```

<210> SEQ ID NO 35
<211> LENGTH: 474
<212> TYPE: PRT
<213> ORGANISM: Homo sapiens

<400> SEQUENCE: 35

```
Met Lys His Leu Trp Phe Phe Leu Leu Leu Met Ala Ala Pro Arg Trp
 1               5                  10                  15

Val Leu Ser Gln Leu Gln Leu Glu Ser Gly Pro Arg Leu Val Lys
                20                  25                  30

Ala Ser Glu Thr Leu Ser Leu Thr Cys Ser Val Pro Met Gly Ser Ile
         35                  40                  45

Leu Gln Asn Asp Tyr His Trp Ala Trp Val Arg Gln Pro Pro Gly Arg
     50                  55                  60

Gly Leu Glu Trp Ile Gly Ser Val His Tyr Arg Gln Lys Ser Tyr Tyr
 65                  70                  75                  80

Ser Pro Ser Leu Lys Ser Arg Val Phe Met Ser Val Asp Thr Ser Arg
                 85                  90                  95

Asp Gln Phe Ser Leu Lys Leu Phe Ser Leu Ala Ala Ala Asp Thr Ala
            100                 105                 110

Val Tyr Tyr Cys Ala Arg His Asn Arg Glu Asp Tyr Tyr Asp Ser Asn
        115                 120                 125

Ala Tyr Phe Asp Glu Trp Gly Leu Gly Ala Arg Ile Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
```

```
            260                 265                 270
Lys Pro Lys Asp Thr Leu Met Ile Ser Arg Thr Pro Glu Val Thr Cys
            275                 280                 285
Val Val Val Asp Val Ser His Glu Asp Pro Glu Val Lys Phe Asn Trp
            290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
            325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
            355                 360                 365
Gln Pro Arg Glu Pro Gln Val Tyr Thr Leu Pro Pro Ser Arg Glu Glu
            370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
            405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
            435                 440                 445
Val Phe Ser Cys Ser Val Met His Glu Ala Leu His Asn His Tyr Thr
            450                 455                 460
Gln Lys Ser Leu Ser Leu Ser Pro Gly Lys
465                 470

<210> SEQ ID NO 36
<211> LENGTH: 125
<212> TYPE: PRT
<213> ORGANISM: Homo sapiens

<400> SEQUENCE: 36

Gln Leu Gln Leu Leu Glu Ser Gly Pro Arg Leu Val Lys Ala Ser Glu
1               5                   10                  15
Thr Leu Ser Leu Thr Cys Ser Val Pro Met Gly Ser Ile Leu Gln Asn
            20                  25                  30
Asp Tyr His Trp Ala Trp Val Arg Gln Pro Pro Gly Arg Gly Leu Glu
            35                  40                  45
Trp Ile Gly Ser Val His Tyr Arg Gln Lys Ser Tyr Tyr Ser Pro Ser
        50                  55                  60
Leu Lys Ser Arg Val Phe Met Ser Val Asp Thr Ser Arg Asp Gln Phe
65                  70                  75                  80
Ser Leu Lys Leu Phe Ser Leu Ala Ala Ala Asp Thr Ala Val Tyr Tyr
                85                  90                  95
Cys Ala Arg His Asn Arg Glu Asp Tyr Tyr Asp Ser Asn Ala Tyr Phe
            100                 105                 110
Asp Glu Trp Gly Leu Gly Ala Arg Ile Thr Val Ser Ser
            115                 120                 125

<210> SEQ ID NO 37
<211> LENGTH: 7
<212> TYPE: PRT
<213> ORGANISM: Homo sapiens
```

-continued

<400> SEQUENCE: 37

Gln Asn Asp Tyr His Trp Ala
1               5

<210> SEQ ID NO 38
<211> LENGTH: 16
<212> TYPE: PRT
<213> ORGANISM: Homo sapiens

<400> SEQUENCE: 38

Ser Val His Tyr Arg Gln Lys Ser Tyr Tyr Ser Pro Ser Leu Lys Ser
1               5                   10                  15

<210> SEQ ID NO 39
<211> LENGTH: 15
<212> TYPE: PRT
<213> ORGANISM: Homo sapiens

<400> SEQUENCE: 39

His Asn Arg Glu Asp Tyr Tyr Asp Ser Asn Ala Tyr Phe Asp Glu
1               5                   10                  15

<210> SEQ ID NO 40
<211> LENGTH: 8
<212> TYPE: PRT
<213> ORGANISM: Homo sapiens

<400> SEQUENCE: 40

Met Gly Ser Ile Leu Gln Asn Asp
1               5

<210> SEQ ID NO 41
<211> LENGTH: 9
<212> TYPE: PRT
<213> ORGANISM: Homo sapiens

<400> SEQUENCE: 41

Ser Val His Tyr Arg Gln Lys Ser Tyr
1               5

<210> SEQ ID NO 42
<211> LENGTH: 702
<212> TYPE: DNA
<213> ORGANISM: Homo sapiens

<400> SEQUENCE: 42
atggccagct ccctctcct cctcggcgtc cttgcttact gcacagggtc gggggcctcc      60
tatgagttgt ctcagccacc ctcagtgtcc gtgttcccgg acagacagc aagcatcacc     120 tgttctggag atgacttgga aaacacccctt gtttgttggt atcaacaaaa gtcagggcag   180 tccccctgtgt tggtcgtcta tcaagattcc aagcggccct cagggatccc tgagcgattc   240
tctggctcca gagttaaaga cacagccact ctgaccatca gcgggacgca ggctttcgat   300
gaggctgact attattgtca gacgtggcac aggtccaccg cccagtatgt cttcggacct   360
gggaccaagg tcaccgttct aggtcagccc aaggctgccc cctcggtcac tctgttcccg   420
ccctcctctg aggagcttca agccaacaag gccacactgg tgtgtctcat aagtgacttc   480
tacccgggag ccgtgacagt ggcctggaag gcagatagca gccccgtcaa ggcgggagtg   540
gagaccacca cacctccaa acaaagcaac aacaagtacg cggccagcag ctacctgagc   600
ctgacgcctg agcagtggaa gtcccacaaa agctacagct gccaggtcac gcatgaaggg   660
agcaccgtgg agaagacagt ggcccctaca gaatgttcat ag    702

<210> SEQ ID NO 43
<211> LENGTH: 324
<212> TYPE: DNA
<213> ORGANISM: Homo sapiens

<400> SEQUENCE: 43
tcctatgagt tgtctcagcc accctcagtg tccgtgttcc cgggacagac agcaagcatc    60
acctgttctg gagatgactt ggaaaacacc cttgtttgtt ggtatcaaca aaagtcaggg    120
cagtcccctg tgttggtcgt ctatcaagat tccaagcggc cctcagggat ccctgagcga    180
ttctctggct ccagagttaa agacacagcc actctgacca tcagcgggac gcaggctttc    240
gatgaggctg actattattg tcagacgtgg cacaggtcca ccgcccagta tgtcttcgga    300
cctgggacca aggtcaccgt tcta    324

<210> SEQ ID NO 44
<211> LENGTH: 233
<212> TYPE: PRT
<213> ORGANISM: Homo sapiens

<400> SEQUENCE: 44

Met Ala Ser Phe Pro Leu Leu Leu Gly Val Leu Ala Tyr Cys Thr Gly
1               5                   10                  15

Ser Gly Ala Ser Tyr Glu Leu Ser Gln Pro Ser Val Ser Val Phe
            20                  25                  30

Pro Gly Gln Thr Ala Ser Ile Thr Cys Ser Gly Asp Asp Leu Glu Asn
        35                  40                  45

Thr Leu Val Cys Trp Tyr Gln Gln Lys Ser Gly Gln Ser Pro Val Leu
    50                  55                  60

Val Val Tyr Gln Asp Ser Lys Arg Pro Ser Gly Ile Pro Glu Arg Phe
65                  70                  75                  80

Ser Gly Ser Arg Val Lys Asp Thr Ala Thr Leu Thr Ile Ser Gly Thr
                85                  90                  95

Gln Ala Phe Asp Glu Ala Asp Tyr Tyr Cys Gln Thr Trp His Arg Ser
            100                 105                 110

Thr Ala Gln Tyr Val Phe Gly Pro Gly Thr Lys Val Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Lys Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 45
<211> LENGTH: 108
<212> TYPE: PRT

<213> ORGANISM: Homo sapiens

<400> SEQUENCE: 45

Ser Tyr Glu Leu Ser Gln Pro Pro Ser Val Ser Phe Pro Gly Gln
1               5                   10                  15

Thr Ala Ser Ile Thr Cys Ser Gly Asp Asp Leu Glu Asn Thr Leu Val
            20                  25                  30

Cys Trp Tyr Gln Gln Lys Ser Gly Gln Ser Pro Val Leu Val Val Tyr
        35                  40                  45

Gln Asp Ser Lys Arg Pro Ser Gly Ile Pro Glu Arg Phe Ser Gly Ser
    50                  55                  60

Arg Val Lys Asp Thr Ala Thr Leu Thr Ile Ser Gly Thr Gln Ala Phe
65                  70                  75                  80

Asp Glu Ala Asp Tyr Tyr Cys Gln Thr Trp His Arg Ser Thr Ala Gln
                85                  90                  95

Tyr Val Phe Gly Pro Gly Thr Lys Val Thr Val Leu
            100                 105

<210> SEQ ID NO 46
<211> LENGTH: 11
<212> TYPE: PRT
<213> ORGANISM: Homo sapiens

<400> SEQUENCE: 46

Ser Gly Asp Asp Leu Glu Asn Thr Leu Val Cys
1               5                   10

<210> SEQ ID NO 47
<211> LENGTH: 7
<212> TYPE: PRT
<213> ORGANISM: Homo sapiens

<400> SEQUENCE: 47

Gln Asp Ser Lys Arg Pro Ser
1               5

<210> SEQ ID NO 48
<211> LENGTH: 11
<212> TYPE: PRT
<213> ORGANISM: Homo sapiens

<400> SEQUENCE: 48

Gln Thr Trp His Arg Ser Thr Ala Gln Tyr Val
1               5                   10

<210> SEQ ID NO 49
<211> LENGTH: 1425
<212> TYPE: DNA
<213> ORGANISM: Homo sapiens

<400> SEQUENCE: 49
atgaaacacc tgtggttctt cctcctgctg gtggcggctc ccagatgggt cctgtcccag        60
ttgcagctgc ttgagtcggg cccaggactg gtgaagcctt cggagaccct tcactcacc       120 tgcagtgtct ctggggactc cctcctcagt aatgatcaat actgggcctg ggtccgccag      180 ccccaggga ggggcctgga gtggattggg agtgttcact atagacgacg aaactactac       240
agcccgtccc tggagagccg gatcttcatg tcagtagaca cgtccagaaa cgagttctcc      300
ttaaaagttt tctctgtgac ggccgcggac acggccgtgt attattgtgc gagacacaat      360
tgggaagatt attatgagag taatgcctac tttgactact ggggcctggg aacccggatc      420

```
accgtctcga gcgcctccac caagggccca tcggtcttcc ccctggcacc ctcctccaag    480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg     660 ggcacccaga cctacatctg caacgtgaat cacaagccca gcaacaccaa ggtggacaag    720
agagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg    1020
ctgaatggca aggagtacaa gtgcaaggtc tccaacaaag ccctcccagc ccccatcgag    1080
aaaaccatct ccaaagccaa agggcagccc cgagaaccac aggtgtacac cctgccccca    1140
tcccgggagg agatgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct atagcaagct caccgtggac    1320
aagagcaggt ggcagcaggg gaacgtcttc tcatgctccg tgatgcatga ggctctgcac    1380
aaccactaca cgcagaagag cctctccctg tctccgggta aatga                   1425

<210> SEQ ID NO 50
<211> LENGTH: 375
<212> TYPE: DNA
<213> ORGANISM: Homo sapiens

<400> SEQUENCE: 50
cagttgcagc tgcttgagtc gggcccagga ctggtgaagc cttcggagac cctttcactc     60
acctgcagtg tctctgggga ctccctcctc agtaatgatc aatactgggc ctgggtccgc    120
cagcccccag ggaggggcct ggagtggatt gggagtgttc actatagacg acgaaactac    180
tacagcccgt ccctggagag ccggatcttc atgtcagtag acacgtccag aaacgagttc    240
tccttaaaag ttttctctgt gacggccgcg gacacggccg tgtattattg tgcgagacac    300
aattgggaag attattatga gagtaatgcc tactttgact actggggcct gggaacccgg    360
atcaccgtct cgagc                                                     375

<210> SEQ ID NO 51
<211> LENGTH: 474
<212> TYPE: PRT
<213> ORGANISM: Homo sapiens

<400> SEQUENCE: 51

Met Lys His Leu Trp Phe Phe Leu Leu Leu Val Ala Ala Pro Arg Trp
1               5                   10                  15

Val Leu Ser Gln Leu Gln Leu Leu Glu Ser Gly Pro Gly Leu Val Lys
            20                  25                  30

Pro Ser Glu Thr Leu Ser Leu Thr Cys Ser Val Ser Gly Asp Ser Leu
        35                  40                  45

Leu Ser Asn Asp Gln Tyr Trp Ala Trp Val Arg Gln Pro Pro Gly Arg
    50                  55                  60

Gly Leu Glu Trp Ile Gly Ser Val His Tyr Arg Arg Arg Asn Tyr Tyr
65                  70                  75                  80
```

```
Ser Pro Ser Leu Glu Ser Arg Ile Phe Met Ser Val Asp Thr Ser Arg
                85                  90                  95

Asn Glu Phe Ser Leu Lys Val Phe Ser Val Thr Ala Ala Asp Thr Ala
            100                 105                 110

Val Tyr Tyr Cys Ala Arg His Asn Trp Glu Asp Tyr Tyr Glu Ser Asn
        115                 120                 125

Ala Tyr Phe Asp Tyr Trp Gly Leu Gly Thr Arg Ile Thr Val Ser Ser
130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 52
<211> LENGTH: 125
```

<212> TYPE: PRT
<213> ORGANISM: Homo sapiens

<400> SEQUENCE: 52

Gln Leu Gln Leu Leu Glu Ser Gly Pro Gly Leu Val Lys Pro Ser Glu
1               5                   10                  15

Thr Leu Ser Leu Thr Cys Ser Val Ser Gly Asp Ser Leu Leu Ser Asn
            20                  25                  30

Asp Gln Tyr Trp Ala Trp Val Arg Gln Pro Pro Gly Arg Gly Leu Glu
        35                  40                  45

Trp Ile Gly Ser Val His Tyr Arg Arg Arg Asn Tyr Tyr Ser Pro Ser
    50                  55                  60

Leu Glu Ser Arg Ile Phe Met Ser Val Asp Thr Ser Arg Asn Glu Phe
65                  70                  75                  80

Ser Leu Lys Val Phe Ser Val Thr Ala Ala Asp Thr Ala Val Tyr Tyr
                85                  90                  95

Cys Ala Arg His Asn Trp Glu Asp Tyr Tyr Glu Ser Asn Ala Tyr Phe
            100                 105                 110

Asp Tyr Trp Gly Leu Gly Thr Arg Ile Thr Val Ser Ser
        115                 120                 125

<210> SEQ ID NO 53
<211> LENGTH: 7
<212> TYPE: PRT
<213> ORGANISM: Homo sapiens

<400> SEQUENCE: 53

Ser Asn Asp Gln Tyr Trp Ala
1               5

<210> SEQ ID NO 54
<211> LENGTH: 16
<212> TYPE: PRT
<213> ORGANISM: Homo sapiens

<400> SEQUENCE: 54

Ser Val His Tyr Arg Arg Arg Asn Tyr Tyr Ser Pro Ser Leu Glu Ser
1               5                   10                  15

<210> SEQ ID NO 55
<211> LENGTH: 15
<212> TYPE: PRT
<213> ORGANISM: Homo sapiens

<400> SEQUENCE: 55

His Asn Trp Glu Asp Tyr Tyr Glu Ser Asn Ala Tyr Phe Asp Tyr
1               5                   10                  15

<210> SEQ ID NO 56
<211> LENGTH: 8
<212> TYPE: PRT
<213> ORGANISM: Homo sapiens

<400> SEQUENCE: 56

Gly Asp Ser Leu Leu Ser Asn Asp
1               5

<210> SEQ ID NO 57
<211> LENGTH: 9
<212> TYPE: PRT
<213> ORGANISM: Homo sapiens

<400> SEQUENCE: 57

Ser Val His Tyr Arg Arg Arg Asn Tyr
1               5

<210> SEQ ID NO 58
<211> LENGTH: 702
<212> TYPE: DNA
<213> ORGANISM: Homo sapiens

<400> SEQUENCE: 58

```
atggccagct tccctctctt cctcggcgtc cttgcttact gcacaggatc gggggcctcc      60
tttgacttga ctcagccacc ctcagtgtcc gtgtccccag acagaccgc aaccatcacc     120
tgttctggag atcaattgga aaatacctt gtttgctggt atcaacagag gtcaggccag     180
gcccctgtgt tggtcatcta tcaaggttcc aagcggccct cagggatccc tgagcgattc     240
tctggctcca ggtctgggaa cacagccact ctgaccatca gcaggaccca ggctttggat     300
gaggctgact attactgtca ggcgtgggac aggtccaccg cccactatgt cttcggacct     360
gggaccaagg tcaccgttct aggtcagccc aaggctgccc cctcggtcac tctgttcccg     420
ccctcctctg aggagcttca agccaacaag gccacactgg tgtgtctcat aagtgacttc     480
tacccgggag ccgtgacagt ggcctggaag gcagatagca gccccgtcaa ggcgggagtg     540
gagaccacca cacctccaa acaaagcaac aacaagtacg cggccagcag ctacctgagc     600
ctgacgcctg agcagtggaa gtcccacaaa agctacagct gccaggtcac gcatgaaggg     660
agcaccgtgg agaagacagt ggcccctaca gaatgttcat ag                        702
```

<210> SEQ ID NO 59
<211> LENGTH: 324
<212> TYPE: DNA
<213> ORGANISM: Homo sapiens

<400> SEQUENCE: 59

```
tcctttgact tgactcagcc accctcagtg tccgtgtccc caggacagac cgcaaccatc      60
acctgttctg agatcaatt ggaaaatacc tttgtttgct ggtatcaaca gaggtcaggc     120
caggcccctg tgttggtcat ctatcaaggt tccaagcggc cctcagggat ccctgagcga     180
ttctctggct ccaggtctgg gaacacagcc actctgacca tcagcaggac ccaggctttg     240
gatgaggctg actattactg tcaggcgtgg gacaggtcca ccgccactat gtcttcgga      300
cctgggacca aggtcaccgt tcta                                            324
```

<210> SEQ ID NO 60
<211> LENGTH: 233
<212> TYPE: PRT
<213> ORGANISM: Homo sapiens

<400> SEQUENCE: 60

Met Ala Ser Phe Pro Leu Phe Leu Gly Val Leu Ala Tyr Cys Thr Gly
1               5                   10                  15

Ser Gly Ala Ser Phe Asp Leu Thr Gln Pro Pro Ser Val Ser Val Ser
            20                  25                  30

Pro Gly Gln Thr Ala Thr Ile Thr Cys Ser Gly Asp Gln Leu Glu Asn
        35                  40                  45

Thr Phe Val Cys Trp Tyr Gln Gln Arg Ser Gly Gln Ala Pro Val Leu
    50                  55                  60

Val Ile Tyr Gln Gly Ser Lys Arg Pro Ser Gly Ile Pro Glu Arg Phe
65                  70                  75                  80

```
Ser Gly Ser Arg Ser Gly Asn Thr Ala Thr Leu Thr Ile Ser Arg Thr
            85                  90                  95

Gln Ala Leu Asp Glu Ala Asp Tyr Tyr Cys Gln Ala Trp Asp Arg Ser
        100                 105                 110

Thr Ala His Tyr Val Phe Gly Pro Gly Thr Lys Val Thr Val Leu Gly
    115                 120                 125

Gln Pro Lys Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Lys Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 61
<211> LENGTH: 108
<212> TYPE: PRT
<213> ORGANISM: Homo sapiens

<400> SEQUENCE: 61

Ser Phe Asp Leu Thr Gln Pro Pro Ser Val Ser Val Ser Pro Gly Gln
1               5                   10                  15

Thr Ala Thr Ile Thr Cys Ser Gly Asp Gln Leu Glu Asn Thr Phe Val
            20                  25                  30

Cys Trp Tyr Gln Gln Arg Ser Gly Gln Ala Pro Val Leu Val Ile Tyr
        35                  40                  45

Gln Gly Ser Lys Arg Pro Ser Gly Ile Pro Glu Arg Phe Ser Gly Ser
    50                  55                  60

Arg Ser Gly Asn Thr Ala Thr Leu Thr Ile Ser Arg Thr Gln Ala Leu
65                  70                  75                  80

Asp Glu Ala Asp Tyr Tyr Cys Gln Ala Trp Asp Arg Ser Thr Ala His
                85                  90                  95

Tyr Val Phe Gly Pro Gly Thr Lys Val Thr Val Leu
            100                 105

<210> SEQ ID NO 62
<211> LENGTH: 11
<212> TYPE: PRT
<213> ORGANISM: Homo sapiens

<400> SEQUENCE: 62

Ser Gly Asp Gln Leu Glu Asn Thr Phe Val Cys
1               5                   10

<210> SEQ ID NO 63
<211> LENGTH: 7
<212> TYPE: PRT
<213> ORGANISM: Homo sapiens

<400> SEQUENCE: 63
```

```
Gln Gly Ser Lys Arg Pro Ser
1               5
```

<210> SEQ ID NO 64
<211> LENGTH: 11
<212> TYPE: PRT
<213> ORGANISM: Homo sapiens

<400> SEQUENCE: 64

```
Gln Ala Trp Asp Arg Ser Thr Ala His Tyr Val
1               5                   10
```